(12) United States Patent
Kleinstiver et al.

(10) Patent No.: US 12,312,613 B2
(45) Date of Patent: May 27, 2025

(54) UNCONSTRAINED GENOME TARGETING WITH NEAR-PAMLESS ENGINEERED CRISPR-CAS9 VARIANTS

(71) Applicant: The General Hospital Corporation, Boston, MA (US)

(72) Inventors: Benjamin Kleinstiver, Medford, MA (US); Russell T. Walton, Waban, MA (US)

(73) Assignee: The General Hospital Corporation, Boston, MA (US)

( * ) Notice: Subject to any disclaimer, the term of this patent is extended or adjusted under 35 U.S.C. 154(b) by 498 days.

(21) Appl. No.: 17/157,708

(22) Filed: Jan. 25, 2021

(65) Prior Publication Data

US 2021/0284978 A1    Sep. 16, 2021

Related U.S. Application Data

(60) Provisional application No. 62/965,709, filed on Jan. 24, 2020.

(51) Int. Cl.
| | |
|---|---|
| C12N 9/22 | (2006.01) |
| C07K 14/47 | (2006.01) |
| C12N 9/16 | (2006.01) |
| C12N 15/11 | (2006.01) |
| C12N 15/90 | (2006.01) |

(52) U.S. Cl.
CPC ............... *C12N 9/22* (2013.01); *C07K 14/47* (2013.01); *C12N 9/16* (2013.01); *C12N 15/11* (2013.01); *C12N 15/907* (2013.01); *C12Y 301/21004* (2013.01); *C07K 2319/00* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 8,697,359 | B1 | 4/2014 | Zhang |
| 9,322,037 | B2 | 4/2016 | Liu et al. |
| 9,512,446 | B1 | 12/2016 | Joung et al. |
| 9,752,132 | B2 | 9/2017 | Joung et al. |
| 9,926,546 | B2 | 3/2018 | Joung et al. |
| 10,093,910 | B2 | 10/2018 | Joung et al. |
| 10,266,850 | B2 | 4/2019 | Doudna et al. |
| 10,526,591 | B2 | 1/2020 | Joung et al. |
| 10,633,642 | B2 | 4/2020 | Joung et al. |
| 2010/0076057 | A1 | 3/2010 | Sontheimer et al. |
| 2011/0189776 | A1 | 8/2011 | Terns et al. |
| 2011/0223638 | A1 | 9/2011 | Wiedenheft et al. |
| 2013/0130248 | A1 | 5/2013 | Haurwitz et al. |
| 2014/0068797 | A1 | 3/2014 | Doudna et al. |
| 2014/0170753 | A1 | 6/2014 | Zhang |
| 2014/0179006 | A1 | 6/2014 | Zhang |
| 2014/0179770 | A1 | 6/2014 | Zhang et al. |
| 2014/0186843 | A1 | 7/2014 | Zhang et al. |
| 2014/0186919 | A1 | 7/2014 | Zhang et al. |
| 2014/0186958 | A1 | 7/2014 | Zhang et al. |
| 2014/0189896 | A1 | 7/2014 | Zhang et al. |
| 2014/0199767 | A1 | 7/2014 | Barrangou et al. |
| 2014/0201857 | A1 | 7/2014 | Fahrenkrug et al. |
| 2014/0212869 | A1 | 7/2014 | Sampas et al. |
| 2014/0227787 | A1 | 8/2014 | Zhang |
| 2014/0234972 | A1 | 8/2014 | Zhang |
| 2014/0242664 | A1 | 8/2014 | Zhang et al. |
| 2014/0242699 | A1 | 8/2014 | Zhang |
| 2014/0242700 | A1 | 8/2014 | Zhang et al. |
| 2014/0242702 | A1 | 8/2014 | Chen et al. |
| 2014/0248702 | A1 | 9/2014 | Zhang et al. |
| 2014/0256046 | A1 | 9/2014 | Zhang et al. |
| 2014/0271987 | A1 | 9/2014 | Manoury et al. |
| 2014/0273226 | A1 | 9/2014 | Wu |
| 2014/0273230 | A1 | 9/2014 | Chen et al. |
| 2014/0273231 | A1 | 9/2014 | Zhang et al. |
| 2014/0273232 | A1 | 9/2014 | Zhang et al. |
| 2014/0273234 | A1 | 9/2014 | Zhang et al. |
| 2014/0287938 | A1 | 9/2014 | Zhang et al. |
| 2014/0294773 | A1 | 10/2014 | Brouns et al. |
| 2014/0295556 | A1 | 10/2014 | Joung et al. |
| 2014/0298547 | A1 | 10/2014 | Sastry-Dent et al. |
| 2014/0304853 | A1 | 10/2014 | Ainley et al. |
| 2014/0309487 | A1 | 10/2014 | Lee et al. |
| 2014/0310828 | A1 | 10/2014 | Lee et al. |
| 2014/0310830 | A1 | 10/2014 | Zhang et al. |
| 2014/0315985 | A1 | 10/2014 | May et al. |
| 2014/0335063 | A1 | 11/2014 | Cannon et al. |
| 2014/0335620 | A1 | 11/2014 | Zhang et al. |
| 2014/0349400 | A1 | 11/2014 | Jakimo et al. |

(Continued)

FOREIGN PATENT DOCUMENTS

| | | |
|---|---|---|
| CA | 3069296 | 1/2019 |
| CN | 104854241 | 8/2015 |

(Continued)

OTHER PUBLICATIONS

International Preliminary Report on Patentability in International Appln. No. PCT/US2021/014900, mailed on Aug. 4, 2022, 8 pages.
Kleinstiver et al., "Supplementary Materials: Engineered CRISPR-Cas9 nucleases with altered PAM specificities," Nature, Jul. 2015, 523(7561):481-497, 289 pages.
U.S. Appl. No. 61/652,086, filed May 25, 212, Jinek et al.
Abudayyeh et al., "A Cytosine Deaminase for Programmable Single-base RNA Editing," Science, Jul. 26, 2019, 365(6451):382-386.

(Continued)

*Primary Examiner* — Celine X Qian
*Assistant Examiner* — Tiffany Nicole Grooms
(74) *Attorney, Agent, or Firm* — Fish & Richardson P.C.

(57) ABSTRACT

*Streptococcus pyogenes* Cas9 (SpCas9) variants with relaxed PAM requirements capable of high-resolution editing for various applications, and methods of use thereof.

38 Claims, 42 Drawing Sheets

Specification includes a Sequence Listing.

(56) References Cited

U.S. PATENT DOCUMENTS

| | | | |
|---|---|---|---|
| 2014/0357530 A1 | 12/2014 | Zhang et al. | |
| 2014/0377868 A1 | 12/2014 | Joung et al. | |
| 2015/0024500 A1 | 1/2015 | Yu et al. | |
| 2015/0031134 A1 | 1/2015 | Zhang et al. | |
| 2015/0045546 A1 | 2/2015 | Siksnys et al. | |
| 2015/0050699 A1 | 2/2015 | Siksnys et al. | |
| 2015/0071899 A1 | 3/2015 | Liu et al. | |
| 2016/0208243 A1 | 7/2016 | Zhang et al. | |
| 2017/0058271 A1* | 3/2017 | Joung | C12Y 301/00 |
| 2017/0081650 A1 | 3/2017 | Joung et al. | |
| 2017/0233756 A1 | 8/2017 | Begemann et al. | |
| 2018/0100148 A1 | 4/2018 | Vakulskas et al. | |
| 2018/0216088 A1 | 8/2018 | Joung et al. | |
| 2018/0282714 A1 | 10/2018 | Joung et al. | |
| 2018/0320201 A1* | 11/2018 | Vakulskas | C12N 15/88 |
| 2019/0071657 A1 | 3/2019 | Joung et al. | |
| 2019/0106687 A1 | 4/2019 | Joung et al. | |
| 2019/0177710 A1 | 6/2019 | Lee | |
| 2019/0382775 A1 | 12/2019 | Tan et al. | |
| 2020/0140835 A1 | 5/2020 | Joung et al. | |
| 2020/0149024 A1 | 5/2020 | Joung et al. | |
| 2020/0277586 A1 | 9/2020 | Nureki et al. | |
| 2021/0261932 A1 | 8/2021 | Kleinstiver et al. | |
| 2021/0355465 A1 | 11/2021 | Joung et al. | |
| 2021/0380955 A1* | 12/2021 | Bryson | A61P 3/00 |

FOREIGN PATENT DOCUMENTS

| | | | |
|---|---|---|---|
| CN | 105543195 | 5/2016 | |
| CN | 106062197 | 10/2016 | |
| WO | WO 2008/108989 | 9/2008 | |
| WO | WO 2010/054108 | 5/2010 | |
| WO | WO 2012/164565 | 12/2012 | |
| WO | WO 2013/098244 | 7/2013 | |
| WO | WO 2013/176772 | 11/2013 | |
| WO | WO-2013176772 A1* | 11/2013 | C12N 15/102 |
| WO | WO 2014/124284 | 8/2014 | |
| WO | WO 2014/144288 | 9/2014 | |
| WO | WO 2014/144592 | 9/2014 | |
| WO | WO 2014/152432 | 9/2014 | |
| WO | WO-2014152432 A2* | 9/2014 | C12N 9/0071 |
| WO | WO 2014/191521 | 12/2014 | |
| WO | WO 2014/204724 | 12/2014 | |
| WO | WO 2014/204725 | 12/2014 | |
| WO | WO 2015/089364 | 6/2015 | |
| WO | WO 2015/089486 | 6/2015 | |
| WO | WO 2015/200378 | 12/2015 | |
| WO | WO 2016/115179 | 7/2016 | |
| WO | WO 2016/115355 | 7/2016 | |
| WO | WO 2016/141224 | 9/2016 | |
| WO | WO 2016/205613 | 12/2016 | |
| WO | WO 2017/015015 | 1/2017 | |
| WO | WO 2017/040348 | 3/2017 | |
| WO | WO 2017/070633 | 4/2017 | |
| WO | WO-2017070633 A2* | 4/2017 | A61P 31/18 |
| WO | WO 2017/081288 | 5/2017 | |
| WO | WO 2017/184768 | 10/2017 | |
| WO | WO 2018/119359 | 6/2018 | |
| WO | WO 2019/009682 | 1/2019 | |
| WO | WO 2019/040650 | 2/2019 | |
| WO | WO 2019/079347 | 4/2019 | |
| WO | WO 2019/092042 | 5/2019 | |
| WO | WO 2019/217941 | 11/2019 | |
| WO | WO 2019/217942 | 11/2019 | |
| WO | WO 2019/217943 | 11/2019 | |
| WO | WO 2019/217944 | 11/2019 | |
| WO | WO 2020/041751 | 2/2020 | |
| WO | WO 2021/042047 | 3/2021 | |

OTHER PUBLICATIONS

Al-Attar et al, "Clustered Regularly Interspaced Short Palindromic Repeats (CRISPRs): The Hallmark of an Ingenious Antiviral Defense Mechanism in Prokaryotes," Biol Chem. 2011, 392(4):277-289.

Anders et al., "4un3: Crystal structure of Cas9 bound to PAM-containing DNA target," RCSB Protein Data Bank, May 25, 2014, retrieved on May 6, 2016, retrieved from URL <http://www.rcsb.org/pdb/explore/explore.do?structureId=4U>, 3 pages.

Anders et al., "Structural basis of PAM-dependent target DNA recognition by the Cas9 endonuclease," Nature, 2014, 513:569-573.

Anders et al., "Structural Plasticity of PAM Recognition by Engineered Variants of the RNA-Guided Endonuclease Cas9," Molecular Cell, Mar. 17, 2016, 61(6):895-902.

Balemans et al., "Increased bone density in sclerosteosis is due to the deficiency of a novel secreted protein (SOST)," Hum Mol Genet., 2001, 10(5):537-543.

Barrangou & May, "Unraveling the potential of CRISPR-Cas9 for gene therapy," Expert Opin. Biol. Ther., 2014, 15:311-314.

Bisaria et al., "Lessons from Enzyme Kinetics Reveal Specificity Principles for RNA-Guided Nucleases in RNA Interference and CRISPR-Based Genome Editing," Cell Syst., Jan. 2017, 4(1):21-29.

Canela et al., "DNA Breaks and End Resection Measured Genomewide by End Sequencing," Molecular Cell, 2016, 63: 1-14.

Canver et al., "BCL11A enhancer dissection by Cas9-mediated in situ saturating mutagenesis," Nature., 2015, 527(7577), 192-7.

Carroll, "A CRISPR Approach to Gene Targeting," Molecular Therapy, Sep. 2012, 20:(9)1658-1660.

Casini et al, "A highly specific SpCas9 variant is identified by in vivo screening in yeast," Nat. Biotechnol., 2018, 36(3):265-271.

Cencic et al., "Protospacer Adjacent Motif (PAM)-Distal Sequences Engage CRISPR Cas9 DNA Target Cleavage," Oct. 2014, PLOS One, 9(10):e109213, 13 pages.

Chen & Zhao, "A highly sensitive selection method for directed evolution of homing endonucleases," Nucleic Acids Res., 2005, 33(18):e154, 7 pages.

Chen et al., "Enhanced proofreading governs CRISPR-Cas9 targeting accuracy," Nature, Oct. 2017, 550(7676):407-410.

Choi & Meyerson, "Targeted genomic rearrangements using CRISPR/Cas technology," Nat Commun., Apr. 24, 2014, 5:3728, 9 pages.

Chu et al., "Rationally Designed Base Editors for Precise Editing of the Sickle Cell Disease Mutation," The CRISPR Journal, Apr. 20, 2021, 4(2):169-177.

Chylinski et al., "The tracrRNA and Cas9 families of type II CRISPR-Cas immunity systems," RNA Biol., May 2013, 10:726-737.

Clement et al., "CRISPResso2 provides accurate and rapid genome editing sequence analysis," Nature Biotechnology, Feb. 2019, 37:224-226.

Cong et al., "Multiplex genome engineering using CRISPR/Cas systems," Science, 2013, 339:819-823 (Author Manuscript).

Courtney et al., "CRISPR/Cas9 DNA cleavage at SNP-derived PAM enables both in vitro and in vivo KRT12 mutation-specific targeting," Gene Ther., 2016, 23(1):108-12.

Cox et al., "Congenital insensitivity to pain: novel SCN9A missense and in-frame deletion mutations," Hum Mutat., 2010, 31:E1670-86.

Crosetto et al, "Nucleotide-resolution DNA double-strand break mapping by next-generation sequencing," Apr. 2013, Nat Methods 10(4): 361-365.

Dagdas et al., "A Conformational Checkpoint Between DNA Binding and Cleavage by CRISPR-Cas9," Science Advances, Aug. 2017, 3(8): eaao0027.

Deltcheva et al., "CRISPR RNA maturation by trans-encoded small RNA and host factor RNase III," Nature, 2011, 471(7340):602-607 (Author Manuscript).

Deveau et al., "Phage response to CRISPR-encoded resistance in *Streptococcus thermophilus*," J Bacteriol., 2008, 190(4):1390-400.

DiCarlo et al., "Genome engineering in *Saccharomyces cerevisiae* using CRISPR-Cas systems," Nucleic Acids Res, 2013, 1-8.

Ding et al., "Enhanced efficiency of human pluripotent stem cell genome editing through replacing TALENs with CRISPRs," Cell Stem Cell., Apr. 4, 2013, 12(4):393-4 (Author Manuscript).

Doench et al., "Optimized sgRNA design to maximize activity and minimize off-target effects of CRISPR-Cas9," Nature Biotechnology, Jan. 18, 2016, 34:184-191, 12 pages.

Dong et al., "The crystal structure of Cpf1 in complex with CRISPR RNA," Nature, 2016, 532(7600):522-526.

(56) References Cited

OTHER PUBLICATIONS

Doudna & Charpentier, "The new frontier of genome engineering with CRISPR-Cas9," Science, Nov. 2014, 346(6213):1258096, 10 pages.
Doyon et al., "Directed evolution and substrate specificity profile of homing endonuclease I-SceI," J. Am. Chem. Soc., 2006, 128:2477-2484.
Duan et al., "Genome-wide identification of CRISPR/Cas9 off-targets in human genome," Cell Res, 2014, 24(8):1009-1012.
Elliott et al., "Gene Conversion Tracts from Double-Strand Break Repair in Mammalian Cells," Mol Cell Biol., 1998, 18:93-101.
Esvelt et al., "Orthogonal Cas9 proteins for RNA-guided gene regulation and editing," Nat. Methods, 2013, 10:1116-1121.
Findlay et al., "Saturation editing of genomic regions by multiplex homology-directed repair," Nature, 2014, 513:120-3.
Flannick et al., "Loss-of-function mutations in SLC30A8 protect against type 2 diabetes," Nat Genet., 2014, 46:357-63.
Fonfara et al., "Phylogeny of Cas9 determines functional exchangeability of dual-RNA and Cas9 among orthologous type II CRISPR-Cas systems." Nucleic Acids Res., 2014, 42(4): 2577-2590.
Fu et al., "High-frequency off-target mutagenesis induced by CRISPR-Cas nucleases in human cells," Nat Biotechnol., 2013, 31:822-826 (Author Manuscript).
Fu et al., "Improving CRISPR-Cas nuclease specificity using truncated guide RNAs," Nat. Biotechnol, Mar. 2014, 32(3):279-284.
Gabriel et al., "An unbiased genome-wide analysis of zinc-finger nuclease specificity," Nat Biotechnol., 2011, 29:816-823.
Gagnon et al, "Efficient mutagenesis by Cas9 protein-mediated oligonucleotide insertion and large-scale assessment of single-guide RNAs," PLoS One, 2014, 9, e98186.
Gaj et al., "ZFN, TALEN and CRISPR/Cas-based methods for genome engineering," Trends Biotechnol,, Jul. 2013, 31(7):397-405.
Gao et al., "Engineered Cpf1 variants with altered PAM specificities," Nat Biotechnol., 2017, 35:789-792.
Gasiunas et al., "Cas9-crRNA ribonucleoprotein complex mediates specific DNA cleavage for adaptive immunity in bacteria," Proc Natl Acad Sci USA, 2012, 109(39):E2579-E2586.
Gaudelli et al., "Programmable base editing of A•T to G•C in genomic DNA without DNA cleavage," Nature, Nov. 23, 2017, 551:464-471.
Gehrke et al., "An APOBEC3A-Cas9 base editor with minimized bystander and off-target activities," Nature Biotechnology, Nov. 2018, 36(10):977-982, 8 pages.
GenBank Accession No. AKS40380.1, "Cas9 [Synthetic plasmid pFC330]," Aug. 2, 2015, 1 page.
GenBank Acceesion No. EOS46485.1, "The Genome Sequence of Lachnospiraceae bacterium COE1," May 29, 2013, 2 pages.
GenBank Accession No. NP_472073, "hypothetical protein lin2744 [listeria innocua C!ip11262]," Dec. 17, 2014, 2 pages.
GenBank Accession No. WP_010922251.1, "type II CR.ISPR RNA-guided endonuclease Cas9 [*Streptococcus pyogenes*]," Oct. 7, 2015, 2 pages.
Grünewald et al., "CRISPR DNA Base Editors with Reduced RNA Off-Target and Self-Editing Activities," Nature Biotechnology, Sep. 2, 2019, 37(9):1041-1048, 10 pages.
Grünewald et al., "Transcriptome-wide off-target RNA editing induced by CRISPR-guided DNA base editors," Nature, May 16, 2019, 569(7756):433-437, 18 pages.
Guilinger et al., "Fusion of Catalytically Inactive Cas9 to FokI Nuclease Improves the Specificity of Genome Modification," Nat Biotechnol., Apr. 2014, 32:577-582.
Guo et al., "Structural insights into a high fidelity variant of SpCas9," Cell Res., 2019, 29:183-192.
Hale et al, "Essential Features and Rational Design of CRISPR RNAs That Function With the Cas RAMP Module Complex to Cleave RNAs," Mol Cell., Feb. 2012, 45(3):292-302.
Harper et al., "Protective alleles and modifier variants in human health and disease," Nat Rev Genetics, 2015, 16:689-701.
Heigwer et al., "E-CRISP: fast CRISPR target site identification," Nat Methods, Feb. 2014, 11:122-123.
Heler et al., "Cas9 specifies functional viral targets during CRISPR-Cas adaptation," Nature, 2015, 519:199-202.
Hirano et al., "Structural Basis for the Altered PAM Specificities of Engineered CRISPR-Cas9," Mol Cell, Mar. 2017, 61:886-94.
Horvath et al., "Diversity, activity, and evolution of CRISPR loci in *Streptococcus thermophilus*," J. Bacteriol., Feb. 2008, 190:1401-1412.
Hou et al, "Efficient genome engineering in human pluripotent stem cells using Cas9 from Neisseria meningitidis," Proc. Natl. Acad. Sci. USA, Sep. 2013, 110(39):15644-15649.
Hsu et al., "Development and Applications of CRISPR-Cas9 for Genome Engineering," Cell, 2014, 157(6):1262-1278.
Hsu et al., "DNA targeting specificity of RNA-guided Cas9 nucleases," Nat Biotechnol., 2013, 31:827-832.
Hu et al., "Evolved Cas9 variants with broad PAM compatibility and high DNA specificity," Nature, 2018, 556:57-63.
Hwang et al., "Efficient In Vivo Genome Editing Using RNA-Guided Nucleases," Nat. Biotechnol., 2013, 31:227-229 (Author Manuscript).
Iyer et al., "Prediction of novel families of enzymes involved in oxidative and other complex modifications of bases in nucleic acids," Cell Cycle, 2009, 8(11):1698-710.
Jiang et al., "A Cas9-guide RNA complex preorganized for target DNA recognition," Science, Jun. 2015, 348(6242):1477-1481.
Jiang et al., "CRISPR-assisted editing of bacterial genomes," Nat Biotechnol., 2013, 31:233-239 (Author Manuscript).
Jiang et al., "Structures of a CRISPR-Cas9 R-loop complex primed for DNA cleavage," Science, Feb. 2016, 351(6275):867-871.
Jinek et al., "A programmable dual-RNA-guided DNA endonuclease in adaptive bacterial immunity," Science, 2012, 337:816-821.
Jinek et al., "RNA-programmed genome editing in human cells," Elife, 2013, 2:e00471, 9 pages.
Jinek et al., "Structures of Cas9 endonucleases reveal RNA-mediated conformational activation," Science, Mar. 2014, 343(6176):1247997, 13 pages.
Kan et al., "Mechanisms of precise genome editing using oligonucleotide donors," Genome Res., 2017, 27:1099-1111.
Karvelis et al., "Rapid characterization of CRISPR-Cas9 protospacer adjacent motif sequence elements," Genome Biol., 2015, 16:253, 13 pages.
Keegan et al, "ADAR RNA editing below the backbone," RNA, Sep. 2017, 23(9):1317-1328.
Kim et al., "Deep learning improves prediction of CRISPR-Cpf1 guide RNA activity," Nature Biotechnology, Jan. 29, 2018, 36:239-241, 6 pages.
Kim et al., "SpCas9 activity prediction by DeepSpCas9, a deep learning-based model with high generalization performance," Science Advances, Nov. 6, 2019, 5(11):eaax9249, 9 pages.
Kim et al., "Genome-wide target specificities of CRISPR-Cas9 nucleases revealed by multiplex Digenome-seq," Genome Res, 2016, 26: 406-415.
Kleinstiver et al., "A unified genetic, computational and experimental framework identifies functionally relevant residues of the homing endonuclease I-BmoI," Nucleic Acids Res., 2010, 38(7):2411-2427.
Kleinstiver et al., "Engineered CRISPR-Cas12a variants with increased activities and improved targeting ranges for gene, epigenetic and base editing," Nat Biotechnol., Feb. 11, 2019, 37:276-282.
Kleinstiver et al., "High-fidelity CRISPR-Cas9 nucleases with No. detectable genome-wide offtarget effects," Nature, Jan. 2016, 529:490-495.
Kleinstiver et al., "Broadening the targeting range of *Staphylococcus aureus* CRISPR-Cas9 by modifying PAM recognition," Nature Biotechnology, Dec. 2015, 33(12):1293-1298.
Kleinstiver et al., "Engineered CRISPR-Cas9 nucleases with altered PAM specificities," Nature, 2015, 523(7561):481-485.
Koblan et al., "Improving cytidine and adenine base editors by expression optimization and ancestral reconstruction," Nat Biotechnol., Oct. 2018, 36:843-846.

(56) References Cited

OTHER PUBLICATIONS

Komor et al, "Improved base excision repair inhibition and bacteriophage Mu Gam protein yields C:G-to-T:A base editors with higher efficiency and product purity," Sci. Adv., Aug. 2017, 3:eaao4774, 9 pages.
Komor et al., "CRISPR-Based Technologies for the Manipulation of Eukaryotic Genomes," Cell, Jan. 12, 2017, 168(1-2):20-36.
Komor et al., "Programmable editing of a target base in genomic DNA without double-stranded DNA cleavage," Nature, May 2016, 533(7603):420-424.
Lin et al., "CRISPR/Cas9 systems have off-target activity with insertions or deletions between target DNA and guide RNA sequences," Nucleic Acids Res., 2014, 42:7473-7485.
Lindahl et al., "DNA N-glycosidases: properties of uracil-DNA glycosidase from *Escherichia coli*," J. Biol. Chem., May 1977, 252:3286-3294.
Makarova et al., "Evolution and classification of the CRISPR-Cas systems," Nat. Rev. Microbiol., 2011, 9(6):467-77.
Mali et al., "Cas9 as a versatile tool for engineering biology," Nature Methods, 2013, 10(10):957-963.
Mali et al., "RNA-guided human genome engineering via Cas9," Science, Feb. 2013, 339:823-826 (Author Manuscript).
Mali et al., "CAS9 transcriptional activators for target specificity screening and paired nickases for cooperative genome engineering," Nat Biotechnol, Sep. 2013, 31(9): 833-838.
McShan et al., "Genome sequence of a nephritogenic and highly transformable M49 strain of *Streptococcus pyogenes*," J. Bacteriol., 2008, 190:7773-7785.
Melamede et al., "Isolation and characterization of endonuclease VIII from *Escherichia coli*," Biochemistry, Feb. 1994, 33:1255-1264.
Mojica et al., "Short motif sequences determine the targets of the prokaryotic CRISPR defence system," Microbiology, Jan. 2009, 155:733-740.
Nishida et al, "Targeted nucleotide editing using hybrid prokaryotic and vertebrate adaptive immune systems," Science, Sep. 2016, 53(6305), 14 pages.
Nishimasu et al., "Crystal structure of Cas9 in complex with guide RNA and target DNA," Cell, 2014, 156:935-949.
Nishimasu et al., "Engineered CRISPR-Cas9 nuclease with expanded targeting space," Science, Sep. 21, 2018, 361(6408):1259-1262.
PCT International Preliminary Report on Patentability in International Appln. No. PCT/US2016/020756, dated Sep. 14, 2017.
PCT International Preliminary Report on Patentability in International Appln. No. PCT/US2016/049147, dated Mar. 6, 2018, 8 pages.
PCT International Preliminary Report on Patentability in International Appln. No. PCT/US2018/036293, dated Dec. 10, 2019, 8 pages.
PCT International Preliminary Report on Patentability in International Appln. No. PCT/US2018/047577, dated Feb. 25, 2020, 8 pages.
PCT International Search Report and Written Opinion in International Appln. No. PCT/US2016/020756, dated Jul. 26, 2016, 12 pages.
PCT International Search Report and Written Opinion in International Appln. No. PCT/US2016/049147, dated Dec. 23, 2016, 12 pages.
PCT International Search Report and Written Opinion in International Appln. No. PCT/US2017/043753, dated Dec. 28, 2017, 18 pages.
PCT International Search Report and Written Opinion in International Appln. No. PCT/US2018/028919, dated Oct. 1, 2018, 17 pages.
PCT International Search Report and Written Opinion in International Appln. No. PCT/US2018/036293, dated Nov. 8, 2018, 13 pages.
PCT International Search Report and Written Opinion in International Appln. No. PCT/US2021/014900, dated Jul. 21, 2021, 12 pages.
PCT International Search Report and Written Opinion in International Appln. No. PCT/US2021/014933, dated Jul. 20, 2021, 12 pages.
PCT Invitation to Pay Additional Fees in International Appln. No. PCT/US2016/049147, dated Oct. 31, 2016, 2 pages.
Perez-Pinera et al., "RNA-guided gene activation by CRISPR-Case9-based transcription factors," Nat Methods, 2013, 10(10):973-976.
Pinello et al, "Analyzing CRISPR genome-editing experiments with CRISPResso," Nat. Biotechnol., Jul. 2016, 34(7): 695-697.
Ran et al., "Double Nicking by RNA-Guided CRISPR Cas9 for Enhanced Genome Ediitng Specificity," Cell, 2013, 154(6):1380-1389.
Ran et al., "In vivo genome editing using *Staphylococcus aureus* Cas9," Nature, 2015, 520:186-191.
Rees et al., "Base editing: precision chemistry on the genome and transcriptome of living cells," Nat. Rev. Genet., Dec. 2018, 19(12):770-788.
Reyon et al, "FLASH assembly of TALENs for high-throughput genome editing," Nat. Biotechnol., May 2012, 30(5):460-465.
Rohland et al., "Cost-effective, high-throughput DNA sequencing libraries for multiplexed target capture," Genome Research, Jan. 2012, 22:939-946.
Rutkauskas et al., "Directional R-Loop Formation by the CRISPR-Cas Surveillance Complex Cascade Provides Efficient Off-Target Site Rejection," Cell Rep., Mar. 2015, 10(9):1534-1543.
Sander et al., "CRISPR-Cas systems for editing, regulating and targeting genomes," Nat Biotechnol., Apr. 2014, 32(4):347-55.
Sang, "Prospects for transgenesis in the chick," Mechanisms of Development, Sep. 2004, 121:1179-1186.
Sapranauskas et al, "The *Streptococcus thermophilus* CRISPR/Cas system provides immunity in *Escherichia coli*," Nucleic Acids Res., Aug. 2011, 39(21):9275-9282.
Savva et al, "The ADAR protein family," Genome Biol., Dec. 2012, 13(12):252, 10 pages.
Schuelke et al., "Myostatin Mutation Associated with Gross Muscle Hypertrophy in a Child," New Engl J Med., 2004, 350:2682-2688.
Shah et al, "Protospacer recognition motifs," RNA Biol., Feb. 2013, 10(5):891-899.
Shi et al., "Discovery of cancer drug targets by CRISPR-Cas9 screening of protein domains," Nat Biotechnol., 2015, 33:661-7.
Slaymaker et al, "Rationally engineered Cas9 nucleases with improved specificity," Science, Jan. 2016, 351(6268):84-88.
Spencer et al., "Deep mutational scanning of *S. pyogenes* Cas9 reveals important functional domains," Scientific Reports, Dec. 4, 2017, 7(16836), 14 pages.
Sternberg et al., "Conformational control of DNA target cleavage by CRISPR-Cas9" Nature, 2015, 527:110-113.
Sternberg et al., "DNA interrogation by the CRISPR RNA-guided endonuclease Cas9," Nature, Jan. 2014, 507(7490):62-67.
Suzuki et al., "In vivo genome editing via CRISPR/Cas9 mediated homology-independent targeted integration," Nature, 2016, 540:144-149.
Szczelkun et al., "Direct observation of R-loop formation by single RNA-guided Cas9 and Cascade effector complexes," Proc. Natl. Acad. Sci. USA., 111(27):9798-9803.
TG and HDL Working Group of the Exome Sequencing Project, National Heart, Lung, and Blood Institute, "Loss-of-function mutations in APOC3, triglycerides, and coronary disease," New Engl J Med., 2014, 371:22-31.
The Myocardial Infarction Genetics Consortium Investigators, "Inactivating mutations in NPCIL1 and protection from coronary heart disease," New Engl J Med., 2014, 371:2072-82.
Tsai & Joung., "Defining and improving the genome-wide specificities of CRISPR-Cas9 nucleases," Nat. Rev. Genet., 2016, 17(5):300-312.
Tsai et al., "Dimeric CRISPR RNA-guided FokI nucleases for highly specific genome editing," Nat. Biotechnol., 2014, 32(6):569-576.
Tsai et al., "GUIDE-Seq enables genome-wide profiling of off-target cleavage by CRISPR-Cas nucleases," Nat Biotechnol, Feb. 2015, 33:187-197.

(56) References Cited

OTHER PUBLICATIONS

UniProt Database Accession No. U5ULJ7, "Full-Csn1 family CRISPR-associated protein," Jan. 22, 2014, 1 page.
Vakulskas et al, "A high-fidelity Cas9 mutant delivered as a ribonucleoprotein complex enables efficient gene editing in human haematopoietic stem and progenitor cells," Nature Medicine, Aug. 2018, 24(8):1216-1224.
Vierstra et al, "Functional footprinting of regulatory DNA," Nat. Methods, Oct. 2015, 12(10):927-30.
Walton et al., "Unconstrained genome targeting with near-PAMless engineered CRISPR-Cas9 variants," Science, Apr. 17, 2020, 368:290-296, 7 pages.
Wang et al., Regenerative medicine: targeted genome editing in vivo. Cell Research, Jan. 2015, 25: 271-272,.
Wiedenheft et al, "RNA-guided genetic silencing systems in bacteria and archaea," Nature, 2012, 482:331-338.
Wolf et al, "tadA, an essential tRNA-specific adenosine deaminase from *Escherichia coli*," EMBO J., Jul. 2002, 21(14):3841-3851.
Wright et al., "Rational design of a split-Cas9 enzyme complex," Proc. Natl. Acad. Sci. USA., Mar. 2015, 112(10):2984-2989.
Zetsche et al., "Cpf1 Is a Single RNA-Guided Endonuclease of a Class 2 CRISPR-Cas System," Cell, 2015, 163:759-771.

Zhang et al., "Comparison of non-canonical PAMS for CRISPR/Cas9-mediated DNA cleavage in human cells," Sci Rep, Jun. 2014, 4:5405, 5 pages.
Zhang et al., "Processing-Independent CRISPR RNAs Limit Natural Transformation in Neisseria meningitidis," Mol Cell, May 2013, 50(4):488-503.
Nishimasu et al., "Crystal Structure of *Staphylococcus aureus* Cas9," Cell, 2015, 162:1113-1126.
Li et al., "Advances in detecting and reducing off-target effects generated by CRISPR-mediated genome editing," Journal of Genetics and Genomics, Nov. 2019, 46(11):513-521.
Partial European Search Report in European Appln. No. 21744681.4, dated Dec. 20, 2023, 19 pages.
Lee et al., "Directed evolution of CRISPR-Cas9 to increase its specificity," Nat Commun., Aug. 2018, 9(1):3048, 10 pages.
Xu et al., "SpRY greatly expands the genome editing scope in rice with highly flexible PAM recognition," Jan. 2021, 22(1):6, 15 pages.
Nishimasu et al., "Supplemental Information: Crystal Structure of *Staphylococcus aureus* Cas9," Cell, 2015, 11 pages.
Extended European Search Report in European Appln. No. 21744681.4, dated Mar. 13, 2024, 17 pages.

\* cited by examiner

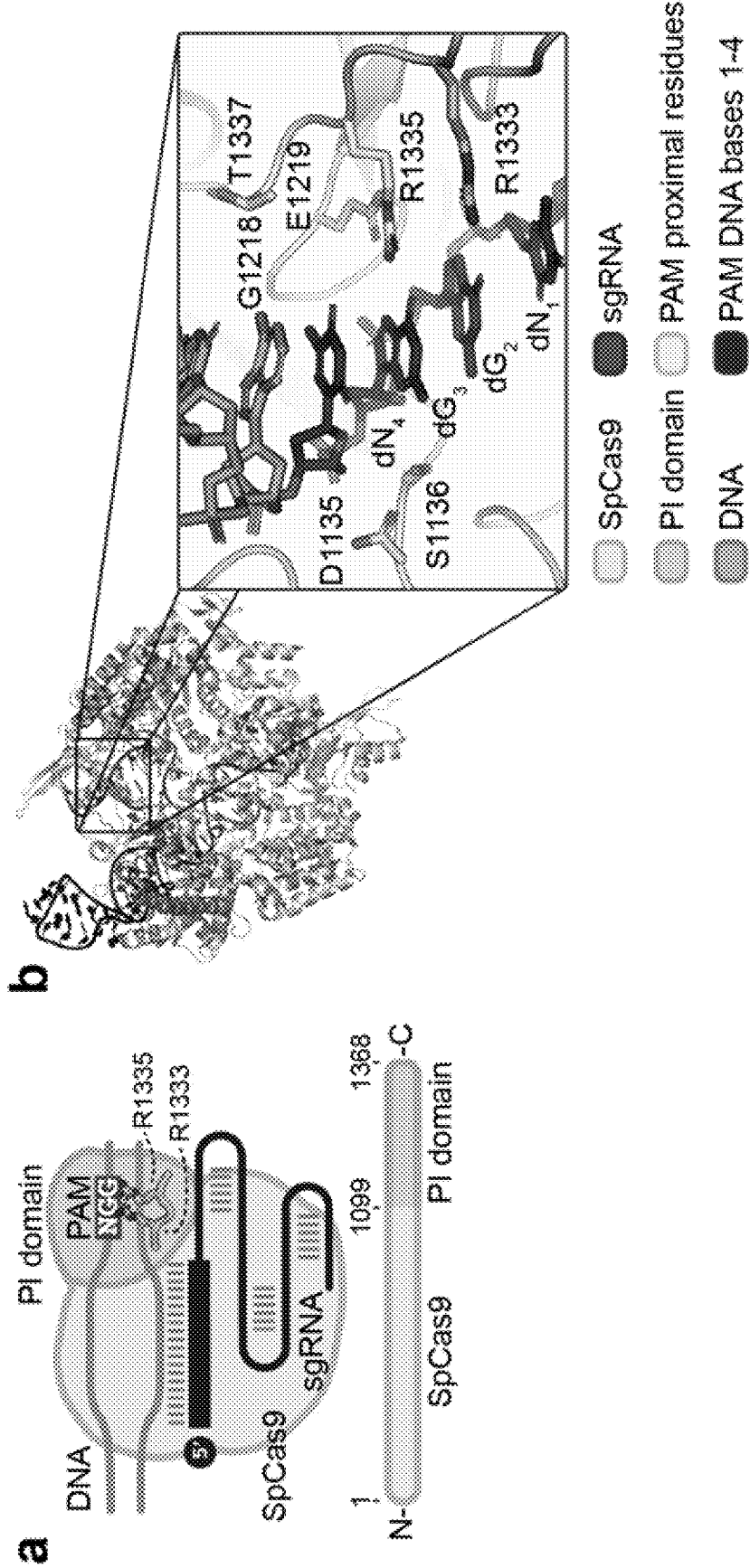
FIGs. 1A-B

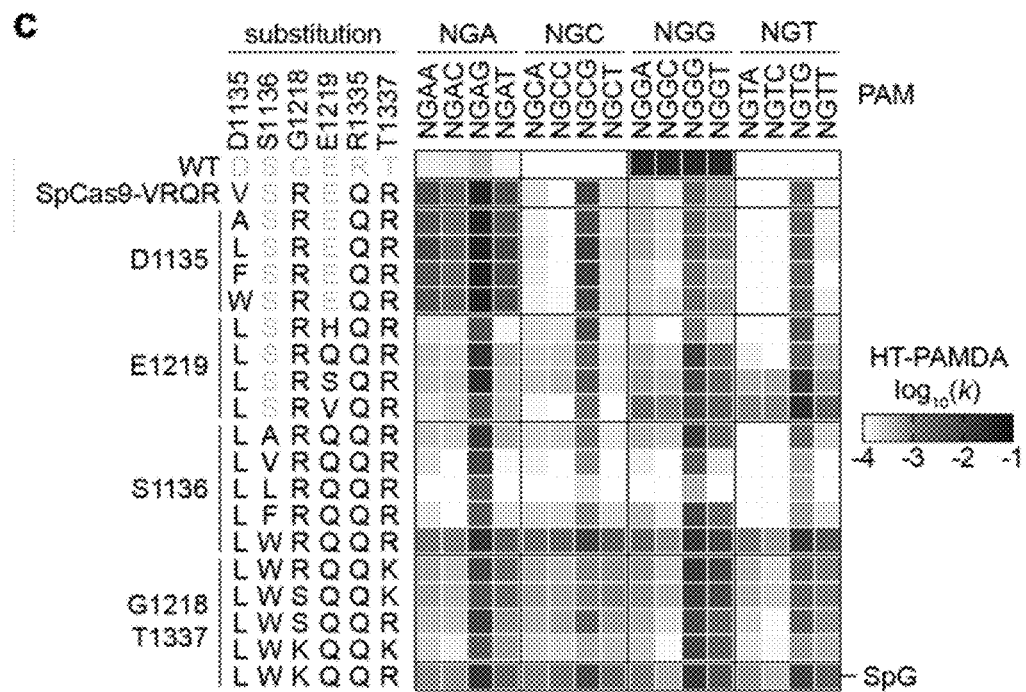
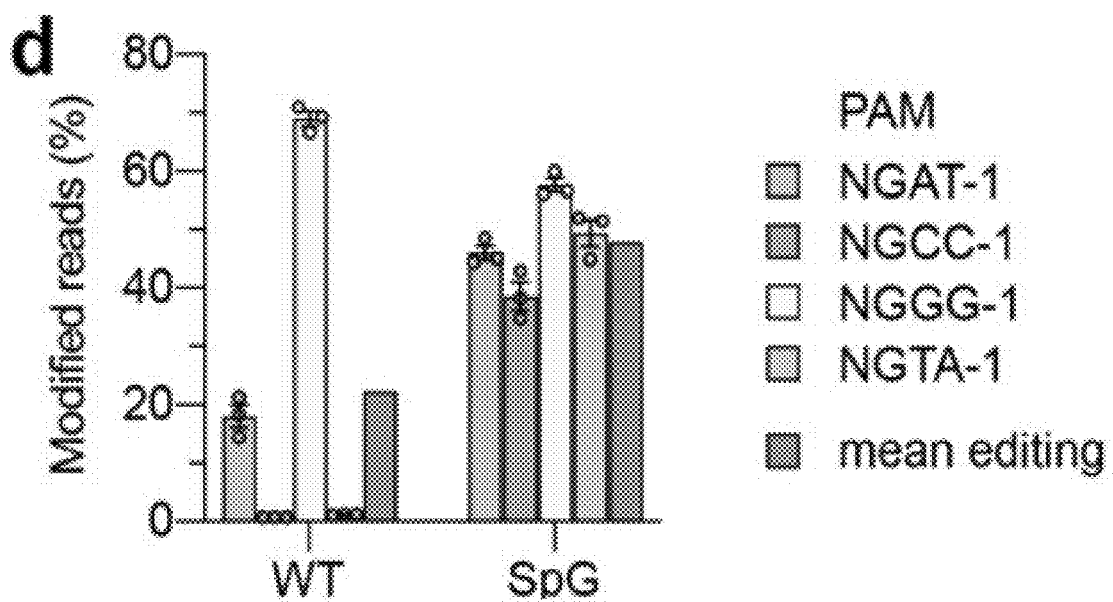
FIGs. 1C-D

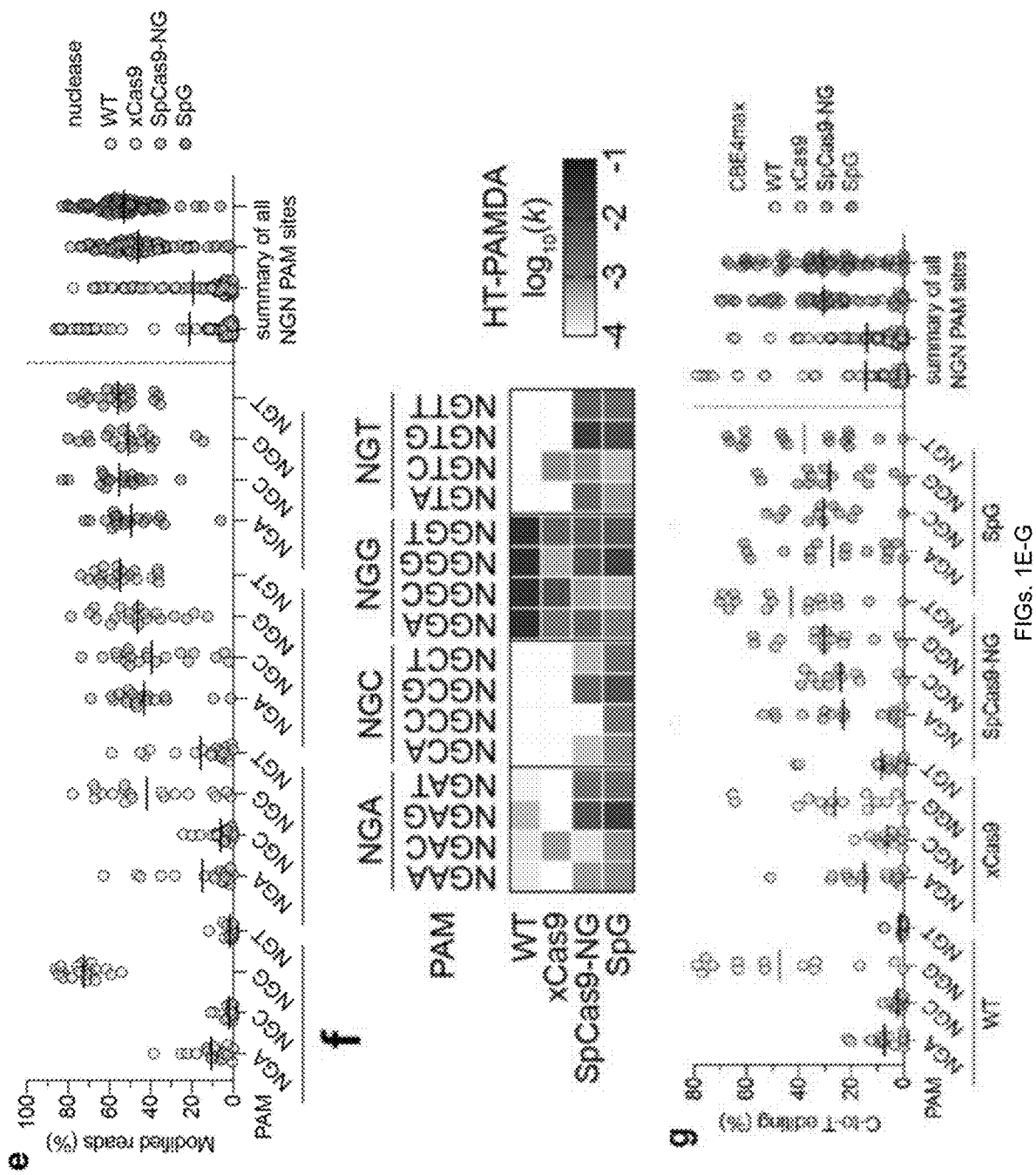
FIGs. 1E-G

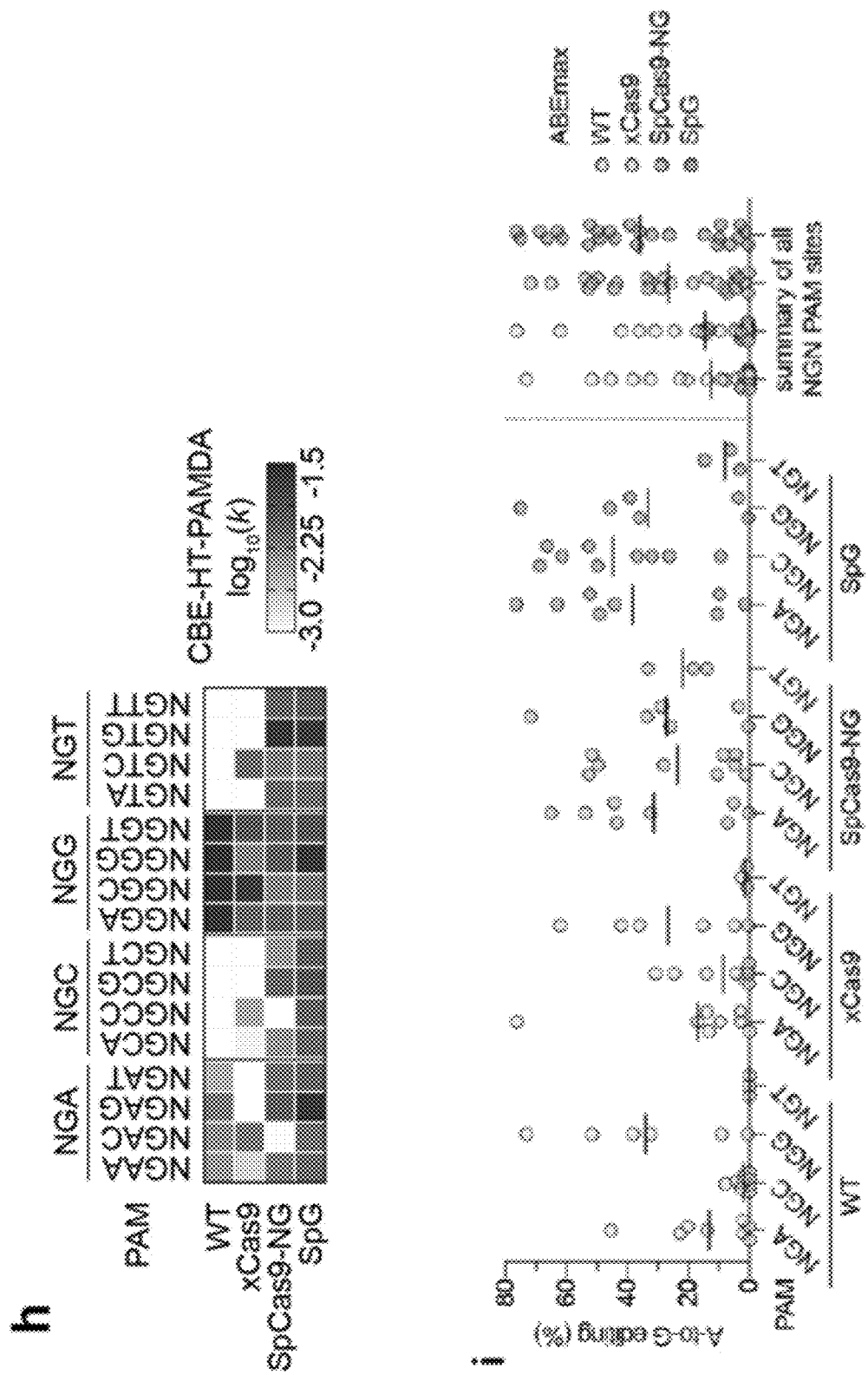
FIGs. 1H-I

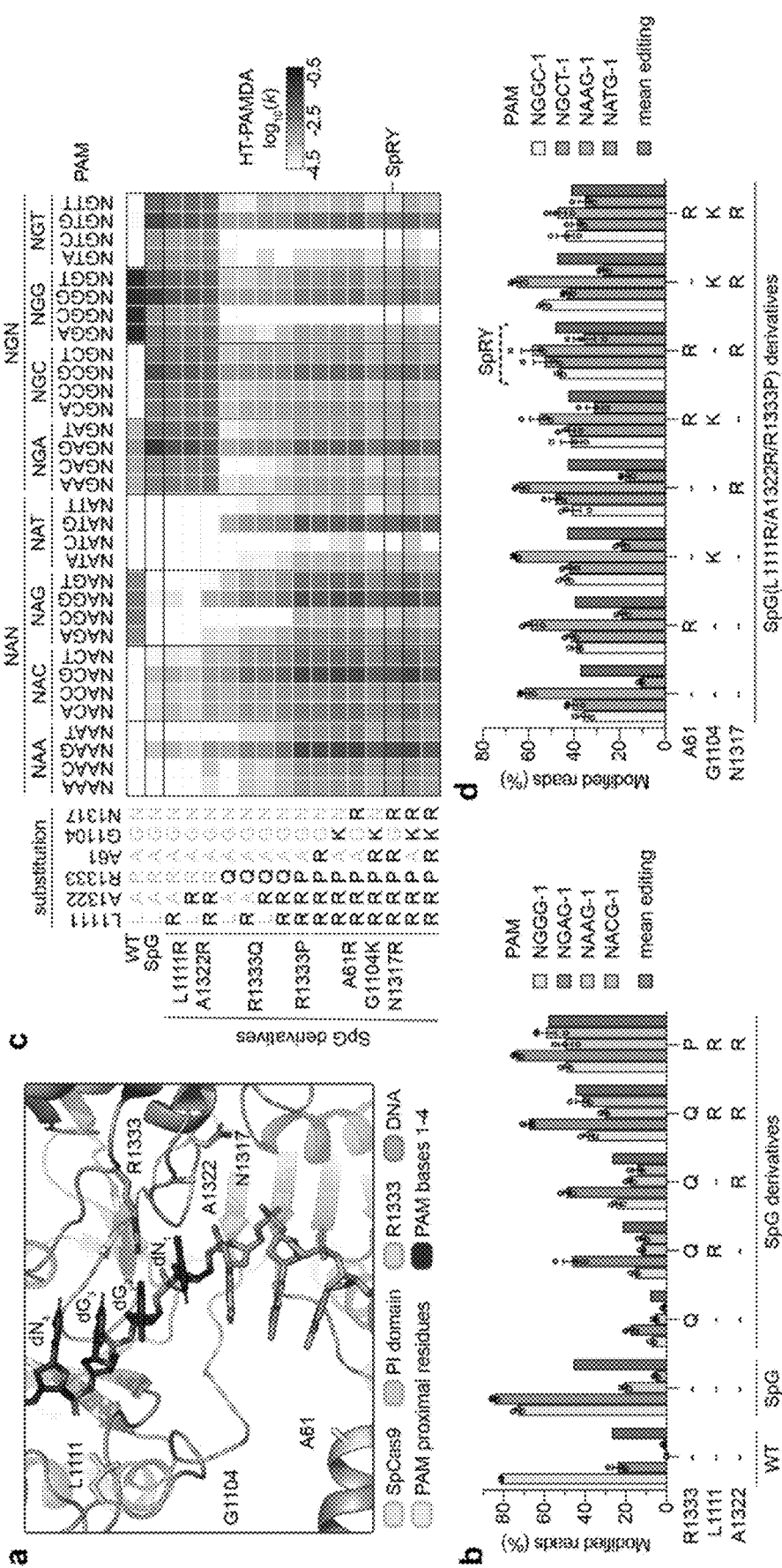
FIGs. 2A-D

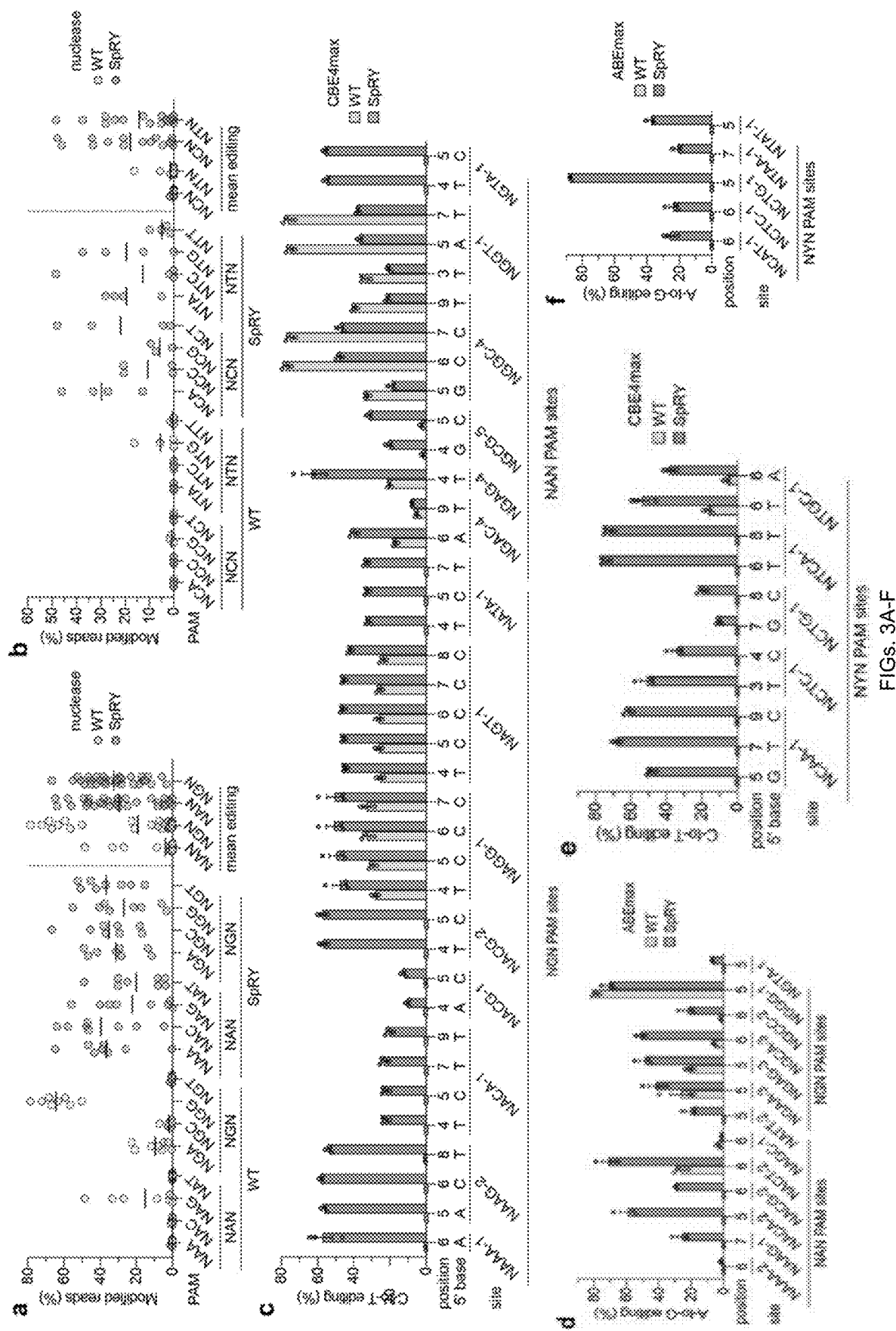
FIGs. 3A-F

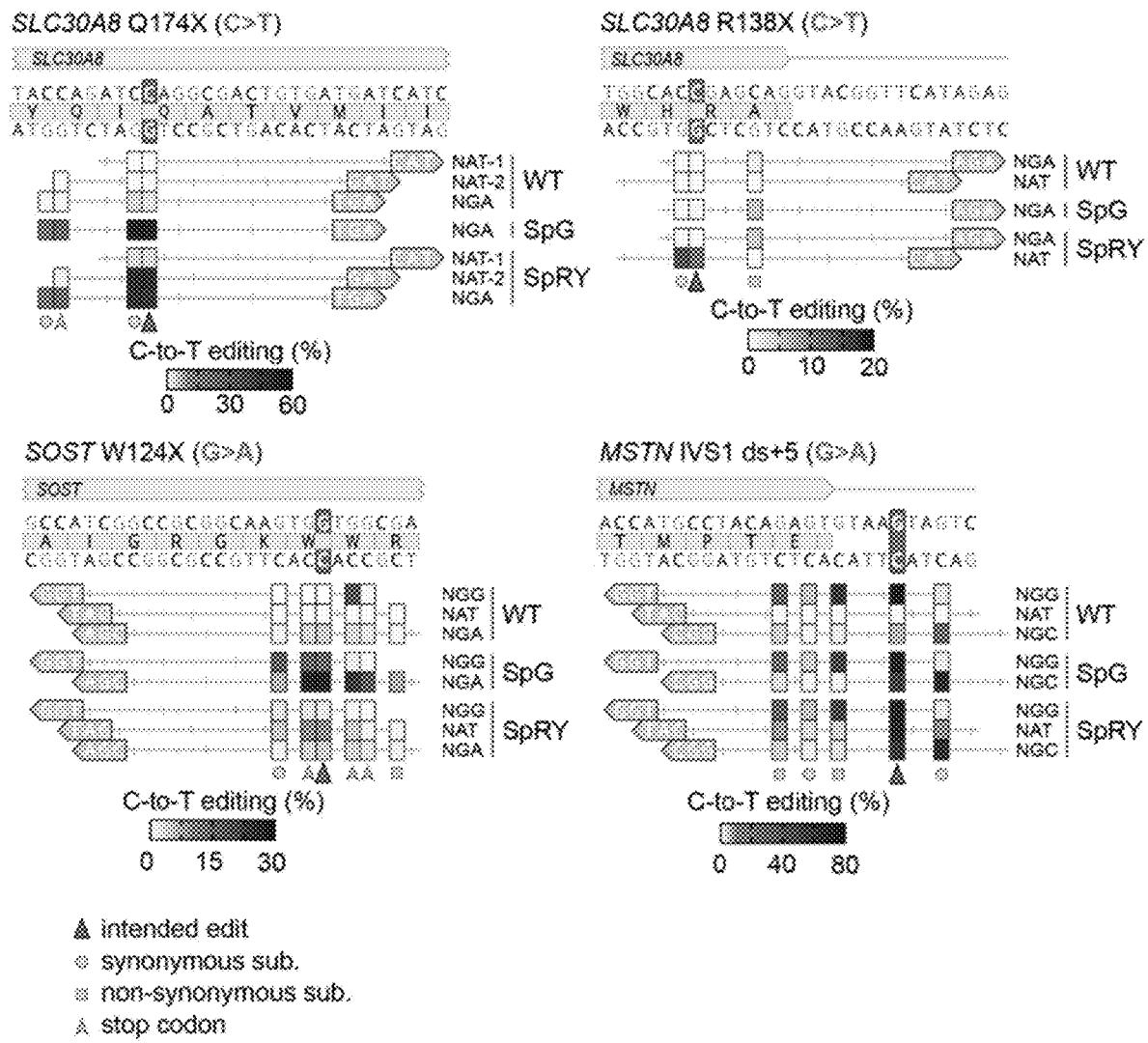
FIG. 4, continued

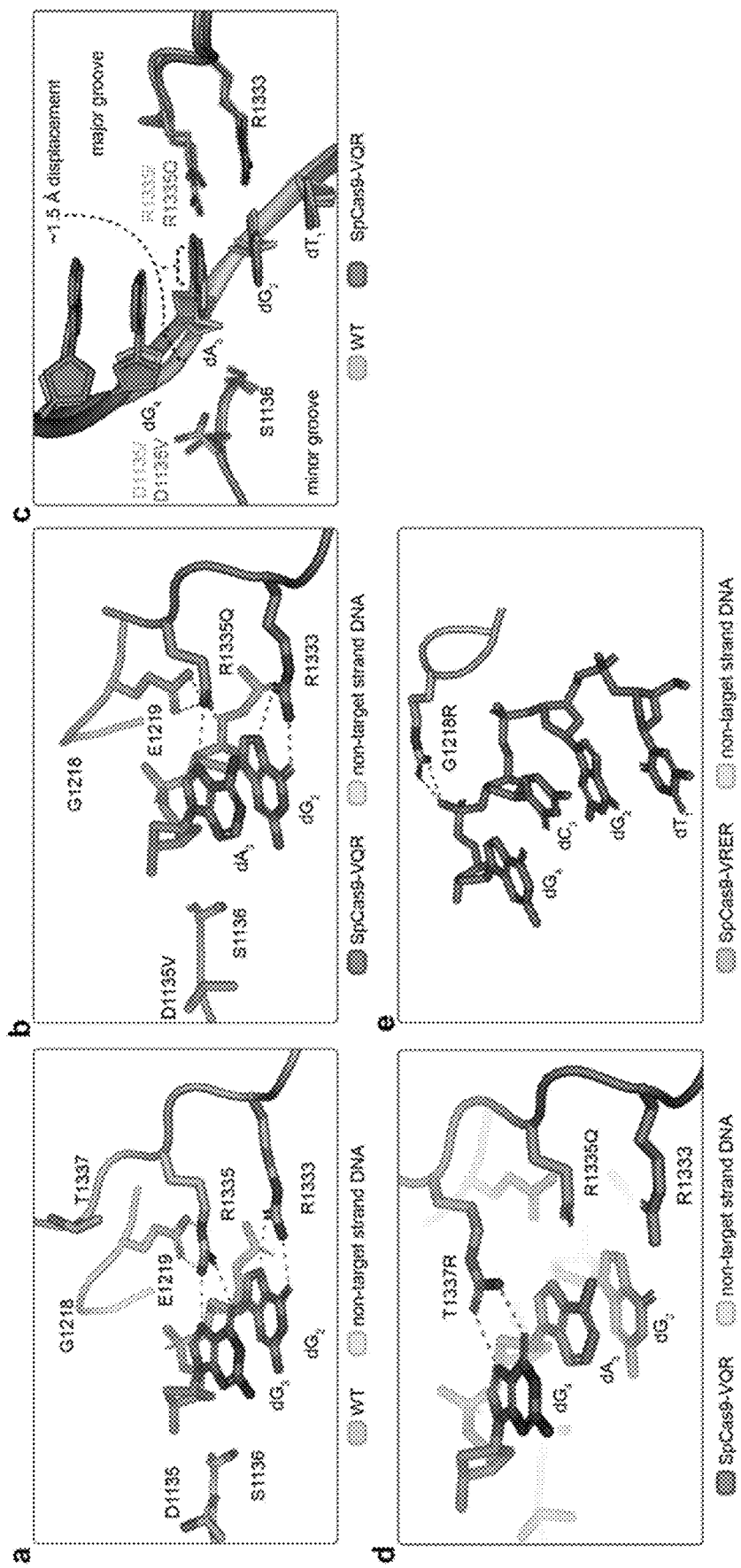
FIGs. 5A-E

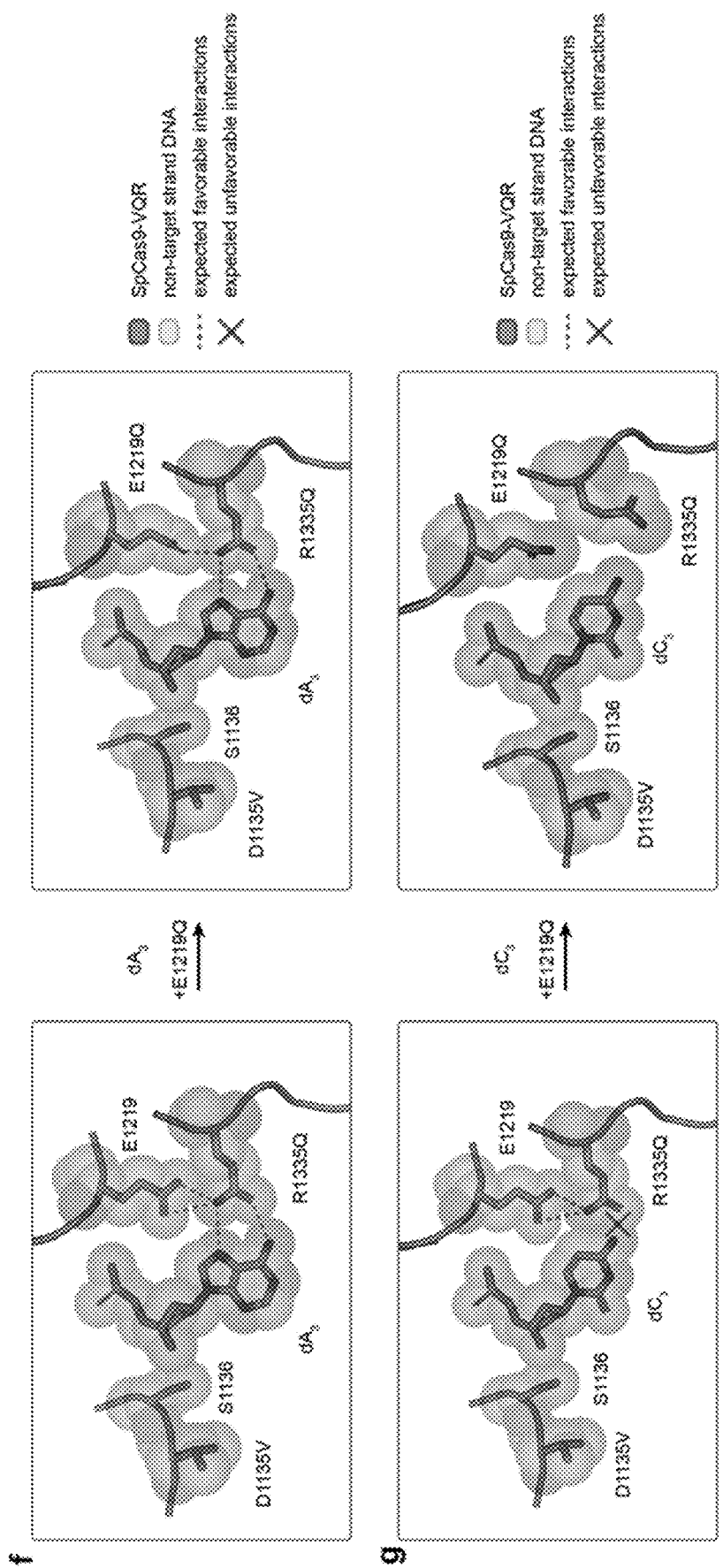
FIGs. 5F-G

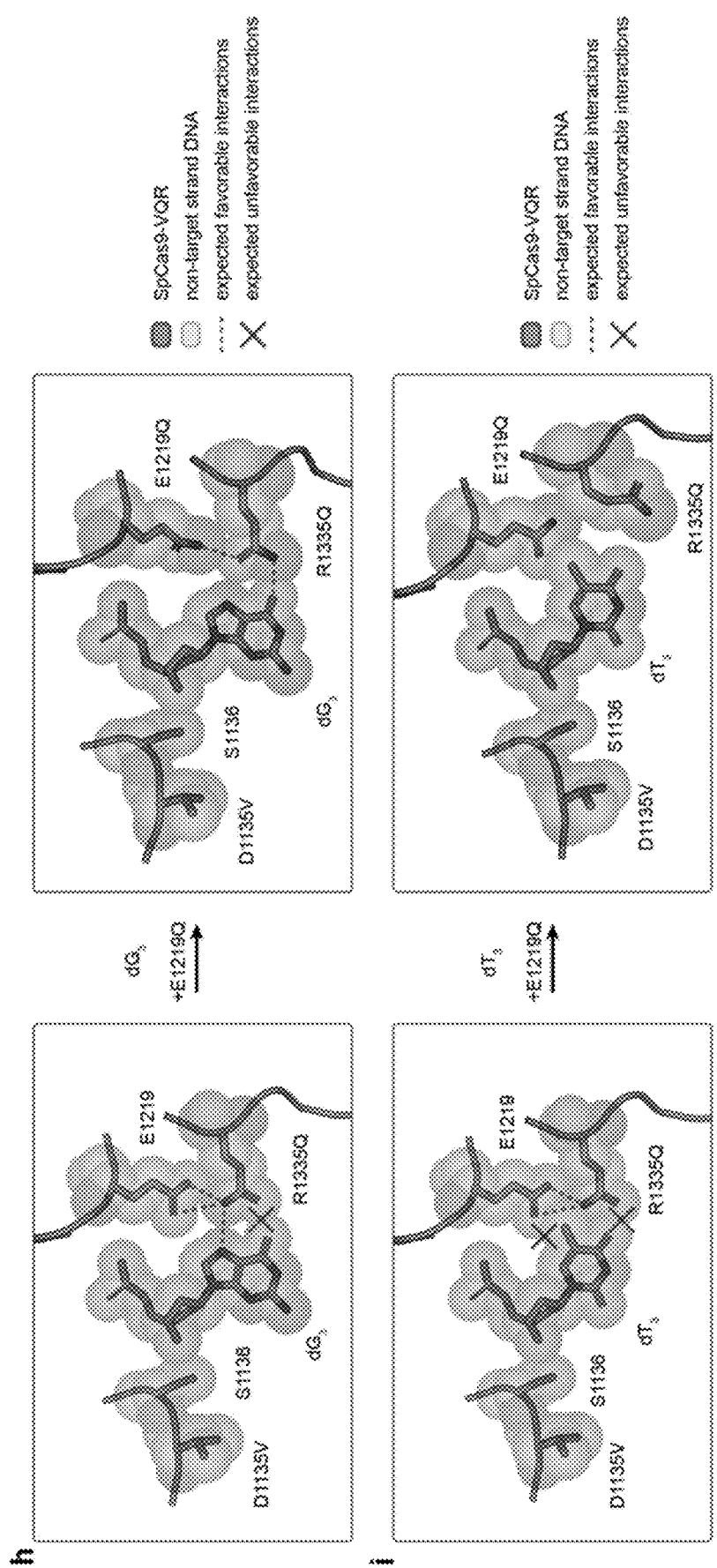
FIGs. 5H-I

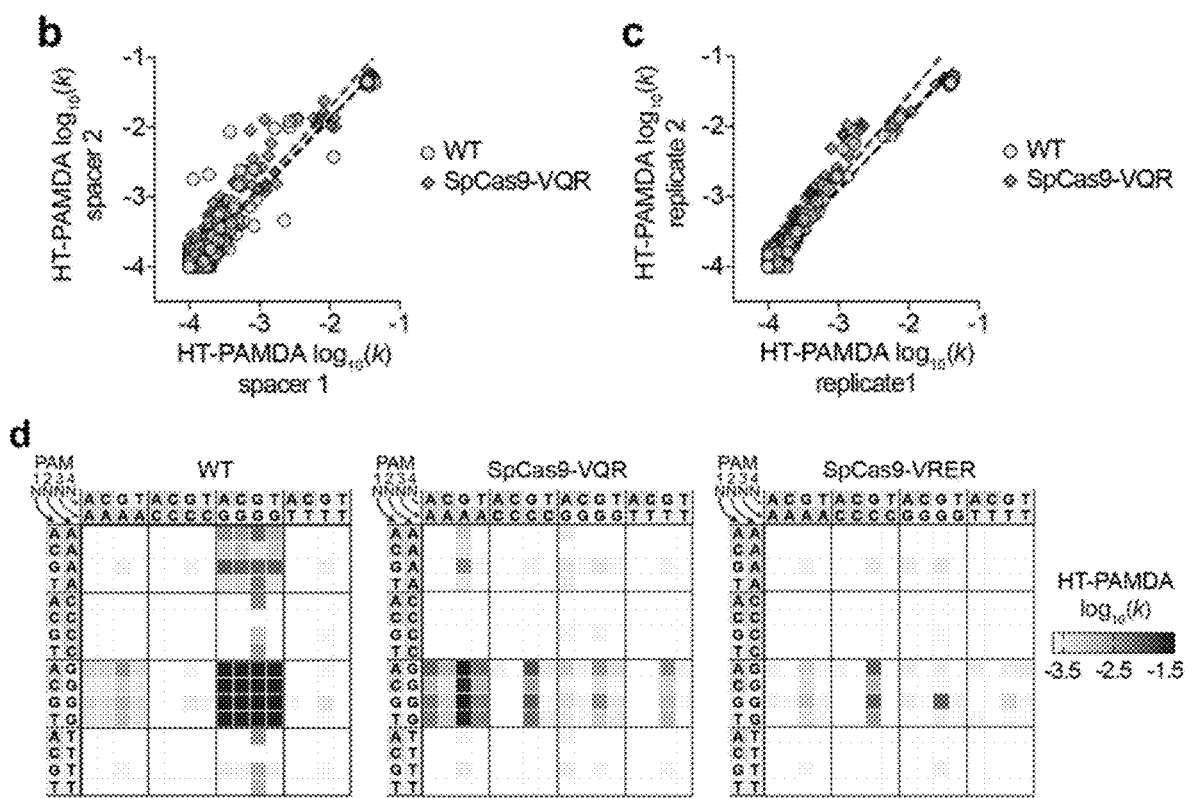
FIGs. 6B-D

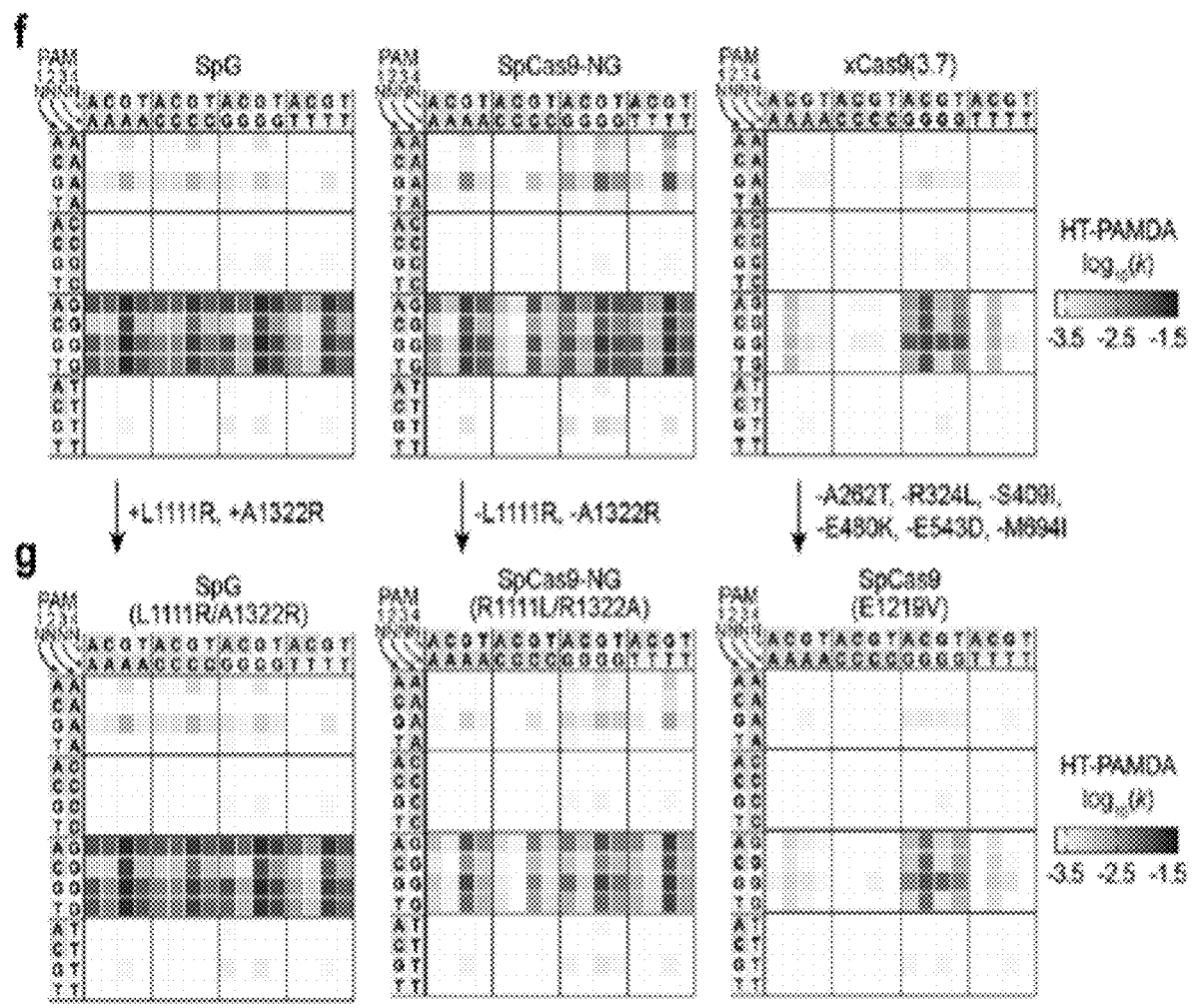
FIGs. 6F-G

| Construct | | | | | | # |
|---|---|---|---|---|---|---|
| | | SpCas9 | 3xFLAG | 2A | EGFP | 1 |
| | SV40 | SpCas9 | 3xFLAG | 2A | EGFP | 2 |
| | BP-SV40 | SpCas9 | 3xFLAG | 2A | EGFP | 3 |
| | Nuc | SpCas9 | 3xFLAG | 2A | EGFP | 4 |
| | (?) | SpCas9 | 3xFLAG | 2A | EGFP | 5 |
| | SpCas9 | SV40 | 3xFLAG | 2A | EGFP | 6 |
| | SpCas9 | BP-SV40 | 3xFLAG | 2A | EGFP | 7 |
| | SpCas9 | Nuc | 3xFLAG | 2A | EGFP | 8 |
| | SpCas9 | (?) | 3xFLAG | 2A | EGFP | 9 |
| BP-SV40 | SpCas9 | BP-SV40 | 3xFLAG | 2A | EGFP | 10 |
| SpCas9 | BP-SV40 | BP-SV40 | 3xFLAG | 2A | EGFP | 11 |
| Myc | SpCas9 | SV40 | Nuc | 3xFLAG 2A | EGFP | 12 |
| Myc | SpCas9 | SV40 | Nuc | 2A | EGFP | 13 |

FIG. 7A

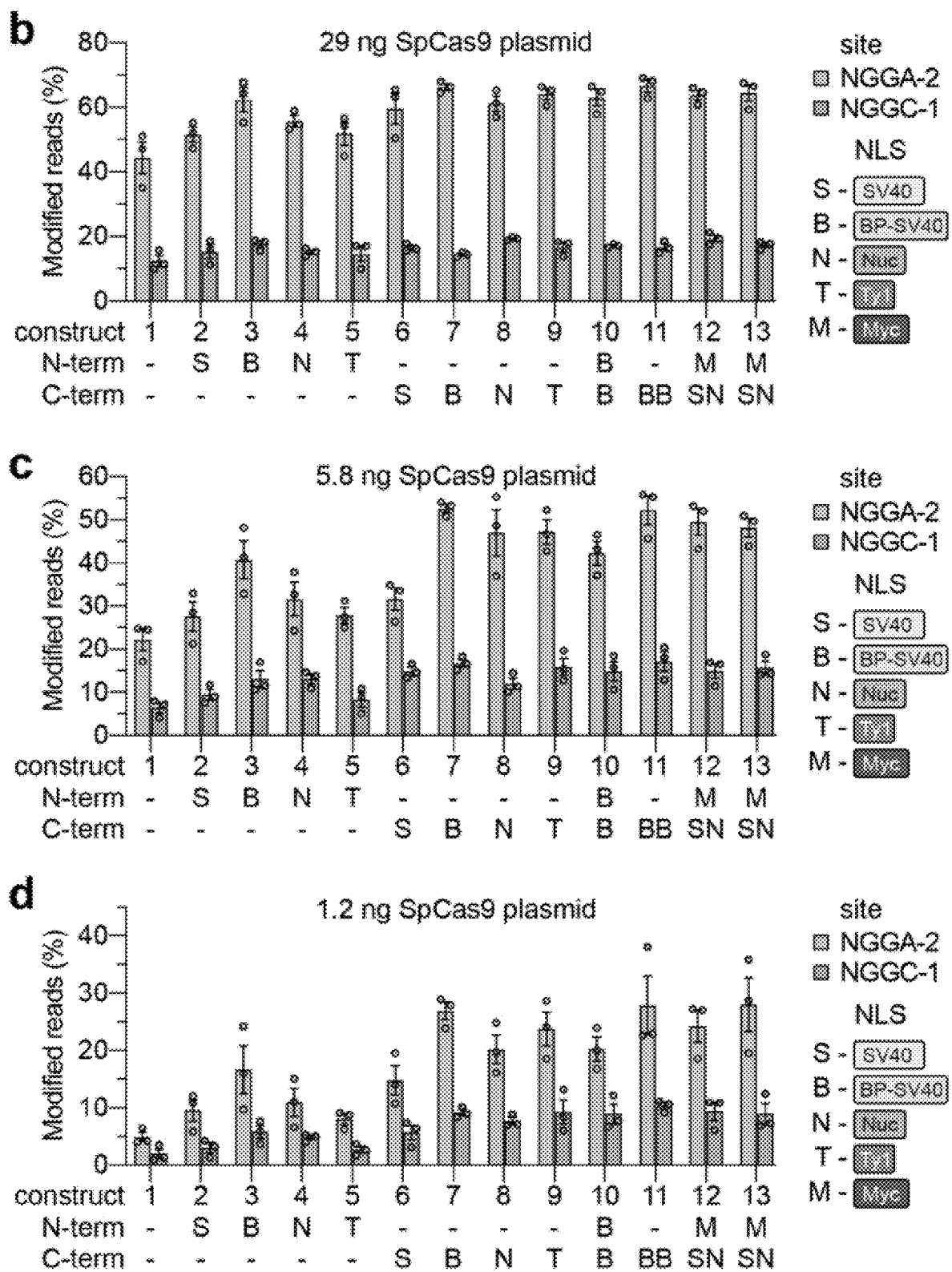
FIGs. 7B-D

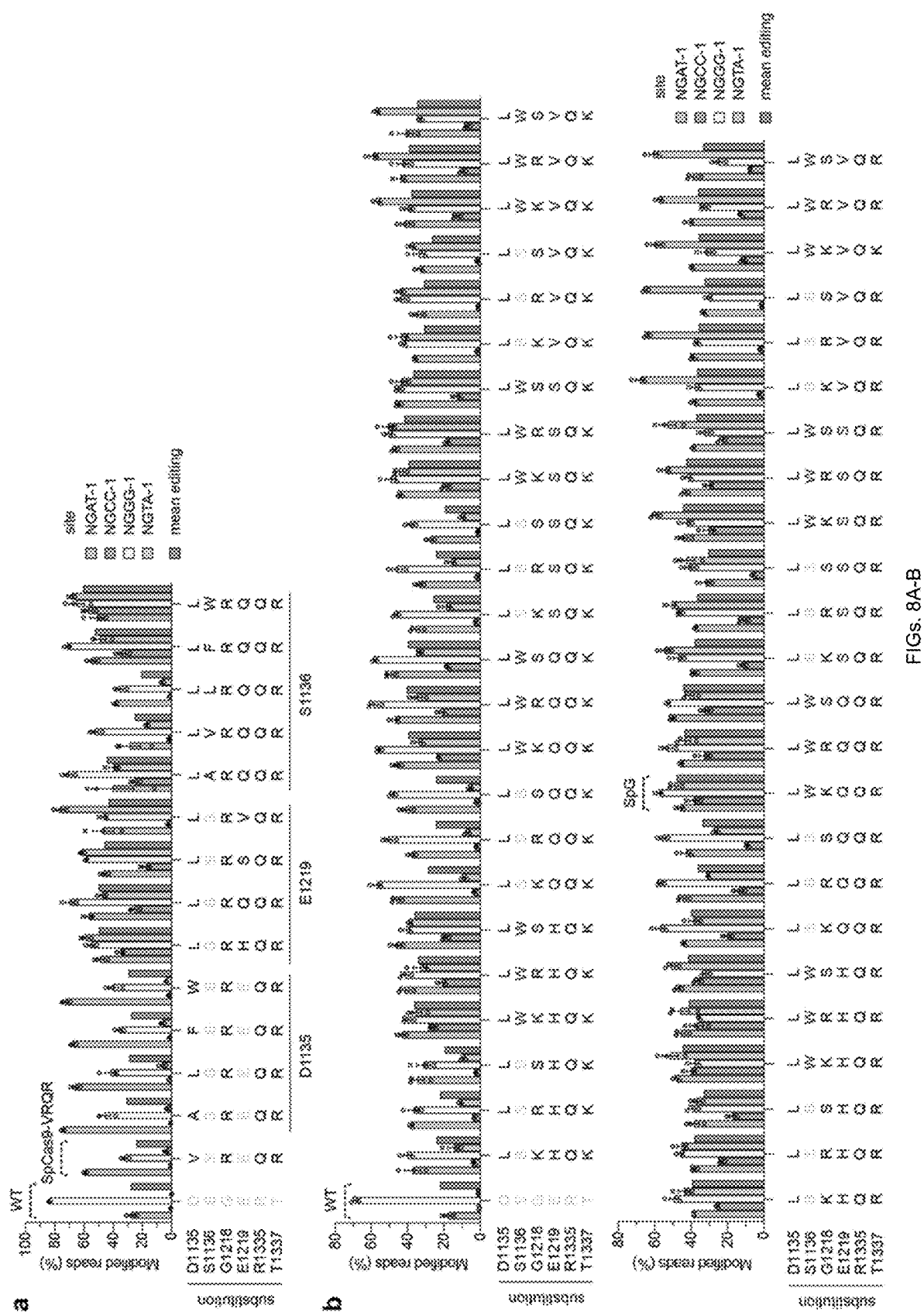
FIGs. 8A-B

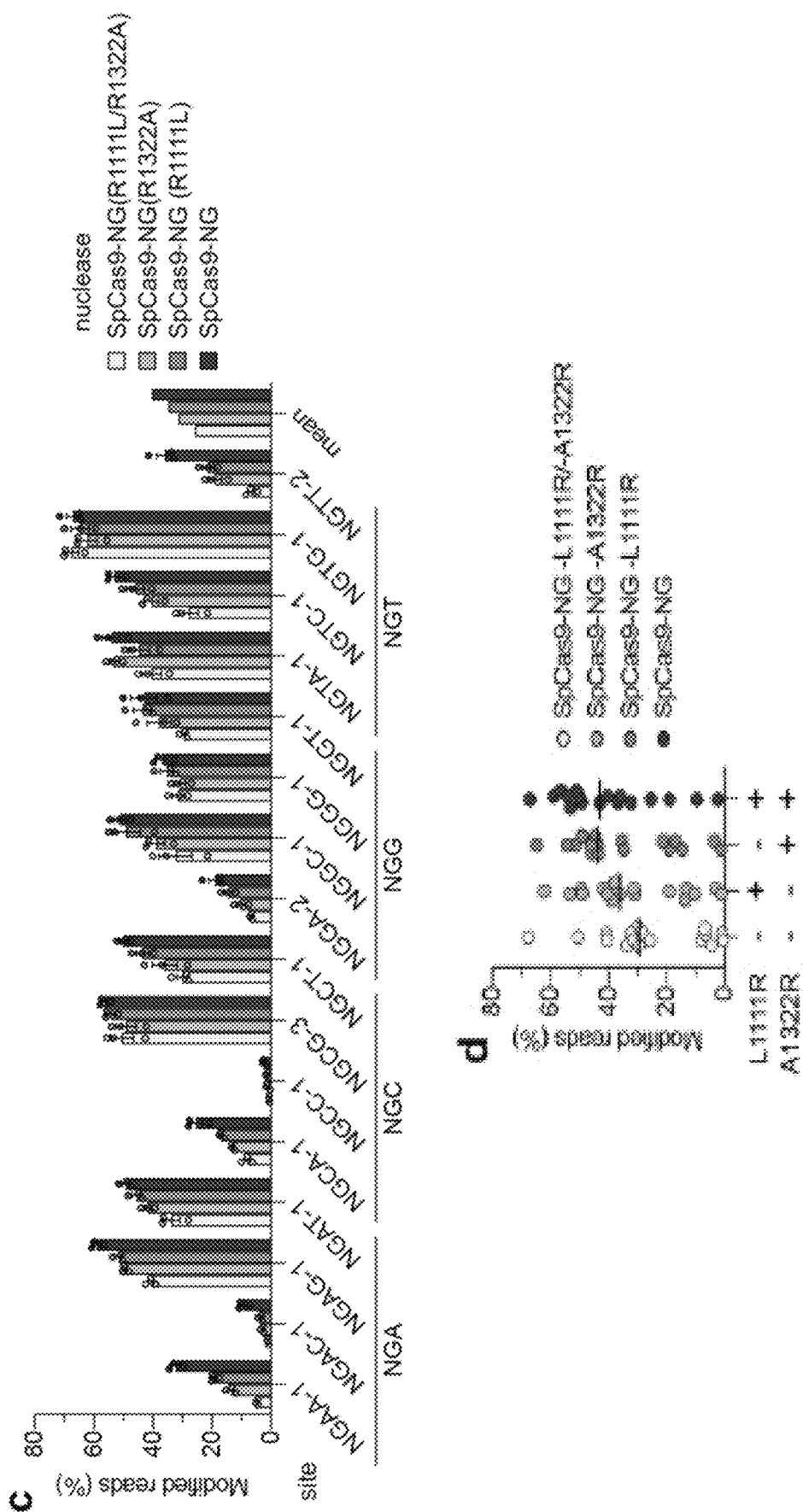
FIGs. 8C-D

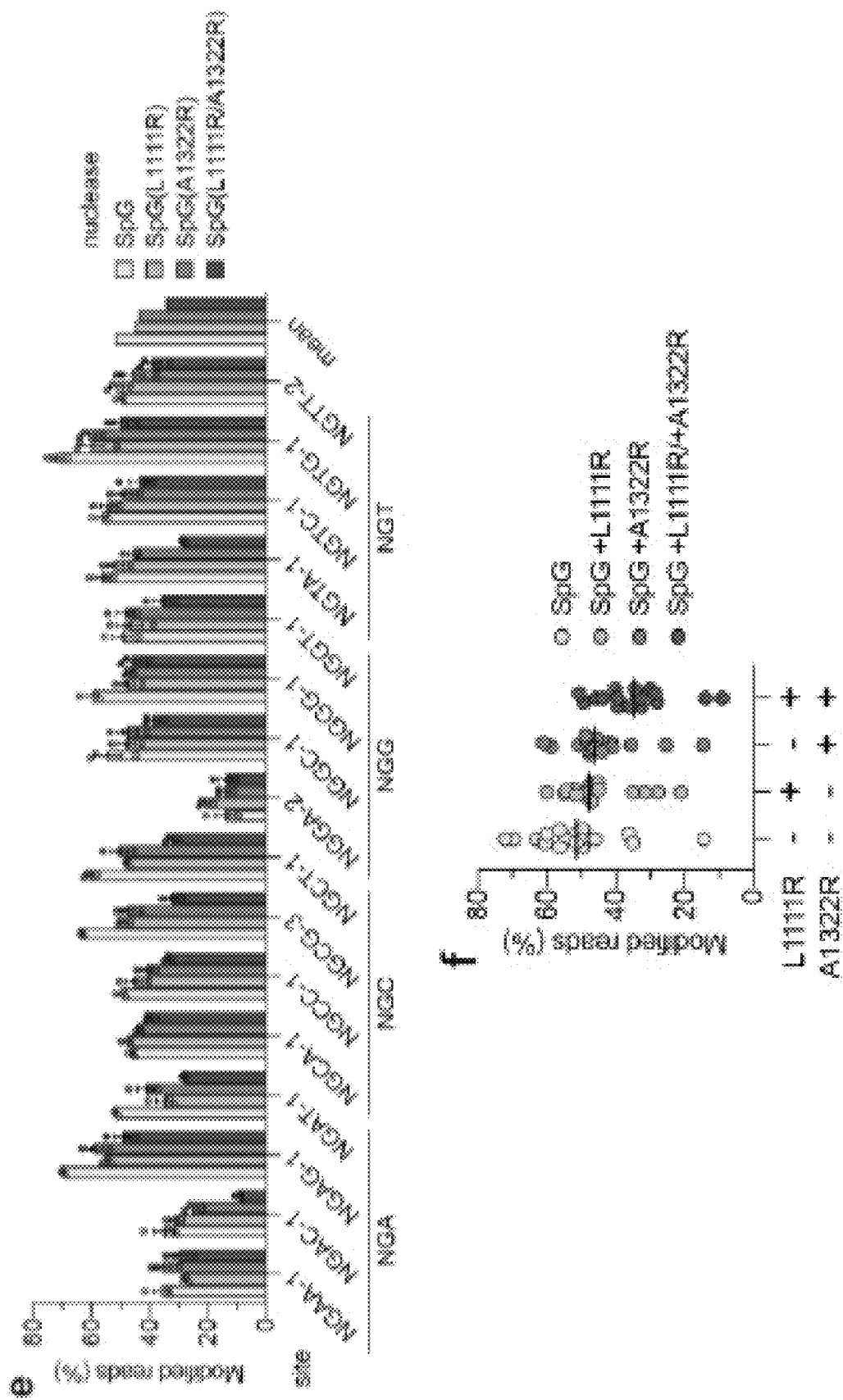
FIGs. 8E-F

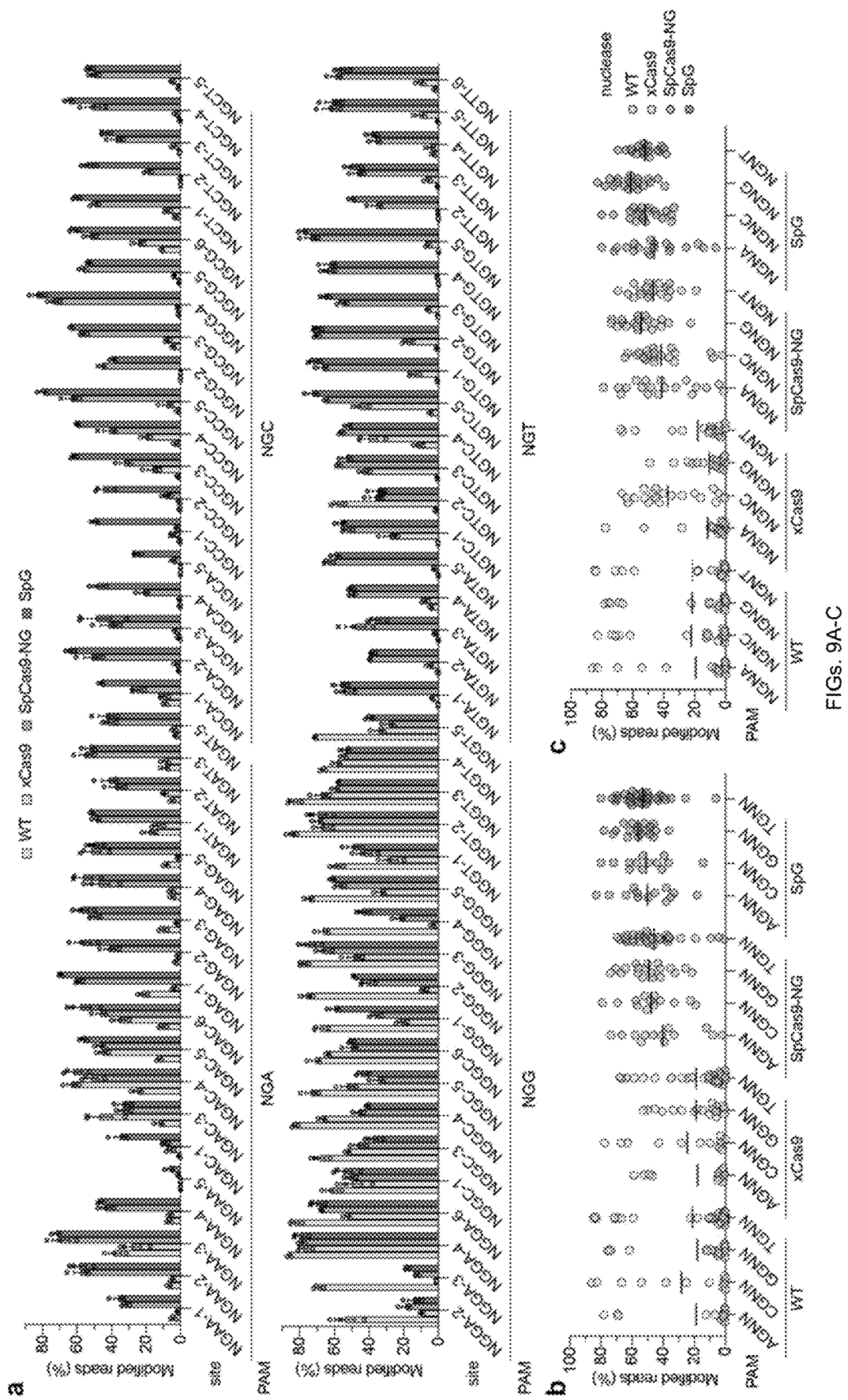
FIGs. 9A-C

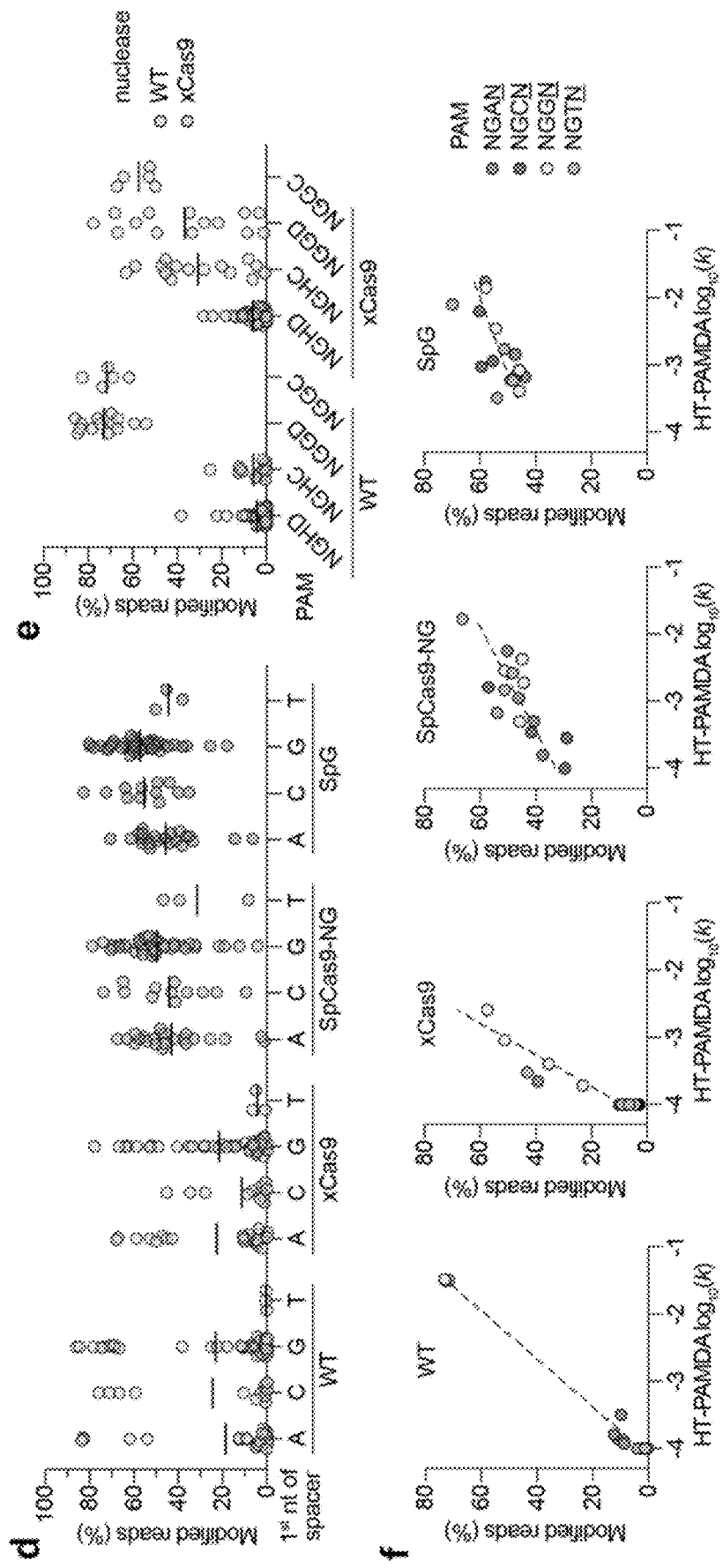
FIGs. 9D-F

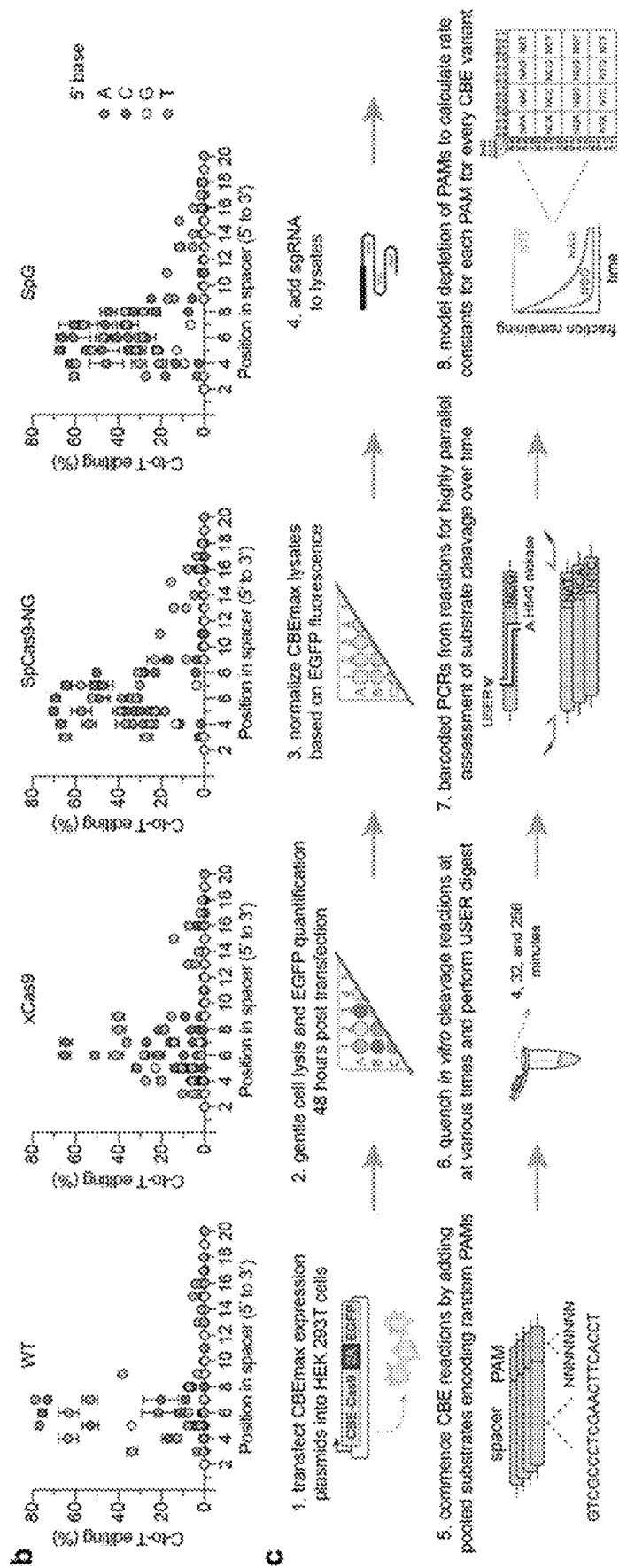
FIGs. 10B-C

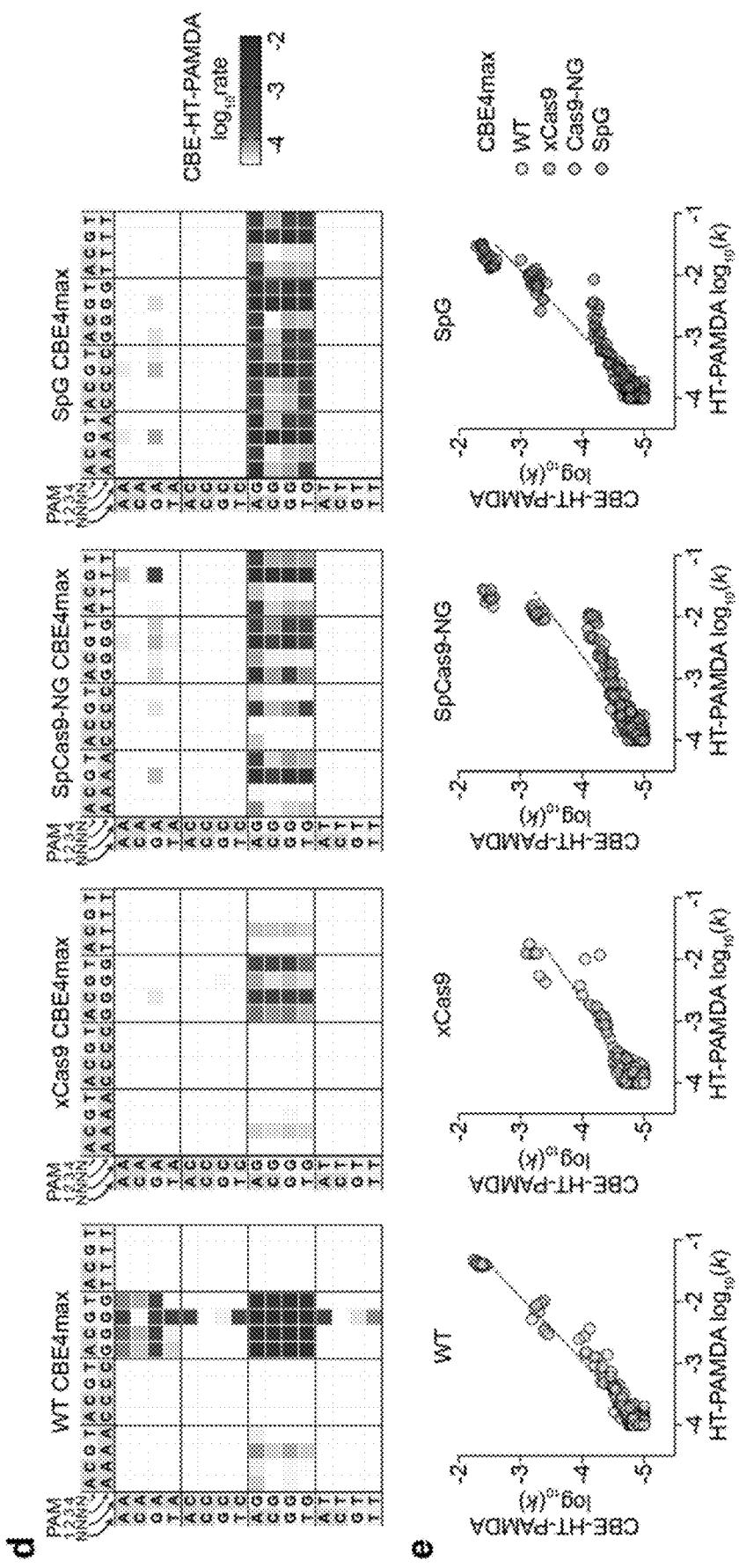
FIGs. 10D-E

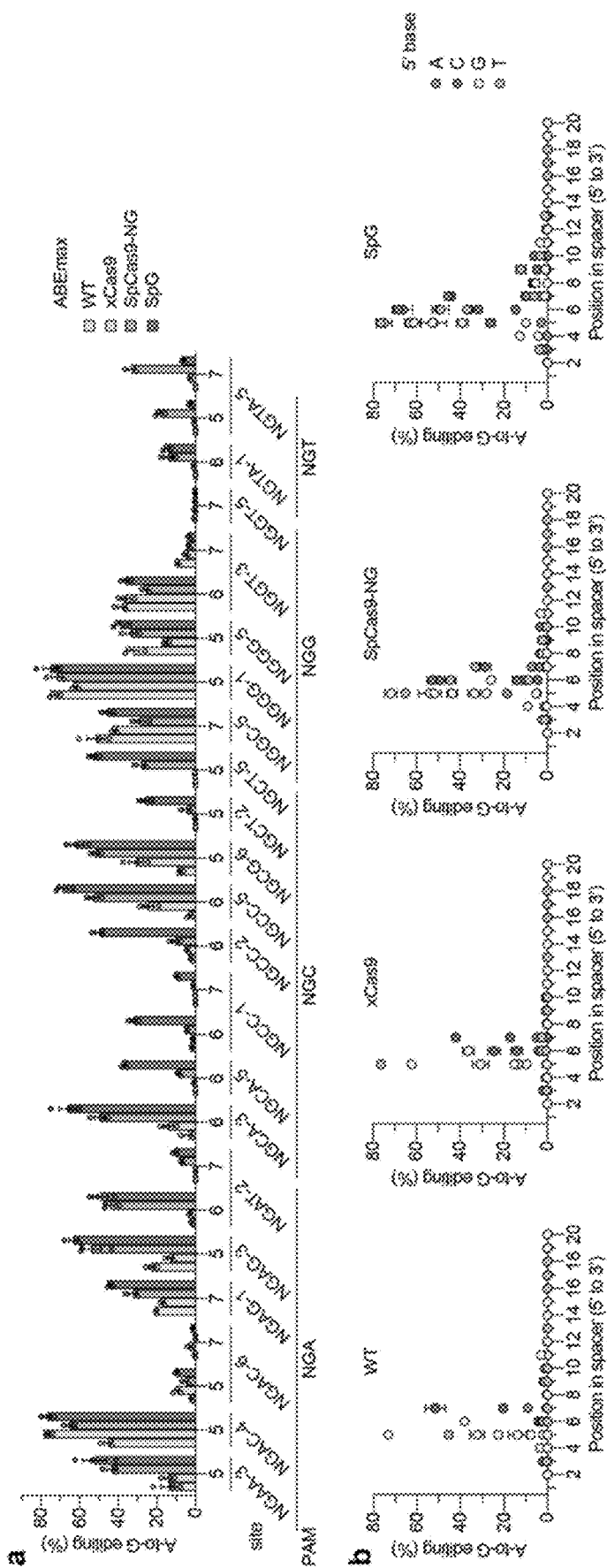
FIGs. 11A-B

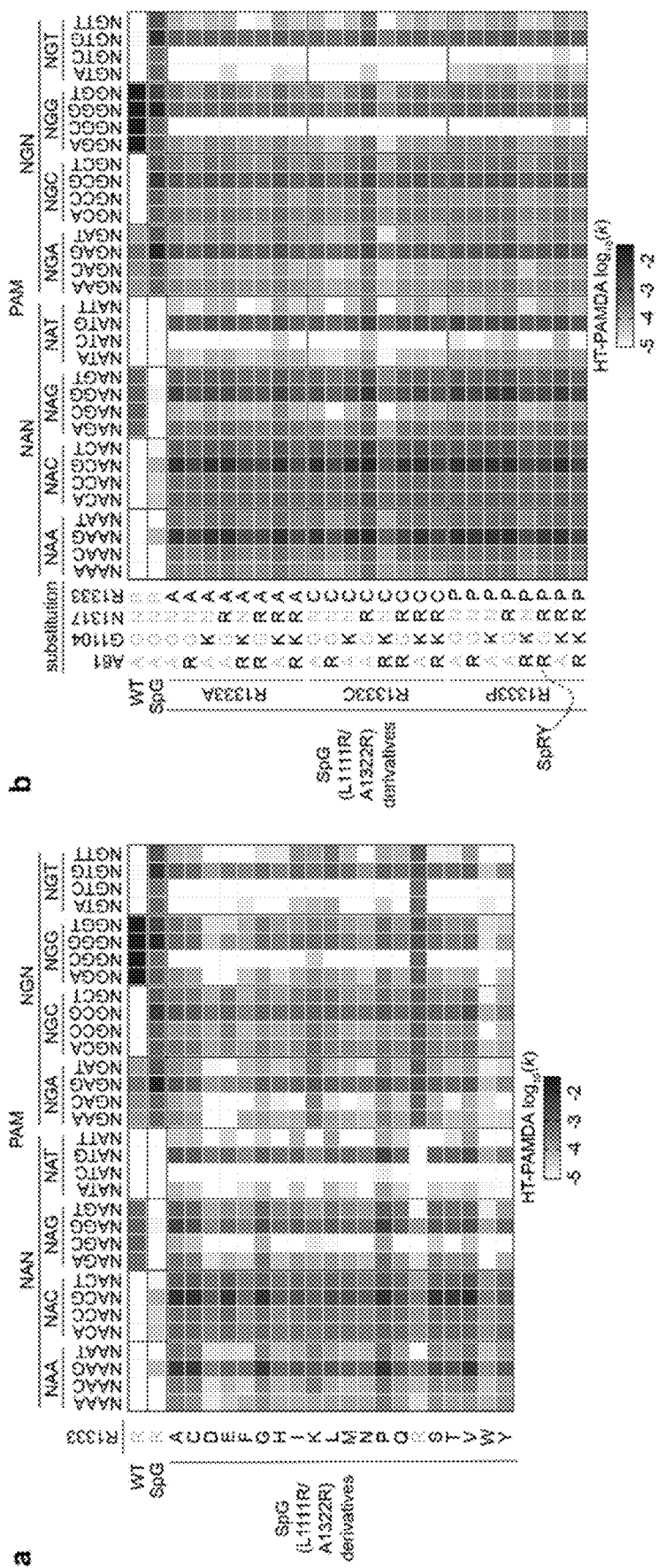
FIGs. 12A-B

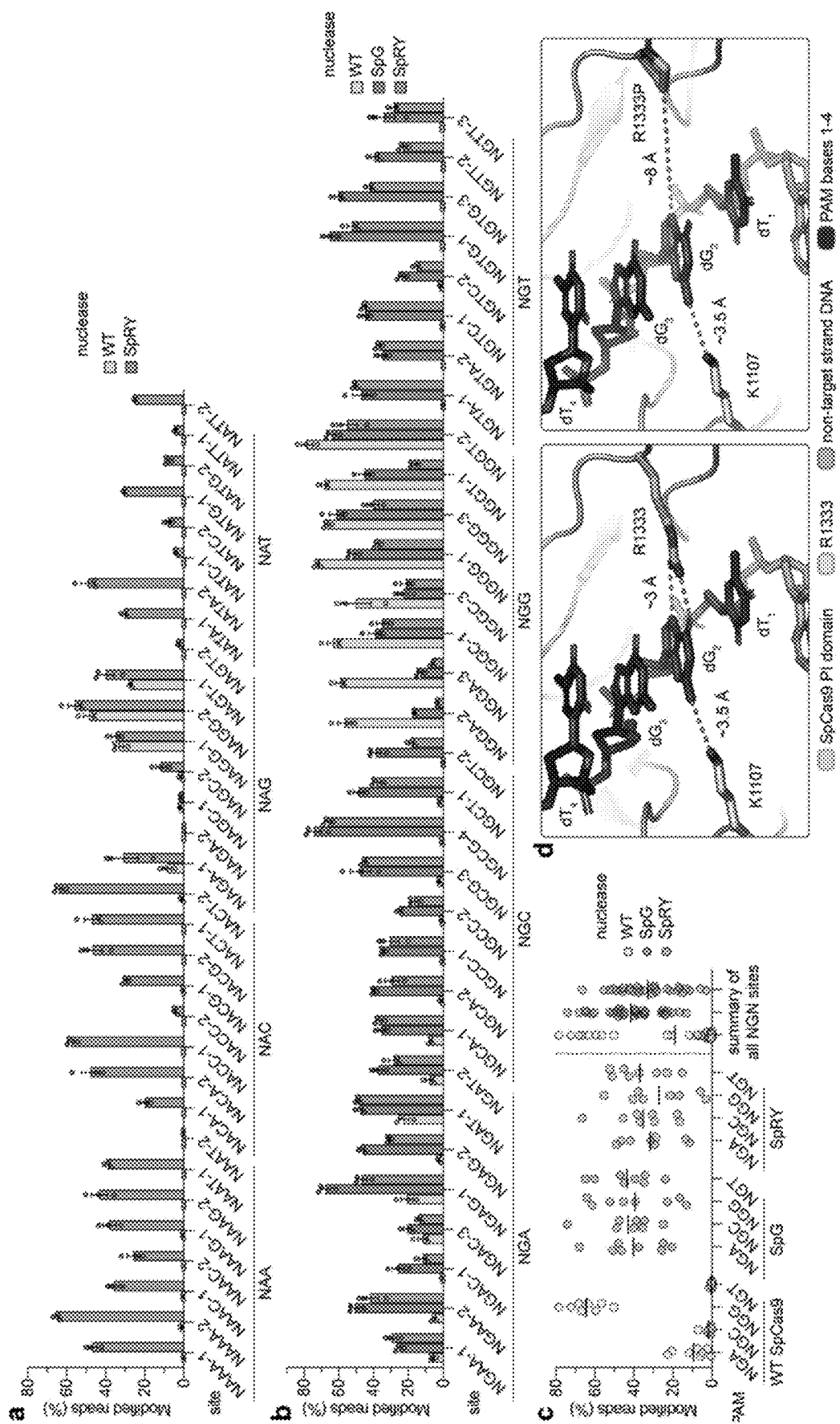
FIGs. 13A-D

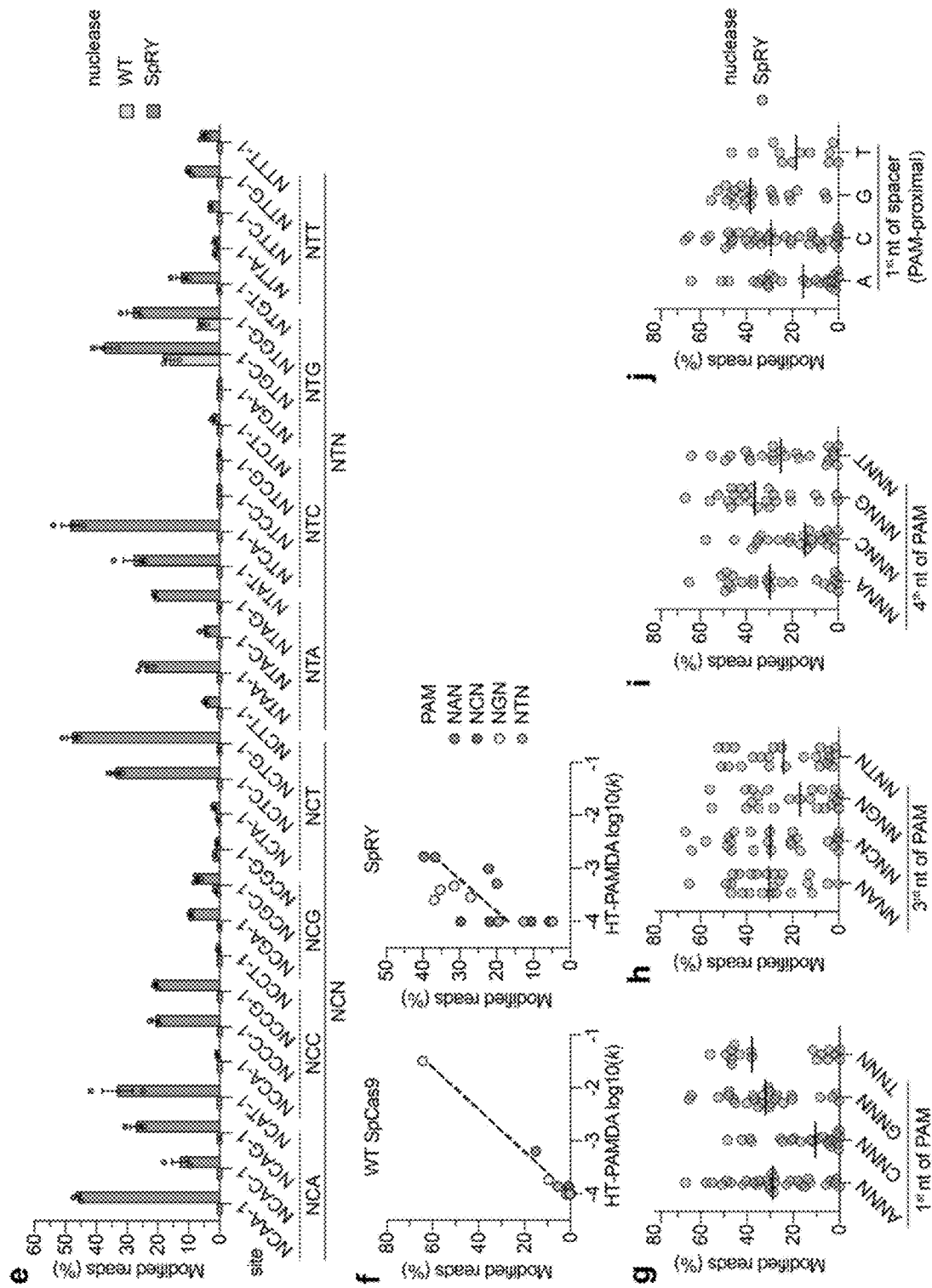
FIGs. 13E-J

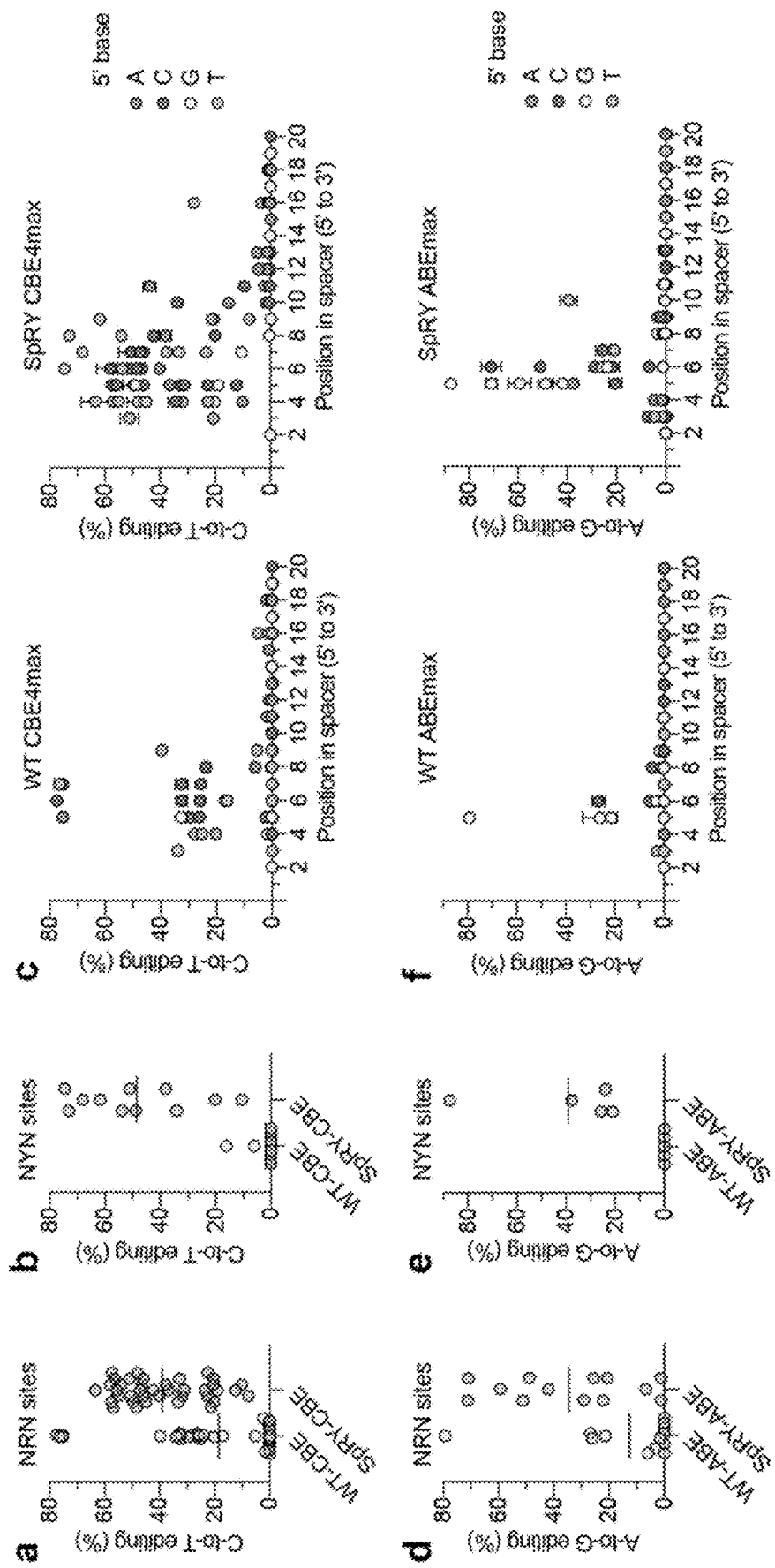
FIGs. 14A-F

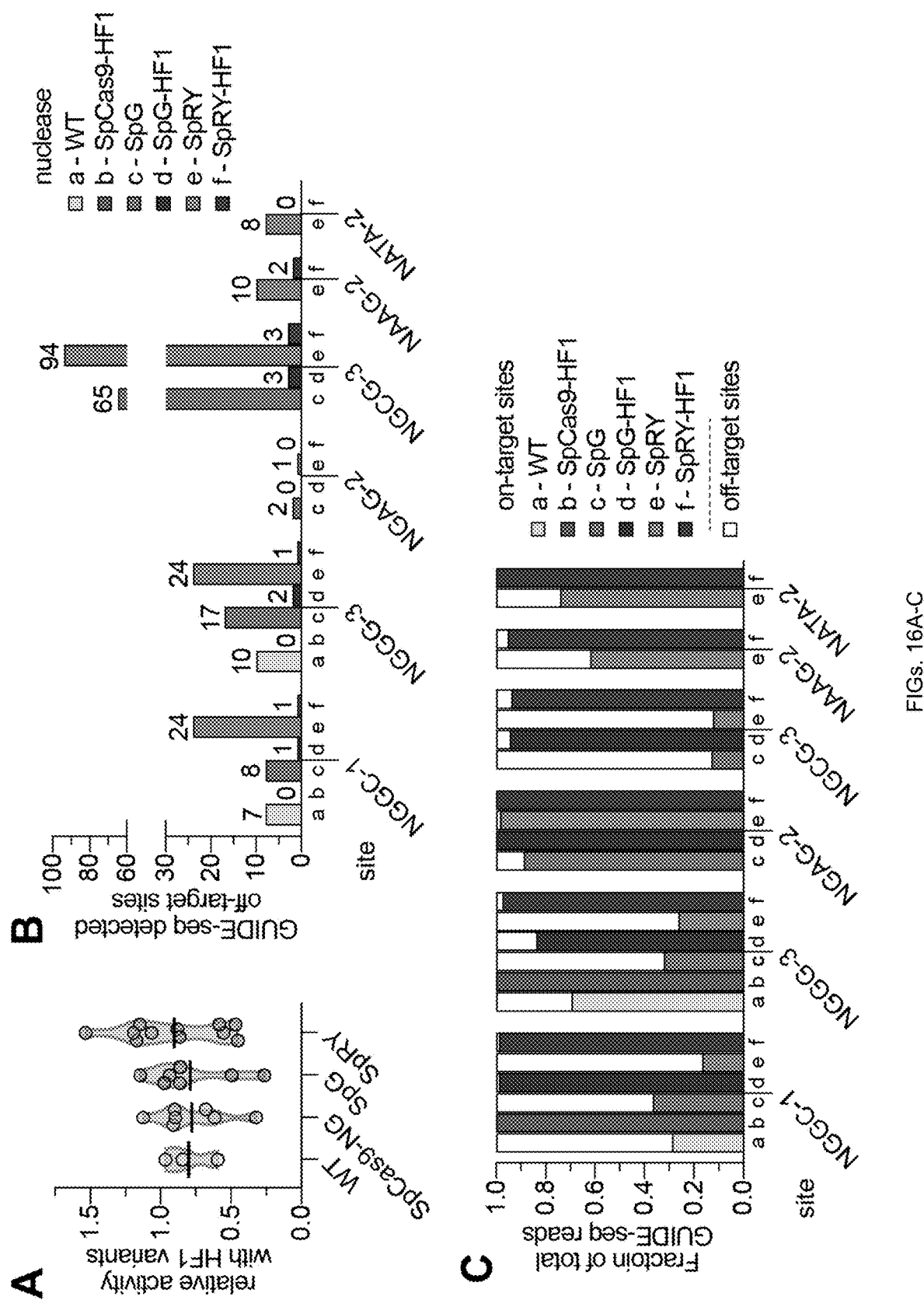
FIGs. 16A-C

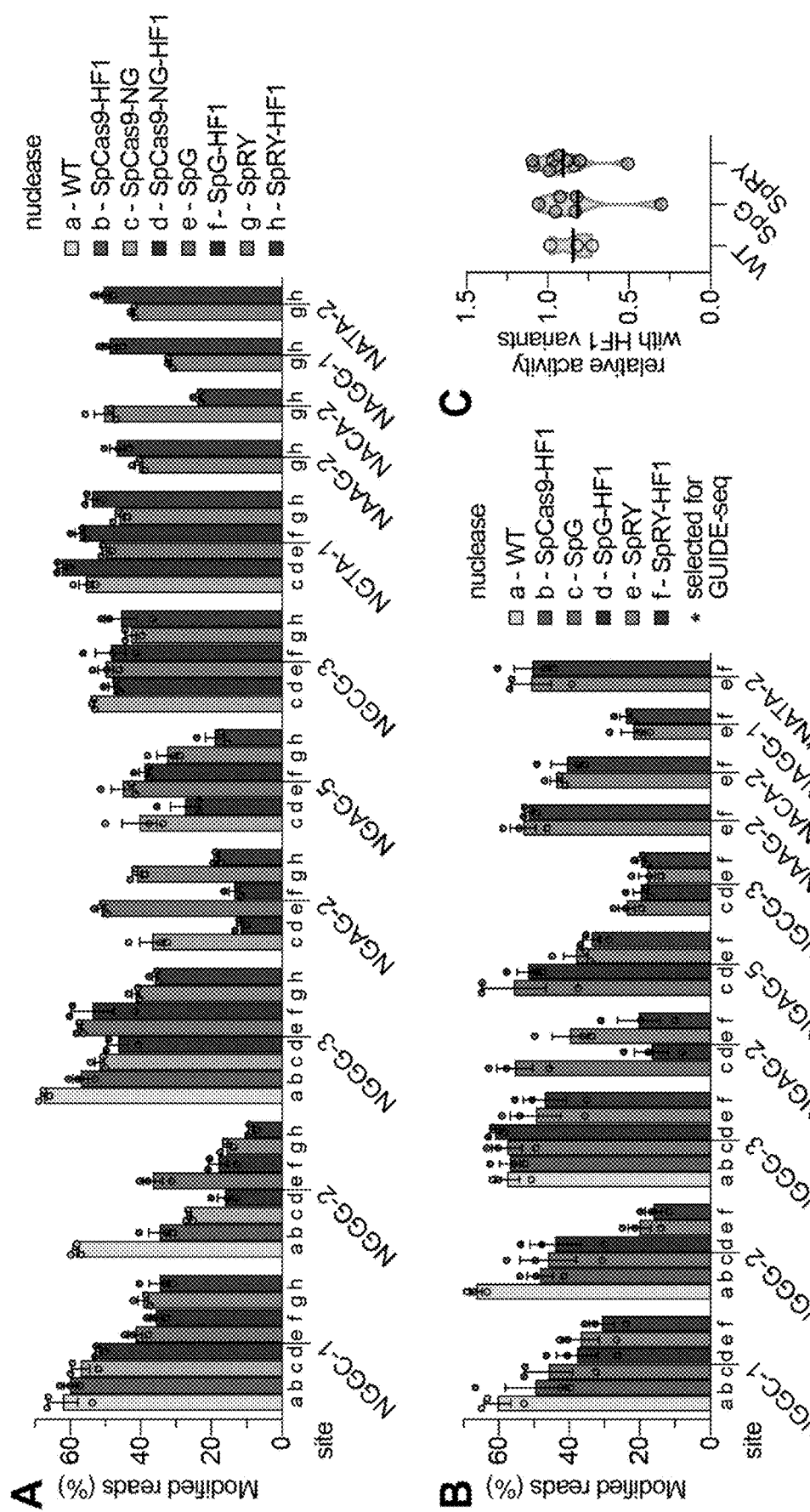
FIGs. 17A-C

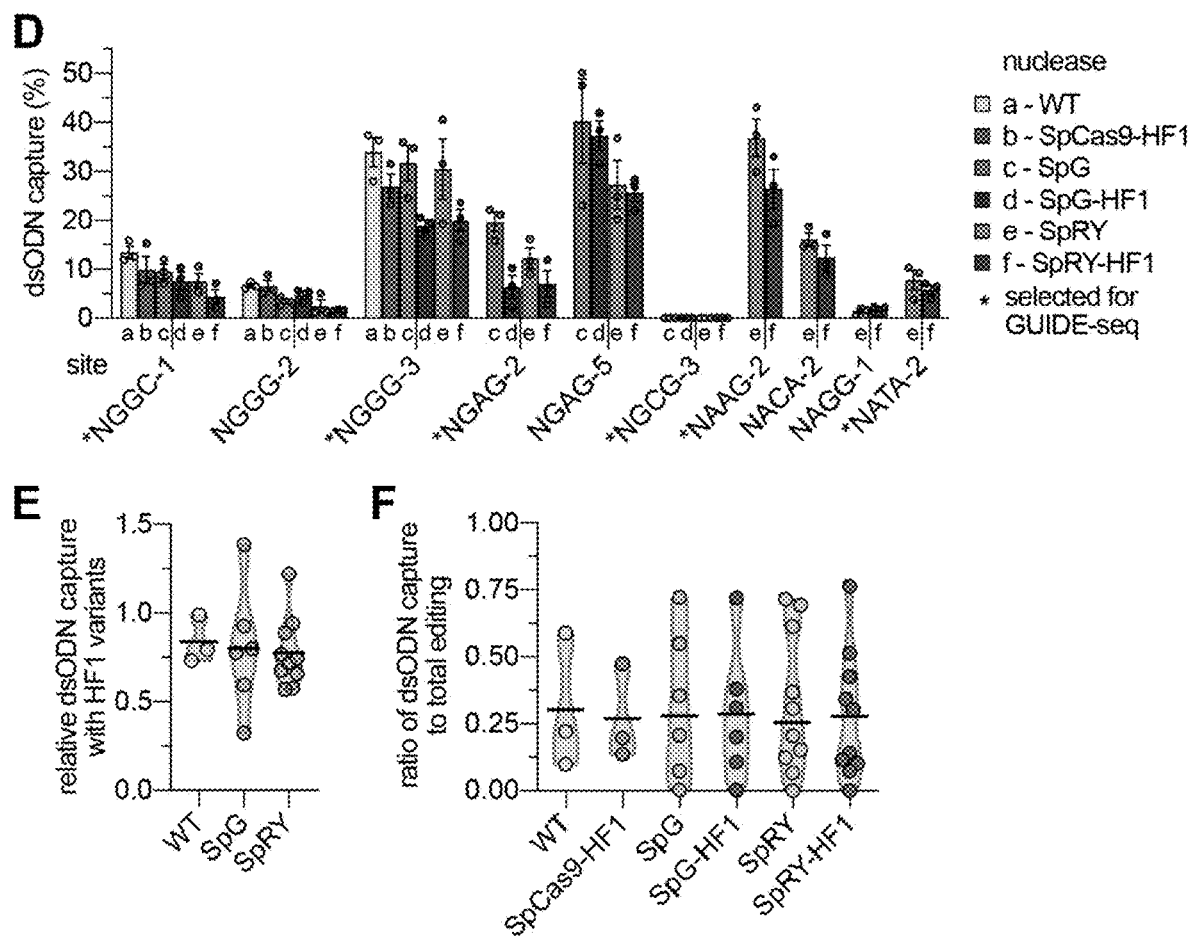
FIGs. 17D-F

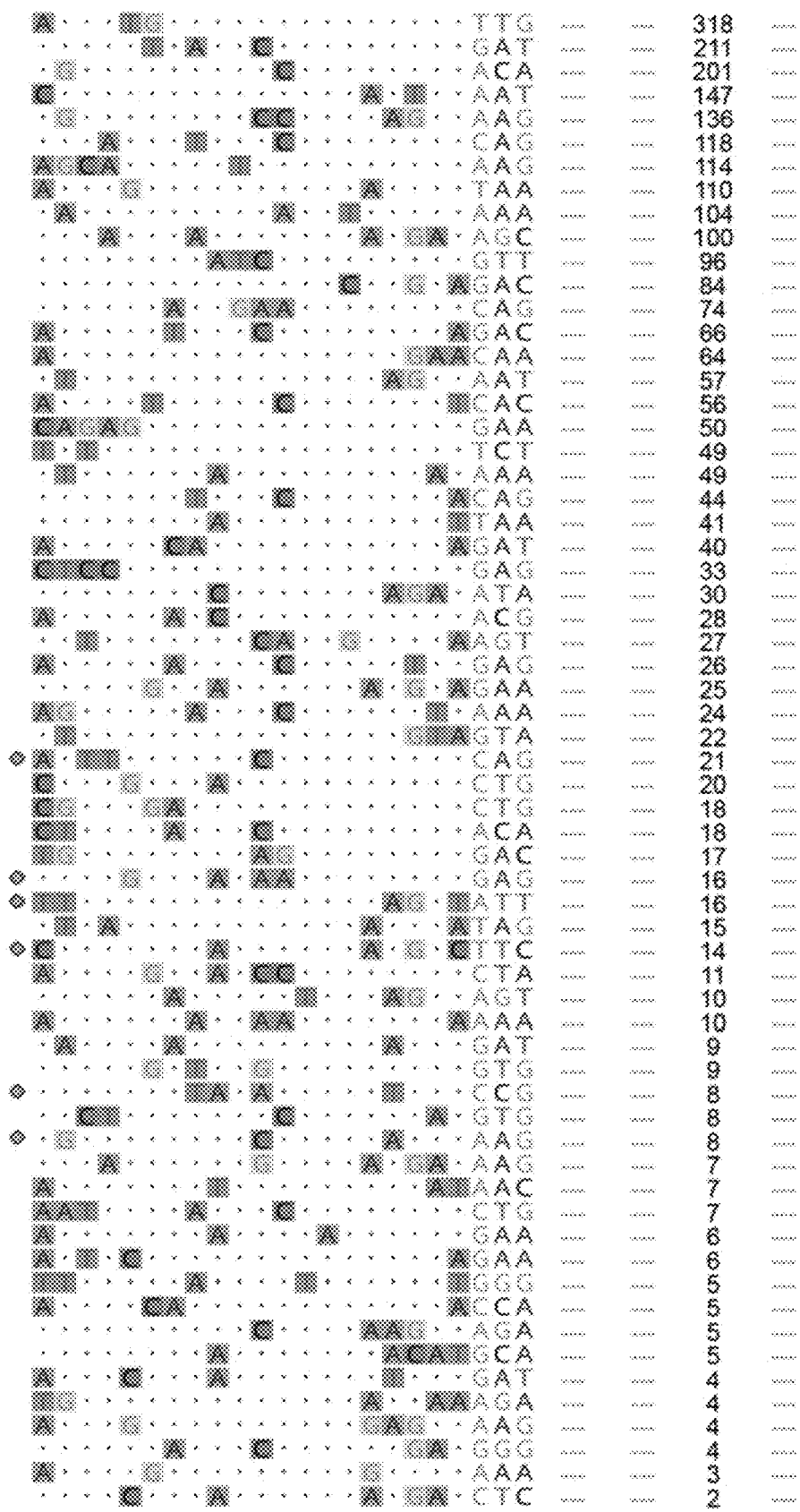
FIG. 18B, continued

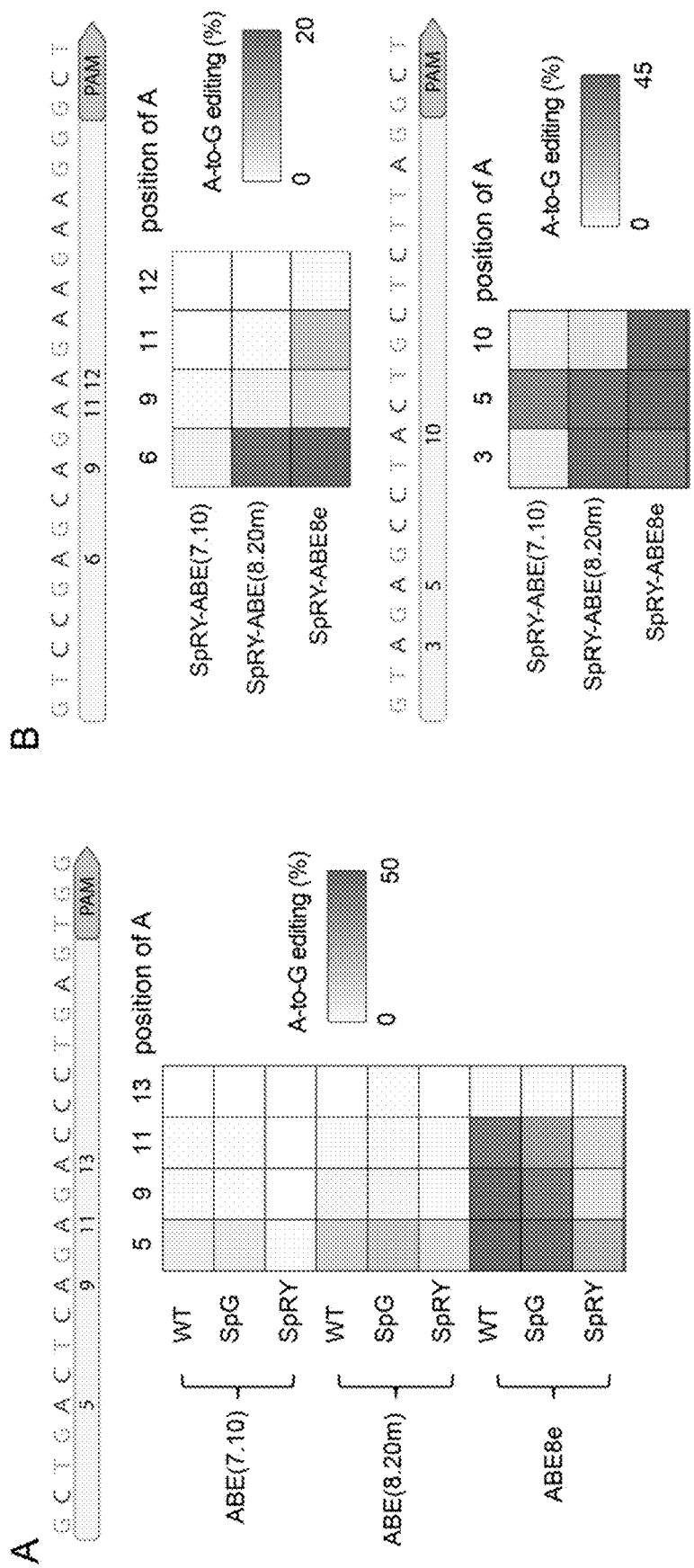
FIGs. 19A-B

SEQUENCE LISTING

```
<160> NUMBER OF SEQ ID NOS: 295

<210> SEQ ID NO 1
<211> LENGTH: 1368
<212> TYPE: PRT
<213> ORGANISM: Streptococcus pyogenes

<400> SEQUENCE: 1

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125
```

```
His Glu Lys Tyr Pro Thr Ile Tyr His Leu Arg Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
530                 535                 540
```

```
Lys Lys Ala Ile Val Asp Leu Leu Phe Lys Thr Asn Arg Lys Val Thr
545                 550                 555                 560

Val Lys Gln Leu Lys Glu Asp Tyr Phe Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
                770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
                835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
```

```
                965                 970                 975
Glu Ile Asn Asn Tyr His His Ala His Asp Ala Tyr Leu Asn Ala Val
                    980                 985                 990
Val Gly Thr Ala Leu Ile Lys Lys Tyr Pro Lys Leu Glu Ser Glu Phe
                    995                 1000                1005
Val Tyr Gly Asp Tyr Lys Val Tyr Asp Val Arg Lys Met Ile Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Asp Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Leu Gly Ile Thr Ile Met Glu Arg Ser Ser
    1160                1165                1170
Phe Glu Lys Asn Pro Ile Asp Phe Leu Glu Ala Lys Gly Tyr Lys
    1175                1180                1185
Glu Val Lys Lys Asp Leu Ile Ile Lys Leu Pro Lys Tyr Ser Leu
    1190                1195                1200
Phe Glu Leu Glu Asn Gly Arg Lys Arg Met Leu Ala Ser Ala Gly
    1205                1210                1215
Glu Leu Gln Lys Gly Asn Glu Leu Ala Leu Pro Ser Lys Tyr Val
    1220                1225                1230
Asn Phe Leu Tyr Leu Ala Ser His Tyr Glu Lys Leu Lys Gly Ser
    1235                1240                1245
Pro Glu Asp Asn Glu Gln Lys Gln Leu Phe Val Glu Gln His Lys
    1250                1255                1260
His Tyr Leu Asp Glu Ile Ile Glu Gln Ile Ser Glu Phe Ser Lys
    1265                1270                1275
Arg Val Ile Leu Ala Asp Ala Asn Leu Asp Lys Val Leu Ser Ala
    1280                1285                1290
Tyr Asn Lys His Arg Asp Lys Pro Ile Arg Glu Gln Ala Glu Asn
    1295                1300                1305
Ile Ile His Leu Phe Thr Leu Thr Asn Leu Gly Ala Pro Ala Ala
    1310                1315                1320
Phe Lys Tyr Phe Asp Thr Thr Ile Asp Arg Lys Arg Tyr Thr Ser
    1325                1330                1335
Thr Lys Glu Val Leu Asp Ala Thr Leu Ile His Gln Ser Ile Thr
    1340                1345                1350
Gly Leu Tyr Glu Thr Arg Ile Asp Leu Ser Gln Leu Gly Gly Asp
    1355                1360                1365
```

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Gly Ser
1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Gly Gly Ser
1               5

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gcggtatcat tgcagcactg                                              20

<210> SEQ ID NO 5
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ttctaatacg actcactata gcggtatcat tgcagcactg gttttagagc taga         54

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gctcttgccc ggcgtcaata                                              20

<210> SEQ ID NO 7
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ttctaatacg actcactata gctcttgccc ggcgtcaata gttttagagc taga      54

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ggccaccact tcaagaactc                                            20

<210> SEQ ID NO 9
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ttctaatacg actcactata ggccaccact tcaagaactc gttttagagc taga      54

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gatacctaca gcgtgagcta                                            20

<210> SEQ ID NO 11
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ttctaatacg actcactata gatacctaca gcgtgagcta gttttagagc taga      54

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ggtaactggc ttcagcagag                                            20

<210> SEQ ID NO 13
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ttctaatacg actcactata ggtaactggc ttcagcagag gttttagagc taga      54

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gctcacgctg taggtatctc                                                 20

<210> SEQ ID NO 15
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ttctaatacg actcactata gctcacgctg taggtatctc gttttagagc taga           54

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gatcgttggg aaccggagct                                                 20

<210> SEQ ID NO 17
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ttctaatacg actcactata gatcgttggg aaccggagct gttttagagc taga           54

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gcgaggtatg taggcggtgc                                                 20

<210> SEQ ID NO 19
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ttctaatacg actcactata gcgaggtatg taggcggtgc gttttagagc taga           54

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gggatcatgt aactcgcctt                                                   20

<210> SEQ ID NO 21
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ttctaatacg actcactata gggatcatgt aactcgcctt gttttagagc taga             54

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggtaacagga ttagcagagc                                                   20

<210> SEQ ID NO 23
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ttctaatacg actcactata ggtaacagga ttagcagagc gttttagagc taga             54

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ggaaccggag ctgaatgaag                                                   20

<210> SEQ ID NO 25
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ttctaatacg actcactata ggaaccggag ctgaatgaag gttttagagc taga             54

```
<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ggccccagtg ctgcaatgat                                                     20

<210> SEQ ID NO 27
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ttctaatacg actcactata ggccccagtg ctgcaatgat gttttagagc taga              54

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gcaatgatac cgcgagaccc                                                     20

<210> SEQ ID NO 29
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ttctaatacg actcactata gcaatgatac cgcgagaccc gttttagagc taga              54

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gataactacg atacgggagg                                                     20

<210> SEQ ID NO 31
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ttctaatacg actcactata gataactacg atacgggagg gttttagagc taga              54

<210> SEQ ID NO 32
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gcaaactatt aactggcgaa                                              20

<210> SEQ ID NO 33
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ttctaatacg actcactata gcaaactatt aactggcgaa gttttagagc taga        54

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ggcgaactac ttactctagc                                              20

<210> SEQ ID NO 35
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ttctaatacg actcactata ggcgaactac ttactctagc gttttagagc taga        54

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ggtgcctcac tgattaagca                                              20

<210> SEQ ID NO 37
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ttctaatacg actcactata ggtgcctcac tgattaagca gttttagagc taga        54

<210> SEQ ID NO 38
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gatggcatga cagtaagaga                                                    20

<210> SEQ ID NO 39
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ttctaatacg actcactata gatggcatga cagtaagaga gttttagagc taga             54

<210> SEQ ID NO 40
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
aaaagcaccg actcggtgcc acttttcaa gttgataacg gactagcctt attttaactt        60
gctatttcta gctctaaaac                                                    80

<210> SEQ ID NO 41
<211> LENGTH: 27
<212> TYPE: DNA
<213> ORGANISM: Homo sapiens

<400> SEQUENCE: 41
gccttccagc gtcggatggc tggcatg                                            27

<210> SEQ ID NO 42
<211> LENGTH: 9
<212> TYPE: PRT
<213> ORGANISM: Homo sapiens

<400> SEQUENCE: 42

Ala Phe Gln Arg Arg Met Ala Gly Met
1               5

<210> SEQ ID NO 43
<211> LENGTH: 27
<212> TYPE: DNA
<213> ORGANISM: Homo sapiens

<400> SEQUENCE: 43
cccttcttcc gaaccaacca ggtgatc                                            27

<210> SEQ ID NO 44
<211> LENGTH: 9
<212> TYPE: PRT
<213> ORGANISM: Homo sapiens

<400> SEQUENCE: 44

Pro Phe Phe Arg Thr Asn Gln Val Ile
1               5
```

<210> SEQ ID NO 45
<211> LENGTH: 25
<212> TYPE: DNA
<213> ORGANISM: Homo sapiens

<400> SEQUENCE: 45
atttaggggc tgggtgaccg atggc            25

<210> SEQ ID NO 46
<211> LENGTH: 6
<212> TYPE: PRT
<213> ORGANISM: Homo sapiens

<400> SEQUENCE: 46

Gly Trp Val Thr Asp Gly
1               5

<210> SEQ ID NO 47
<211> LENGTH: 27
<212> TYPE: DNA
<213> ORGANISM: Homo sapiens

<400> SEQUENCE: 47
gagctggagt caggaggcat gtaccac            27

<210> SEQ ID NO 48
<211> LENGTH: 9
<212> TYPE: PRT
<213> ORGANISM: Homo sapiens

<400> SEQUENCE: 48

Glu Leu Glu Ser Gly Gly Met Tyr His
1               5

<210> SEQ ID NO 49
<211> LENGTH: 25
<212> TYPE: DNA
<213> ORGANISM: Homo sapiens

<400> SEQUENCE: 49
gcgctcctgg cctctgcccg taagc            25

<210> SEQ ID NO 50
<211> LENGTH: 6
<212> TYPE: PRT
<213> ORGANISM: Homo sapiens

<400> SEQUENCE: 50

Ala Leu Leu Ala Ser Ala
1               5

<210> SEQ ID NO 51
<211> LENGTH: 24
<212> TYPE: DNA
<213> ORGANISM: Homo sapiens

<400> SEQUENCE: 51
gatgactgta cgctcccacg gtgg            24

<210> SEQ ID NO 52
<211> LENGTH: 8
<212> TYPE: PRT
<213> ORGANISM: Homo sapiens

<400> SEQUENCE: 52

Asp Asp Cys Thr Leu Pro Arg Trp
1               5

<210> SEQ ID NO 53
<211> LENGTH: 30
<212> TYPE: DNA
<213> ORGANISM: Homo sapiens

<400> SEQUENCE: 53
taccagatcc aggcgactgt gatgatcatc          30

<210> SEQ ID NO 54
<211> LENGTH: 10
<212> TYPE: PRT
<213> ORGANISM: Homo sapiens

<400> SEQUENCE: 54

Tyr Gln Ile Gln Ala Thr Val Met Ile Ile
1               5                   10

<210> SEQ ID NO 55
<211> LENGTH: 28
<212> TYPE: DNA
<213> ORGANISM: Homo sapiens

<400> SEQUENCE: 55
tggcaccgag caggtacggt tcatagag          28

<210> SEQ ID NO 56
<211> LENGTH: 4
<212> TYPE: PRT
<213> ORGANISM: Homo sapiens

<400> SEQUENCE: 56

Trp His Arg Ala
1

<210> SEQ ID NO 57
<211> LENGTH: 27
<212> TYPE: DNA
<213> ORGANISM: Homo sapiens

<400> SEQUENCE: 57
gccatcggcc gcggcaagtg gtggcga          27

<210> SEQ ID NO 58
<211> LENGTH: 9
<212> TYPE: PRT
<213> ORGANISM: Homo sapiens

<400> SEQUENCE: 58

Ala Ile Gly Arg Gly Lys Trp Trp Arg
1               5

<210> SEQ ID NO 59
<211> LENGTH: 26
<212> TYPE: DNA
<213> ORGANISM: Homo sapiens

<400> SEQUENCE: 59
accatgccta cagagtgtaa gtagtc          26

```
<210> SEQ ID NO 60
<211> LENGTH: 5
<212> TYPE: PRT
<213> ORGANISM: Homo sapiens

<400> SEQUENCE: 60

Thr Met Pro Thr Glu
1               5

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gggcacgggc agcttgccgg                                               20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gtcgccctcg aacttcacct                                               20

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(23)
<223> OTHER INFORMATION: a, c, t or g

<400> SEQUENCE: 63
gagtccgagc agaagaagaa nnn                                           23

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gagttagagc agaagaagaa agg                                           23

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gagtccgagc agaagaagaa ggg                                           23
```

```
<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gagtctaagc agaagaagaa gag                                              23

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gaggccgagc agaagaaaga cgg                                              23

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
aagtctgagc acaagaagaa tgg                                              23

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gagtcctagc aggagaagaa gag                                              23

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
acgtctgagc agaagaagaa tgg                                              23

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gagtccggga aggagaagaa agg                                              23
```

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
gaatccaagc aggagaagaa gga                                              23

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
gagtaggagc aggagaagaa gga                                              23

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gaggctgagc agaagaagaa tac                                              23

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gagtcagggc agaagaagaa aat                                              23

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gagaccgagc agaagaagca agc                                              23

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gagtctgagc ttctgcagaa ggc                                              23

```
<210> SEQ ID NO 78
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gaggctgagc agaggaagaa gaa                                              23

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
aaggctgagc agaggaagaa gac                                              23

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gagtccgaga agaagaaaga aaa                                              23

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
cagtcccagc agaagagaag gtg                                              23

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gaatccaagc agaagaagag aag                                              23

<210> SEQ ID NO 83
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gagtctgagc agaagaaaga aaa                                              23

<210> SEQ ID NO 84
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
gagtcagagc agaagaatgc cct                                              23

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gtgtctgagc agaggaagaa aga                                              23

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gagtcagagc aaaagaagta gtg                                              23

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
aagtcccggc agaggaagaa ggg                                              23

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
gaggcccagc agaggaagaa gag                                              23

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
aagtacaagc agaaaagaa gaa                                               23

<210> SEQ ID NO 90
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gagtccttgc agaagaagaa aaa                                           23

<210> SEQ ID NO 91
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
aagtacaagc aggagaagaa gaa                                           23

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gagcgcgagc agaagaaaag aag                                           23

<210> SEQ ID NO 93
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
gagtacgaga agaagaagag aga                                           23

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gagtcagagc agaagaaaga gga                                           23

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
tagtctgatg agaagaagaa agt                                           23

<210> SEQ ID NO 96
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(23)
<223> OTHER INFORMATION: a, c, t or g

<400> SEQUENCE: 96
gtcacctcca atgactaggg nnn                                              23

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gtcacctcca atgactaggg tgg                                              23

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
atcacttcca atgactaaga cgg                                              23

<210> SEQ ID NO 99
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gctacctcca gtgactaggg aag                                              23

<210> SEQ ID NO 100
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
gtcacctgta atgactaggg aga                                              23

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
cctacctcca atgactagag aag                                              23
```

```
<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
acaaccccca atgaccaggg agg                                              23

<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ttttcctcca atgaccaggg agg                                              23

<210> SEQ ID NO 104
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gtgacctcca atgcctagag ggg                                              23

<210> SEQ ID NO 105
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
agcacctcca atgaccaggt gtg                                              23

<210> SEQ ID NO 106
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
aggaccacca atgactaggg cag                                              23

<210> SEQ ID NO 107
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gacacaccca aagactaggg agg                                              23

<210> SEQ ID NO 108
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gccatctcca ctgactaggg gga                                            23

<210> SEQ ID NO 109
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ctcacctcca atgacaagga aga                                            23

<210> SEQ ID NO 110
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
accaccttca atgactaagg aac                                            23

<210> SEQ ID NO 111
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
attacctcca atgactagga gta                                            23

<210> SEQ ID NO 112
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
agtaccttca atgactaagg agt                                            23

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gtcacctcca gtgaccaggg agc                                            23

<210> SEQ ID NO 114
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
gtcatcttca atgacagggt gag                                              23

<210> SEQ ID NO 115
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
gccaccttca atggccaggg tga                                              23

<210> SEQ ID NO 116
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
gtcaccttca accactaggg ggt                                              23

<210> SEQ ID NO 117
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
ttctcctcca acgactaggg caa                                              23

<210> SEQ ID NO 118
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
atcaccccca aagacagggg aaa                                              23

<210> SEQ ID NO 119
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ctcacctcta atgtctagga agc                                              23

<210> SEQ ID NO 120
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 120
tctacctcca atgacttgga agg                                             23

<210> SEQ ID NO 121
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
atcacttcca atgatagggg aat                                             23

<210> SEQ ID NO 122
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
tcctcctcca atgactatag agt                                             23

<210> SEQ ID NO 123
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
gtctcttcta atgactagga aag                                             23

<210> SEQ ID NO 124
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
accacctgta atgactaggg tag                                             23

<210> SEQ ID NO 125
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
tataccccca aagactaggg tac                                             23

<210> SEQ ID NO 126
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 126
gccacttcta atgactagga aac                                              23

<210> SEQ ID NO 127
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
cccacctcca atgactatgg cat                                              23

<210> SEQ ID NO 128
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
ctcaccccca atgacagggg cct                                              23

<210> SEQ ID NO 129
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
ttcaccccca atgactgtgg aaa                                              23

<210> SEQ ID NO 130
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ttcacatcca atgactagta gat                                              23

<210> SEQ ID NO 131
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
tgtacctcca atgactaaga aat                                              23

<210> SEQ ID NO 132
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 132
agcaccccca ataactaggg tct                                              23

<210> SEQ ID NO 133
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
aatacctcca atgacttgga tga                                              23

<210> SEQ ID NO 134
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
agcacatcca aagactaggg gct                                              23

<210> SEQ ID NO 135
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(23)
<223> OTHER INFORMATION: a, c, t or g

<400> SEQUENCE: 135
ggttgtgcag ccgccgctcc nnn                                              23

<210> SEQ ID NO 136
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
ggttgtgcag ccgccgctcc aga                                              23

<210> SEQ ID NO 137
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
agttgtgcag ctgccgcacc tgc                                              23

<210> SEQ ID NO 138
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
tgttgtgcag ccaccgctgc tga                                           23

<210> SEQ ID NO 139
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
agttgtacag ccgccgcgcc tct                                           23

<210> SEQ ID NO 140
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(23)
<223> OTHER INFORMATION: a, c, t or g

<400> SEQUENCE: 140
gcagaaggga ttccatgagg nnn                                           23

<210> SEQ ID NO 141
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
tgagaagaga tcccatgagg gaa                                           23

<210> SEQ ID NO 142
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
gcagaaggga ttccatgagg tgc                                           23

<210> SEQ ID NO 143
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
gaagaagggt tccatgagg aga                                            23
```

<210> SEQ ID NO 144
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
tacaggggga ttccatgagg aga                                          23

<210> SEQ ID NO 145
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
acagagggga gaccatgagg aga                                          23

<210> SEQ ID NO 146
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
agagaaggga tcacatgagg aga                                          23

<210> SEQ ID NO 147
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
gctgaaggga ttcaatgagg tgc                                          23

<210> SEQ ID NO 148
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
ggagaggaga ttccatgagg aga                                          23

<210> SEQ ID NO 149
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
gcagagggaa ccccatgagg ggt                                          23

```
<210> SEQ ID NO 150
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
acagagggga tcccatgaga agg                                                23

<210> SEQ ID NO 151
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
tcagaaggga tccctgagg tgg                                                 23

<210> SEQ ID NO 152
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
acaggaggta ttccatgagg aac                                                23

<210> SEQ ID NO 153
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
aaagaaggga ttccgtaaga ggt                                                23

<210> SEQ ID NO 154
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
acagaaagga taccatgaga tgt                                                23

<210> SEQ ID NO 155
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
gctcaaggga tcccatgagg gac                                                23

<210> SEQ ID NO 156
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
gcagaaggga ttccaagggg aat                                             23

<210> SEQ ID NO 157
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
acggaaggga agccatgagg gga                                             23

<210> SEQ ID NO 158
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
gtagaagaga tcccaggagg ggc                                             23

<210> SEQ ID NO 159
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
gcaggaggga ttccctgagg aag                                             23

<210> SEQ ID NO 160
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
tcagaaggga tgtcatgagg agg                                             23

<210> SEQ ID NO 161
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
gcagaaggga aaccaggagg tga                                             23

<210> SEQ ID NO 162
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
aaggaaggga acccatgagg ggc                                           23

<210> SEQ ID NO 163
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
gcagaaggaa ccccatgagg aag                                           23

<210> SEQ ID NO 164
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
ccaggaggga ttccctgagg tgg                                           23

<210> SEQ ID NO 165
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
gcaggaggga tgccatgaag aga                                           23

<210> SEQ ID NO 166
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
cccataggga ttccatgagg tgt                                           23

<210> SEQ ID NO 167
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
ctagaaggga cttcatgagg tgt                                           23

<210> SEQ ID NO 168
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 168
gcagaaggga ttctgagggg tga                                              23

<210> SEQ ID NO 169
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
agagaaaggc ttccatgagg aga                                              23

<210> SEQ ID NO 170
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
agagaagaga tcccatgagg acg                                              23

<210> SEQ ID NO 171
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
acagaagggc ttccatgagg ctg                                              23

<210> SEQ ID NO 172
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
gcagaaggga ttccaggagt cca                                              23

<210> SEQ ID NO 173
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
ttagaagaga ttacatgagg aga                                              23

<210> SEQ ID NO 174
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 174
agcaaaggga gtccatgaga agg                                           23

<210> SEQ ID NO 175
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
tcagaagggg caccatgagg agc                                           23

<210> SEQ ID NO 176
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
gcagagggga ttccatgtga agg                                           23

<210> SEQ ID NO 177
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
actgaaggga ctccatgagg ttg                                           23

<210> SEQ ID NO 178
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
gcagaaggga ctccatgggg aag                                           23

<210> SEQ ID NO 179
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
ccaggaggga tccaatgagg ggc                                           23

<210> SEQ ID NO 180
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 180
gcagaaagga ttccatggag gag                                                23

<210> SEQ ID NO 181
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
acagaaggaa gaccatgaga aga                                                23

<210> SEQ ID NO 182
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
gcagaaagga tcccaggagg agc                                                23

<210> SEQ ID NO 183
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
gcagaaagaa tgccatgagg aga                                                23

<210> SEQ ID NO 184
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
aaagaaggga ctccatgatg gga                                                23

<210> SEQ ID NO 185
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
ggagaaggga tcccatgaaa tgg                                                23

<210> SEQ ID NO 186
<211> LENGTH: 23
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 186
tgagaagggt tccataagg tgt                                              23

<210> SEQ ID NO 187
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
gcagaagcaa ttccaaggag aga                                             23

<210> SEQ ID NO 188
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
cacggaggga tgccatgagg aga                                             23

<210> SEQ ID NO 189
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
acagaaggga ttctgagtgg agg                                             23

<210> SEQ ID NO 190
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
cctgaaggga tccctggagg ggg                                             23

<210> SEQ ID NO 191
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
ccagaaggtt ttccatgaga gga                                             23

<210> SEQ ID NO 192
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
gcagaaggga ttccagagga agg                                              23

<210> SEQ ID NO 193
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
gaagaaggga ttctgagagg tgt                                              23

<210> SEQ ID NO 194
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
agagaaggga ctccataggg gga                                              23

<210> SEQ ID NO 195
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
gcagaagaga atccctgagg agc                                              23

<210> SEQ ID NO 196
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
gcagagggga ttccaagaag ggg                                              23

<210> SEQ ID NO 197
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
gcagaaggca tttcatgagg ggt                                              23

<210> SEQ ID NO 198
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 198
gcaggagggg ttccaggtgg tca                                              23

<210> SEQ ID NO 199
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
aaggaaggga ttccatgaag gga                                              23

<210> SEQ ID NO 200
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
acagaaggta tttcatgagc aga                                              23

<210> SEQ ID NO 201
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
gcagaaagga atccatgagg act                                              23

<210> SEQ ID NO 202
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
agagaaggga atcaatgagg agg                                              23

<210> SEQ ID NO 203
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
gcggaaggga tgccatgagg gat                                              23

<210> SEQ ID NO 204
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
```
tcaggaggga ttccagaaga aga                                          23

<210> SEQ ID NO 205
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
tcaggaggga ttccagaaga agg                                          23

<210> SEQ ID NO 206
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
gtagagggga tttcttgagg aga                                          23

<210> SEQ ID NO 207
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
acagtgggga ttccatgagg ttg                                          23

<210> SEQ ID NO 208
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
gcagatgaga ctccatgagg gat                                          23

<210> SEQ ID NO 209
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
ggagaaggga tcccatgagg aca                                          23

<210> SEQ ID NO 210
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210

```
ccagaaggga ttccaagtgg aat                                          23
```

<210> SEQ ID NO 211
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211

```
ggagaaggga ccccataggg aag                                          23
```

<210> SEQ ID NO 212
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212

```
gcaaaagtga tcccatgagg cag                                          23
```

<210> SEQ ID NO 213
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213

```
agcaaagggt ttccatgagg aag                                          23
```

<210> SEQ ID NO 214
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214

```
acaggaggga ttccaagagg taa                                          23
```

<210> SEQ ID NO 215
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215

```
gaagaaggga taccttgagg aaa                                          23
```

<210> SEQ ID NO 216
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216

```
gcaaaagaga ttccaaggag agc                                          23
```

```
<210> SEQ ID NO 217
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
gcagaaggat ctccatgagg gtt                                           23

<210> SEQ ID NO 218
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
gcagaaggga ttccctggga gac                                           23

<210> SEQ ID NO 219
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
gcagaaaggg aaccatgagg cag                                           23

<210> SEQ ID NO 220
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
acagaatgga ctccatgaga gac                                           23

<210> SEQ ID NO 221
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
acagaaggga ttccatggaa caa                                           23

<210> SEQ ID NO 222
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
gtagaaggga ttccataggg aat                                           23
```

<210> SEQ ID NO 223
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
acagatggga tcccatgagt cac                                            23

<210> SEQ ID NO 224
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
cagagaggga ttccatgagg gaa                                            23

<210> SEQ ID NO 225
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
tctgaaggga ttccatgagg tct                                            23

<210> SEQ ID NO 226
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
gtagaaggaa ttccatgaag aaa                                            23

<210> SEQ ID NO 227
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
gcagaagtga tcccatgaga cag                                            23

<210> SEQ ID NO 228
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
gcagaaggaa ttccatgagt taa                                            23

```
<210> SEQ ID NO 229
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
acagaacaga ttccatgaga gat                                               23

<210> SEQ ID NO 230
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
ctccaaggga ttccatgagg gag                                               23

<210> SEQ ID NO 231
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
gcagaaggca ttccatagag ata                                               23

<210> SEQ ID NO 232
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
acagaaagca ttccatgagg acg                                               23

<210> SEQ ID NO 233
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
gctgaaggga caccgtgaga agt                                               23

<210> SEQ ID NO 234
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
acagaaagga tcccatgtgg gag                                               23

<210> SEQ ID NO 235
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
gcagagggaa ttccaaggga gaa                                              23

<210> SEQ ID NO 236
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
agagaagaga tcccatgatg aaa                                              23

<210> SEQ ID NO 237
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
gtagaaggga ttccatggta gta                                              23

<210> SEQ ID NO 238
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
acttaaggga ctccatgagg cag                                              23

<210> SEQ ID NO 239
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
ccaggaggaa ttccatgagg ctg                                              23

<210> SEQ ID NO 240
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
cgagagagga ttccatgagg ctg                                              23

<210> SEQ ID NO 241
<211> LENGTH: 23
```

-continued

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
ctagaaagga ctccatgagg aca                                          23

<210> SEQ ID NO 242
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
tgagaaggga agccatgagg gac                                          23

<210> SEQ ID NO 243
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
gcaggaggaa aaccatgagg gag                                          23

<210> SEQ ID NO 244
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
ttagaaggga ttccataggt att                                          23

<210> SEQ ID NO 245
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
gtaaaaggga ttccaagaga tag                                          23

<210> SEQ ID NO 246
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
ccagaaggaa ttccaagggc ttc                                          23

<210> SEQ ID NO 247
<211> LENGTH: 23
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 247
acagagggaa ccccatgagg cta                                            23

<210> SEQ ID NO 248
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
gcagaaagga tttcataggg agt                                            23

<210> SEQ ID NO 249
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
acagaagaga aaccatgaga aaa                                            23

<210> SEQ ID NO 250
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
gaagaaagga ttccataagg gat                                            23

<210> SEQ ID NO 251
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
gcagaggtga gtccatgagg gtg                                            23

<210> SEQ ID NO 252
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
gcagaagtaa atccattagg ccg                                            23

<210> SEQ ID NO 253
<211> LENGTH: 23
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 253
gcctaaggga tcccatgaag gtg                                              23

<210> SEQ ID NO 254
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
ggagaaggga ctccataagg aag                                              23

<210> SEQ ID NO 255
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
gcaaaaggga gtccaaggag aag                                              23

<210> SEQ ID NO 256
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
acagaaggta ttccatgaat aac                                              23

<210> SEQ ID NO 257
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
aatgaagaga tcccatgagg ctg                                              23

<210> SEQ ID NO 258
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
acagaaggaa ttcaatgagg gaa                                              23

<210> SEQ ID NO 259
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 259
actgcaggga ttccatgaga gaa                                              23

<210> SEQ ID NO 260
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
ttagaagaga tttcatgagt ggg                                              23

<210> SEQ ID NO 261
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
acagacagga ttccatgaga cca                                              23

<210> SEQ ID NO 262
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
gcagaaggga ctccaaaggg aga                                              23

<210> SEQ ID NO 263
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
gcagaaggaa ttccatacat gca                                              23

<210> SEQ ID NO 264
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
acagcaggaa ttccattagg gat                                              23

<210> SEQ ID NO 265
<211> LENGTH: 23
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 265
tgagaaggga ttccaagaaa aga                                              23

<210> SEQ ID NO 266
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
acaggaggga ttccagaggg aag                                              23

<210> SEQ ID NO 267
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
gcagaaagga ctccatggag ggg                                              23

<210> SEQ ID NO 268
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268 acagaggggatccaggaggaaa                                                23

<210> SEQ ID NO 269
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
gcagcaggaa ttccaaggag ctc                                              23

<210> SEQ ID NO 270
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(23)
<223> OTHER INFORMATION: a, c, t or g

<400> SEQUENCE: 270
gcaacctcta actaaccagg nnn                                              23

<210> SEQ ID NO 271
<211> LENGTH: 23
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 271
gcaacctcta actaaccagg taa                                              23

<210> SEQ ID NO 272
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
gctacctcta actaaccagg att                                              23

<210> SEQ ID NO 273
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
gcaactagta actaaccagg gag                                              23

<210> SEQ ID NO 274
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
ttatcctcta agtaaccagg agt                                              23

<210> SEQ ID NO 275
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
caaaccacta actaaccaga gga                                              23

<210> SEQ ID NO 276
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
caaacctcta cctaaccaga caa                                              23

<210> SEQ ID NO 277
<211> LENGTH: 23
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 277
acacactcta actaaccagg cag                                           23

<210> SEQ ID NO 278
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
tcaacctcta actagccaga cag                                           23

<210> SEQ ID NO 279
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
gcaacctcca acccaggagg tca                                           23

<210> SEQ ID NO 280
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
tcagccacta actaaccagg tga                                           23

<210> SEQ ID NO 281
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
acatcctcaa aataaccagg aag                                           23

<210> SEQ ID NO 282
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
gcaacctcta actaaccaat tat                                           23

<210> SEQ ID NO 283
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (21)..(23)
<223> OTHER INFORMATION: a, c, t or g

<400> SEQUENCE: 283
gggtggttcc ataatctgtg nnn                                              23

<210> SEQ ID NO 284
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
gggtggttcc ataatctgtg tat                                              23

<210> SEQ ID NO 285
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
gagtgactcc ataatctgtg tgc                                              23

<210> SEQ ID NO 286
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
gcgtggttac ataatctgtg gag                                              23

<210> SEQ ID NO 287
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
agggaattcc ataatctgtg taa                                              23

<210> SEQ ID NO 288
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
gggtggtacc caaatctgct tcc                                              23

<210> SEQ ID NO 289
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
tggtggttcc ataatgtatc atc                                              23

<210> SEQ ID NO 290
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
ggatgatacc ataatctgtg gat                                              23

<210> SEQ ID NO 291
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
aggtggttcc attctgtggg gtg                                              23

<210> SEQ ID NO 292
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
gagtgatgtc ataatctgtg tgc                                              23

<210> SEQ ID NO 293
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
gctgactcag agaccctgag tgg                                              23

<210> SEQ ID NO 294
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
gtccgagcag aagaagaagg gct                                              23

<210> SEQ ID NO 295
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 295
gtagagccta ctgctcttag gct                                          23
```

US 12,312,613 B2

UNCONSTRAINED GENOME TARGETING WITH NEAR-PAMLESS ENGINEERED CRISPR-CAS9 VARIANTS

CLAIM OF PRIORITY

This application claims the benefit of U.S. Provisional Patent Application Ser. No. 62/965,709, filed on Jan. 24, 2020. The entire contents of the foregoing are hereby incorporated by reference.

FEDERALLY SPONSORED RESEARCH OR DEVELOPMENT

This invention was made with Government support under Grant No. CA218870 awarded by the National Institutes of Health. The Government has certain rights in the invention.

SEQUENCE LISTING

This document includes a sequence listing submitted to the United States Patent and Trademark Office via the electronic filing system as an ASCII text file. The sequence listing, which is incorporated-by-reference herein, is titled "Sequence_Listing," was created on Jun. 8, 2021, and has a size of 79 kilobytes.

TECHNICAL FIELD

Described herein are *Streptococcus pyogenes* Cas9 (SpCas9) variants with relaxed PAM requirements capable of high-resolution editing for various applications, and methods of use thereof.

BACKGROUND

The requirement for DNA-targeting CRISPR-Cas enzymes to recognize a short sequence motif adjacent to target sites in foreign DNA is a critical step for distinguishing self from non-self[1,2]. For genome editing applications, however, the necessity of protospacer-adjacent motif[3-6] (PAM) recognition by Cas9 and Cas12a proteins constrains targeting and has major implications for editing efficiency and flexibility. The prototypical Cas9 from *Streptococcus pyogenes* (SpCas9) naturally recognizes target sites with NGG PAMs[5,7,8], making it one of the most targetable CRISPR enzymes characterized to-date. While other naturally occurring orthologs can in principle expand targeting by recognizing divergent non-canonical PAMs, the vast majority of Cas9 and Cas12a orthologs[9-12] require extended motifs that limit their utility for genome editing. Thus, the PAM requirement prevents the accurate positioning of CRISPR nuclease or base editor target sites and is a major barrier for several genome editing applications that command high resolution target site positioning (e.g., targeting small genetic elements, base editing, generating efficient HDR-mediated alterations, performing tiling screens, etc.[13-19]).

SUMMARY

The efficient manipulation of DNA in living cells requires genome editing technologies capable of targeting virtually any sequence. Because target site recognition by DNA-targeting CRISPR-Cas enzymes depends on the recognition of a protospacer adjacent motif (PAM), their ability to freely target within genomes is fundamentally limited to a subset of sequences. To remove this constraint, we pursued a rational directed engineering approach with the goal of reducing the NGG PAM requirement of the widely used *Streptococcus pyogenes* Cas9 (SpCas9). We first developed a highly active SpCas9 variant (named SpG) capable of targeting an expanded number of sequences bearing NGN PAMs at levels greater than previously described variants. We then further optimized this molecular scaffold to engineer for the first-time a near-PAMless SpCas9 variant (named SpRY). SpRY nuclease, cytosine base-editor, and adenine base-editor variants target almost all PAMs, exhibiting robust activities on a wide range of sites with NRN PAMs in human cells and lower but substantial activity on those with NYN PAMs. As shown herein, SpG and the near-PAMless SpRY can be used to generate previously inaccessible disease-relevant genetic variants. Collectively, the variants described herein are the most targetable CRISPR enzymes to-date, capable of high-resolution targeting for a variety of genome editing applications. The present findings provide broadly useful SpCas9 variants, referred to collectively herein as "variants" or "the variants".

Thus provided herein are isolated *Streptococcus pyogenes* Cas9 (SpCas9) proteins with mutations at one, two, three, four, five, or all six of the following positions: at E1219 (e.g., E to one of Q/H/S/V); S1136 (e.g., S to one of W/F/A/V); D1135 (e.g., D to one of L/A/W/F); G1218 (e.g., G to one of R/K/S); R1335 (e.g., R to one of Q); and/or T1337 (e.g., T to one of R/K).

In some embodiments, the proteins comprise a sequence that is at least 80% identical to the amino acid sequence of SEQ ID NO:1.

In some embodiments, the proteins comprise a set of mutations shown in Table 1.

In some embodiments, the proteins comprise one of the following sets of mutations: LWKQQR ("SpG"); LWRQQR; LWSQQR; LWKHQR; LWKSQR; LWRSQR; LWRSQK; LWSHQR; LWRHQR; LWRQQK; LWSQQK; LSKQQR; LWKQQK; LSKHQR; LWKSQR; LSRHQR; LWRVQK; LFRQQR; LSRQQR; LSRHQR; LSRSQR; LARQQR; LSRVQR; ASREQR; WSREQR; LSREQR; FSREQR; LSRQQR; LSKSQR; LWKVQK; LWKHQK; LWSSQK; LWSHQK; LWSSQR; LSRSQR; LWRVQR; LSKVQR; LWRHQR; LSSQQR; LWKVQR; LSRVQR; LWSVQK; LSSHQR; LWSVQR; LSSVQR; LSKQQK; LSRVQK; LSKVQK; LSSSQR; LSKSQK; LSSVQK; LSRQQK; LSSQQK; LSRSQK; or LSKHQK (variants with NGN PAM preference; name based on identities at D1135, S1136, G1218, E1219, R1335, T1337).

In some embodiments, the proteins further comprise a mutation at R1333 (e.g., R to P/C/A/V/G/K/L/S/T/Y/Q/I/H/N/M/D/E/F/W). In some embodiments, the proteins comprise one of the following sets of mutations LWKQPQR; LWKQCQR; LWKQAQR; LWKQVQR; LWKQGQR; LWKQSQR; LWKQTQR; LWKQKQR; LWKQLQR; LWKQYQR; LWKQQQR; LWKQIQR; LWKQHQR; LWKQNQR; LWKQMQR; LWKQDQR; LWKQEQR; LWKQFQR; or LWKQWQR (variants with NRN>NYN PAM preference; name based on identities at D1135, S1136, G1218, E1219, R1333, R1335, and T1337).

In some embodiments, the proteins further comprise a mutation at N1317 (e.g., N to R/K/H); G1104 (e.g., G to K/H/R); A61 (e.g., A to R/K/H); L1111 (e.g., L to R/K), and/or A1322 (e.g., A to R/K). In some embodiments, the proteins comprise a set of mutations shown in Tables 3-5. In some embodiments, the proteins comprise one of the following sets of mutations: D1135L/S1136W/G1218K/E1219Q/R1333P/R1335Q/T1337R/A61R+N1317R+

L1111R+A1322R; D1135L/S1136W/G1218K/E1219Q/R1333P/R1335Q/T1337R/G1104K+N1317R+L1111R+A1322R; D1135L/S1136W/G1218K/E1219Q/R1333P/R1335Q/T1337R/G1104K+N1317R+L1111R+A1322R; D1135L/S1136W/G1218K/E1219Q/R1333P/R1335Q/T1337R/A61R+G1104K+N1317R+L1111R+A1322R; D1135L/51136W/G1218K/E1219Q/R1333P/R1335Q/T1337R/A61R+G1104K+L1111R+A1322R; D1135L/S1136W/G1218K/E1219Q/R1333P/R1335Q/T1337R/A61R+G1104K+N1317R+L1111R+A1322R; D1135L/51136W/G1218K/E1219Q/R1333P/R1335Q/T1337R/A61R+N1317R+L1111R+A1322R; D1135L/S1136W/G1218K/E1219Q/R1333P/R1335Q/T1337R/A61R+G1104K+L1111R+A1322R; D1135L/51136W/G1218K/E1219Q/R1333P/R1335Q/T1337R/G1104K+N1317R+L1111R+A1322R; D1135L/S1136W/G1218K/E1219Q/R1333P/R1335Q/T1337R/A61R+G1104K+N1317R+L1111R+A1322R; D1135L/S1136W/G1218K/E1219Q/R1333P/R1335Q/T1337R/A61R+G1104K+L1111R+A1322R; D1135L/S1136W/G1218K/E1219Q/R1333P/R1335Q/T1337R/G1104K+L1111R+A1322R; D1135L/S1136W/G1218K/E1219Q/R1333P/R1335Q/T1337R/N1317R+L1111R+A1322R; D1135L/S1136W/G1218K/E1219Q/R1333P/R1335Q/T1337R/A61R+L1111R+A1322R; D1135L/S1136W/G1218K/E1219Q/R1333P/R1335Q/T1337R/N1317R+L1111R+A1322R; D1135L/S1136W/G1218K/E1219Q/R1333P/R1335Q/T1337R/G1104K+L1111R+A1322R; D1135L/S1136W/G1218K/E1219Q/R1333P/R1335Q/T1337R/A61R+L1111R+A1322R; D1135L/S1136W/G1218K/E1219Q/R1333P/R1335Q/T1337R/G1104K+L1111R+A1322R; D1135L/S1136W/G1218K/E1219Q/R1333P/R1335Q/T1337R/N1317R+L1111R+A1322R; and D1135L/S1136W/G1218K/E1219Q/R1333P/R1335Q/T1337R/A61R+L1111R+A1322R.

In some embodiments, the proteins further comprise one or more mutations that decrease nuclease activity selected from the group consisting of mutations at D10, E762, D839, H983, or D986; and at H840 or N863. In some embodiments, the mutations are:

(i) D10A or D10N, and
(ii) H840A, H840N, or H840Y.

In some embodiments, the proteins further comprise one or more mutations that increase specificity selected from the group consisting of mutations at N497, R661, N692, M694, Q695, H698, K810, K848, Q926, K1003, R0160, R691, M495, Y515, K526, and/or R661. In some embodiments, the proteins further comprise mutations at R691A, M495V, Y515N, K526E, R661Q, R661L, R661S, Y450A/Q695A, L169A/Q695A, Q695A/Q926A, Q695A/D1135E, Q926A/D1135E, Y450A/D1135E, L169A/Y450A/Q695A, L169A/Q695A/Q926A, Y450A/Q695A/Q926A, R661A/Q695A/Q926A, N497A/Q695A/Q926A, Y450A/Q695A/D1135E, Y450A/Q926A/D1135E, Q695A/Q926A/D1135E, L169A/Y450A/Q695A/Q926A, L169A/R661A/Q695A/Q926A, Y450A/R661A/Q695A/Q926A, N497A/Q695A/Q926A/D1135E, R661A/Q695A/Q926A/D1135E, and Y450A/Q695A/Q926A/D1135E; N692A/M694A/Q695A/H698A, N692A/M694A/Q695A/H698A/Q926A; N692A/M694A/Q695A/Q926A; N692A/M694A/H698A/Q926A; N692A/Q695A/H698A/Q926A; M694A/Q695A/H698A/Q926A; N692A/Q695A/H698A; N692A/M694A/Q695A; N692A/H698A/Q926A; N692A/M694A/Q926A; N692A/M694A/H698A; M694A/Q695A/H698A; M694A/Q695A/Q926A; Q695A/H698A/Q926A; G582A/V583A/E584A/D585A/N588A/Q926A; G582A/V583A/E584A/D585A/N588A; T657A/G658A/W659A/R661A/Q926A; T657A/G658A/W659A/R661A; F491A/M495A/T496A/N497A/Q926A; F491A/M495A/T496A/N497A; K918A/V922A/R925A/Q926A; or 918A/V922A/R925A; K855A; K810A/K1003A/R1060A; K848A/K1003A/R1060A; M495V/Y515N/K526E/R661Q; M495V/Y515N/K526E/R661L; or M495V/Y515N/K526E/R661S.

Also provided herein are fusion proteins comprising a protein described herein fused to a heterologous functional domain, with an optional intervening linker, wherein the linker does not interfere with activity of the fusion protein.

In some embodiments, the heterologous functional domain is a transcriptional activation domain. In some embodiments, the transcriptional activation domain is from VP16, VP64, rTA, NF-κB p65, or the composite VPR (VP64-p65-rTA).

In some embodiments, the heterologous functional domain is a transcriptional silencer or transcriptional repression domain. In some embodiments, the transcriptional repression domain is a Krueppel-associated box (KRAB) domain, ERF repressor domain (ERD), or mSin3A interaction domain (SID). In some embodiments, the transcriptional silencer is Heterochromatin Protein 1 (HP1).

In some embodiments, the heterologous functional domain is an enzyme that modifies the methylation state of DNA. In some embodiments, the enzyme that modifies the methylation state of DNA is a DNA methyltransferase (DNMT) or a TET protein. In some embodiments, the TET protein is TET1.

In some embodiments, the heterologous functional domain is an enzyme that modifies a histone subunit. In some embodiments, the enzyme that modifies a histone subunit is a histone acetyltransferase (HAT), histone deacetylase (HDAC), histone methyltransferase (HMT), or histone demethylase.

In some embodiments, the heterologous functional domain is a base editor or a prime editor. In some embodiments, the base editor is a DNA or RNA deaminase, e.g., a cytosine or adenine deaminase domain, or activation-induced cytidine deaminase; or wherein the prime editor comprises a reverse transcriptase (RT) domain.

In some embodiments, the heterologous functional domain is a biological tether. In some embodiments, the biological tether is MS2, Csy4 or lambda N protein.

In some embodiments, the heterologous functional domain is FokI.

Also provided herein are isolated nucleic acids encoding a protein described herein, as well as vectors comprising the isolated nucleic acids. In some embodiments, the isolated nucleic acid is operably linked to one or more regulatory domains for expressing an isolated Streptococcus pyogenes Cas9 (SpCas9) protein as described herein, e.g., with mutations at one, two, three, four, five, or all six of the following positions: D1135, S1136, G1218, E1219, R1335, and/or T1337.

Also provided herein are host cells, preferably mammalian host cells, comprising the nucleic acids described herein, and optionally expressing one or more of the proteins described herein.

Further provided herein are methods for altering the genome of a cell. The methods comprise expressing in the cell, or contacting the cell with, an isolated protein or fusion protein as described herein, and a suitable guide RNA (or prime RNA for prime editors) having a region complementary to a selected portion of the genome of the cell.

In some embodiments, the isolated protein or fusion protein comprises one or more of a nuclear localization sequence, cell penetrating peptide sequence, and/or affinity tag.

In some embodiments, the cell is a stem cell. In some embodiments, the cell is an embryonic stem cell, mesenchymal stem cell, or induced pluripotent stem cell; is in a living animal; or is in an embryo.

Also provided herein are methods for altering a double stranded DNA (dsDNA) molecule, the method comprising contacting the dsDNA molecule with an isolated protein or fusion protein as described herein, and a guide RNA (or prime RNA for prime editors) having a region complementary to a selected portion of the dsDNA molecule.

In some embodiments, the dsDNA molecule is in vitro.

In some embodiments, the fusion protein and RNA are in a ribonucleoprotein complex. The ribonucleoprotein complexes are also provided herein.

Also provided herein are fusion proteins comprising the isolated variant SpCas9 proteins described herein fused to a heterologous functional domain, with an optional intervening linker, wherein the linker does not interfere with activity of the fusion protein. In some embodiments, the heterologous functional domain is a transcriptional activation domain. In some embodiments, the transcriptional activation domain is from VP64 or NF-κB p65. In some embodiments, the heterologous functional domain is a transcriptional silencer or transcriptional repression domain. In some embodiments, the transcriptional repression domain is a Krueppel-associated box (KRAB) domain, ERF repressor domain (ERD), or mSin3A interaction domain (SID). In some embodiments, the transcriptional silencer is Heterochromatin Protein 1 (HP1), e.g., HP1α or HP1β. In some embodiments, the heterologous functional domain is an enzyme that modifies the methylation state of DNA. In some embodiments, the enzyme that modifies the methylation state of DNA is a DNA methyltransferase (DNMT) or a TET protein. In some embodiments, the TET protein is TET1. In some embodiments, the heterologous functional domain is an enzyme that modifies a histone subunit. In some embodiments, the enzyme that modifies a histone subunit is a histone acetyltransferase (HAT), histone deacetylase (HDAC), histone methyltransferase (HMT), or histone demethylase. In some embodiments, the heterologous functional domain is a base editor, e.g., a cytidine deaminase domain (e.g., APOBEC3 and APOBEC3 homologs and orthologs), activation-induced cytidine deaminase (e.g., AID and AID orthologs), adenine deaminase domain (e.g. TadA or engineered TadA derivatives), or other DNA or RNA deaminases. In some embodiments, the heterologous functional domain is a biological tether. In some embodiments, the biological tether is MS2, Csy4 or lambda N protein. In some embodiments, the heterologous functional domain is FokI. In some embodiments, the heterologous functional domain is a prime editor, e.g., a reverse-transcriptase (RT) domain (e.g., Moloney murine leukaemia virus (M-MLV) RT and other RT enzymes).

Also provided herein are isolated nucleic acids encoding the variant SpCas9 proteins described herein, as well as vectors comprising the isolated nucleic acids, optionally operably linked to one or more regulatory domains for expressing the variant SpCas9 proteins described herein. Also provided herein are host cells, e.g., mammalian host cells, comprising the nucleic acids described herein, and optionally expressing the variant SpCas9 proteins described herein. Also provided herein are ribonucleoprotein (RNP) complexes that include a variant SpCas9 protein as described herein and a guide RNA that targets a sequence having a PAM sequence targeted by the variant protein.

Also provided herein are methods of altering the genome of a cell, by expressing in the cell an isolated variant SpCas9 protein described herein, and a guide RNA having a region complementary to a selected portion of the genome of the cell.

Also provided herein are methods for altering, e.g., selectively altering, the genome of a cell by expressing in the cell the variant proteins, and a guide RNA having a region complementary to a selected portion of the genome of the cell.

Also provided are methods for altering, e.g., selectively altering, the genome of a cell by contacting the cell with a protein variant described herein, and a guide RNA having a region complementary to a selected portion of the genome of the cell.

In some embodiments, the isolated protein or fusion protein comprises one or more of a nuclear localization sequence, cell penetrating peptide sequence, and/or affinity tag.

In some embodiments of the methods described herein, the cell is a stem cell, e.g., an embryonic stem cell, mesenchymal stem cell, or induced pluripotent stem cell; is in a living animal; or is in an embryo, e.g., a mammalian, insect, or fish (e.g., zebrafish) embryo or embryonic cell.

Further, provided herein are methods, e.g., in vitro methods, for altering a double stranded DNA (dsDNA) molecule. The methods include contacting the dsDNA molecule with one or more of the variant proteins described herein, and a guide RNA having a region complementary to a selected portion of the dsDNA molecule.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-I. Engineering and characterization of SpCas9 variants capable of targeting NGN PAMs.

Figure 4:
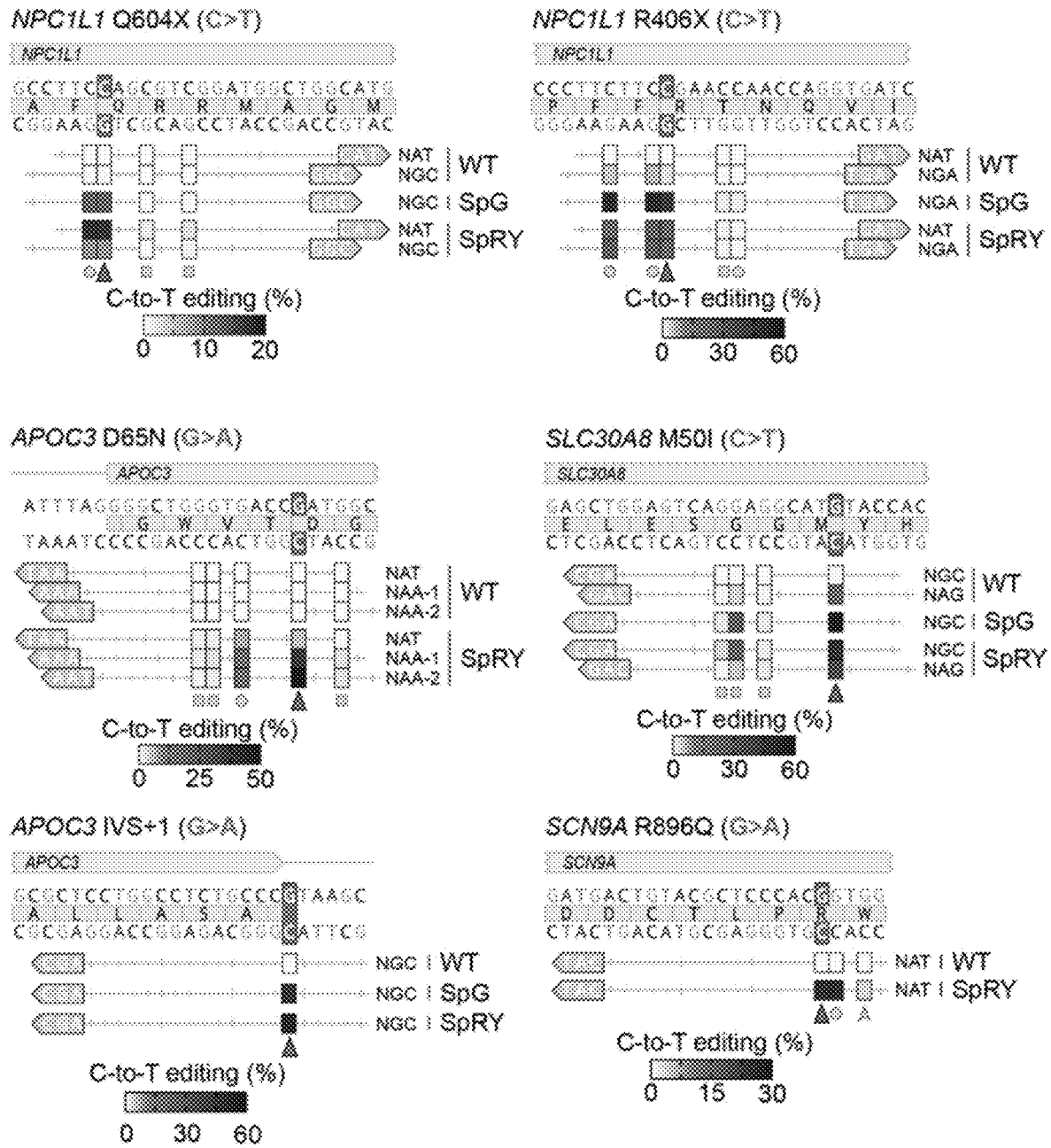

a, Schematic of SpCas9, highlighting the PAM-interacting (PI) domain along with R1333 and R1335 that make base-specific contacts to the guanines of the NGG PAM. b, Rendering of a crystal structure of SpCas9 with amino acid side chains proximal to the second guanine of the NGG PAM shown in yellow. In the zoomed image the non-target strand (NTS) is hidden for clarity. Image generated from PDB ID 4UN3[1]. c, HT-PAMDA characterization of wild-type (WT) SpCas9 and engineered variants to illustrate their NGNN PAM preferences. The $\log_{10}$ rate constants (k) are the mean of at least two replicates against two distinct spacer sequences (see also FIGS. 6a and 6e-6g). d, Modification of endogenous sites in human cells bearing a canonical and noncanonical PAMs with WT SpCas9 and SpG Editing assessed by targeted sequencing; mean, s.e.m., and individual data points shown for n=3. e, Mean nuclease activity plots for WT, xCas9[2], SpCas9-NG[3], and SpG on 78 sites with NGN PAMs in human cells. The black line represents the mean of 19-20 sites for each PAM class (see also FIG. 9a). f, HT-PAMDA characterization of WT, xCas9, SpCas9-NG, and SpG to illustrate their NGNN PAM preferences. The $\log_{10}$ rate constants (k) are the mean of at least two replicates against two distinct spacer sequences. g, Mean C-to-T editing plots for WT, xCas9, SpCas9-NG, and SpG cytosine base editors (CBEs) on 57 cytosines within the editing windows (positions 3 through 9) of 20 target sites harboring NGN PAMs in human cells. The black line represents the mean of 12-16 cytosines for each PAM class (see also FIG. 10a). h, CBE-HT-PAMDA data for WT, xCas9, SpCas9-NG, and SpG to illustrate their NGNN PAM preferences. The $\log_{10}$ rate constants (k) are single replicates against one spacer sequence (see also FIGS. 10c and 10d). i, Mean A-to-G editing plots for WT, xCas9, SpCas9-NG, and SpG adenine base editors (ABEs) on 24 adenines within the editing windows (positions 5 through 7) of 21 target sites harboring NGN PAMs in human cells. The black line represents the mean of 3-9 adenines for each PAM class (see also FIG. 11a).

FIGS. 2A-D. Engineering and characterization of SpCas9 variants capable of targeting NRN PAMs. a, Crystal structure of SpCas9 to illustrate amino acid side chains of R1333 and selected PAM-proximal residues. The non-target strand (NTS) is hidden for clarity. Image generated from PDB ID 4UN3[1]. b, Modification of endogenous sites in human cells bearing different NRN PAMs with WT SpCas9, SpG, and SpG derivatives. Editing assessed by targeted sequencing; mean, s.e.m., and individual data points shown for n=3. c, HT-PAMDA characterizations of WT SpCas9, SpG, and SpG derivatives to illustrate their NRNN PAM preferences. The $\log_{10}$ rate constants (k) are the mean of at least two replicates against two distinct spacer sequences (see also FIGS. 6a and 6e-g). d, Modification of endogenous sites in human cells bearing different NRN PAMs SpG (L1111R/A1322R/R1333P) and derivatives bearing additional substitutions. A subset of data re-presented from FIG. 12c for clarity. Editing assessed by targeted sequencing; mean, s.e.m., and individual data points shown for n=3.

FIGS. 3A-F. Comparison of WT SpCas9 and SpRY nuclease and base editor activities across NNN PAM sites in human cells. a, b, Mean nuclease activity plots for WT SpCas9 and SpRY on 64 sites with NRN PAMs (a) and 31 sites with NYN PAMs (b) in human cells. The black line represents the mean of 8 or 3-4 sites (panels a and b, respectively) for each PAM of the indicated class (see also FIGS. 13a-9c). c, d, C-to-T base editing of endogenous sites in human cells bearing NRN and NYN PAMs (c and d, respectively) with WT SpCas9 and SpRY-CBE4max constructs. Editing of cytosines in the edit window (positions 3 through 9) assessed by targeted sequencing; the five NYN PAM target sites were selected from high-activity sites in b; mean, s.e.m., and individual data points shown for n=3. e, f, A-to-G base editing of endogenous sites in human cells bearing NRN and NYN PAMs (e and f, respectively) with WT SpCas9 and SpRY-ABEmax constructs. Editing of adenines in the edit window assessed by targeted sequencing; the five NYN PAM target sites were selected from high-activity sites in b; mean, s.e.m. and individual data points shown for n=3. For base editing data in c-f.

FIG. 4|Expanded capabilities of C-to-T base editors with SpG and SpRY to generate protective genetic variants. Comparison of the C-to-T editing activities of WT SpCas9, SpG, and SpRY CBE4max constructs across 22 target sites covering ten previously described protective genetic variants (intended edit highlighted in orange). C-to-T editing for cytosines within the spacer that are edited above 1% by any variant are plotted for all appropriate variant/guide combinations; SpG was tested only on sites harboring NGN PAMs; editing of cytosines assessed by targeted sequencing with mean C-to-T editing shown for n=3. The intended edit, bystander synonymous, non-synonymous, and stop codon C-to-T edits are indicated; the PAMs for each target site are shown in the grey arrow annotation.

FIG. 4 discloses SEQ ID NOS 41, 43, 42, 44, 45, 47, 46, 48, 49, 51, 50, 52, 53, 55, 54, 56, 57, 59, 58 and 60, respectively, in order of appearance.

FIGS. 5A-I. Structural models of PAM recognition by SpCas9 and engineered variants. a, b, Molecular mechanisms of NGG PAM recognition by WT SpCas9 (a) and NGA PAM recognition by SpCas9-VQR (b) with key residues shown. c, Overlay of the non-target strand PAM DNA from WT SpCas9 (blue) and SpCas9-VQR (maroon) crystal structures with key residues labeled. The $3^{rd}$ base of the PAM in the SpCas9-VQR structure is displaced towards R1333Q on the major groove side of the duplex relative to the wild-type structure. d, In the context of SpCas9-VQR, the T1337R substitution forms a base-specific contact with $dG_4$ of an NGAG PAM. e, In the context of SpCas9-VRER, the G1218R substitution interacts with the PAM DNA phosphate backbone. f-i, Structural predictions for how the addition of E1219Q to SpCas9-VQR might enable recognition of NGN PAM sequences, modeled on NGA (f), NGC (g), NGG (h), and NGT (i) PAMs. For all panels, structures were visualized in PyMOL (v 2.3.3) using PDB IDs 4UN3 (WT SpCas9)[1], 5B2R (SpCas9-VQR)[4], and 5B2T (SpCas9-VRER)[4]; certain protein and nucleic acid residues were omitted for clarity.

Figure 6A:
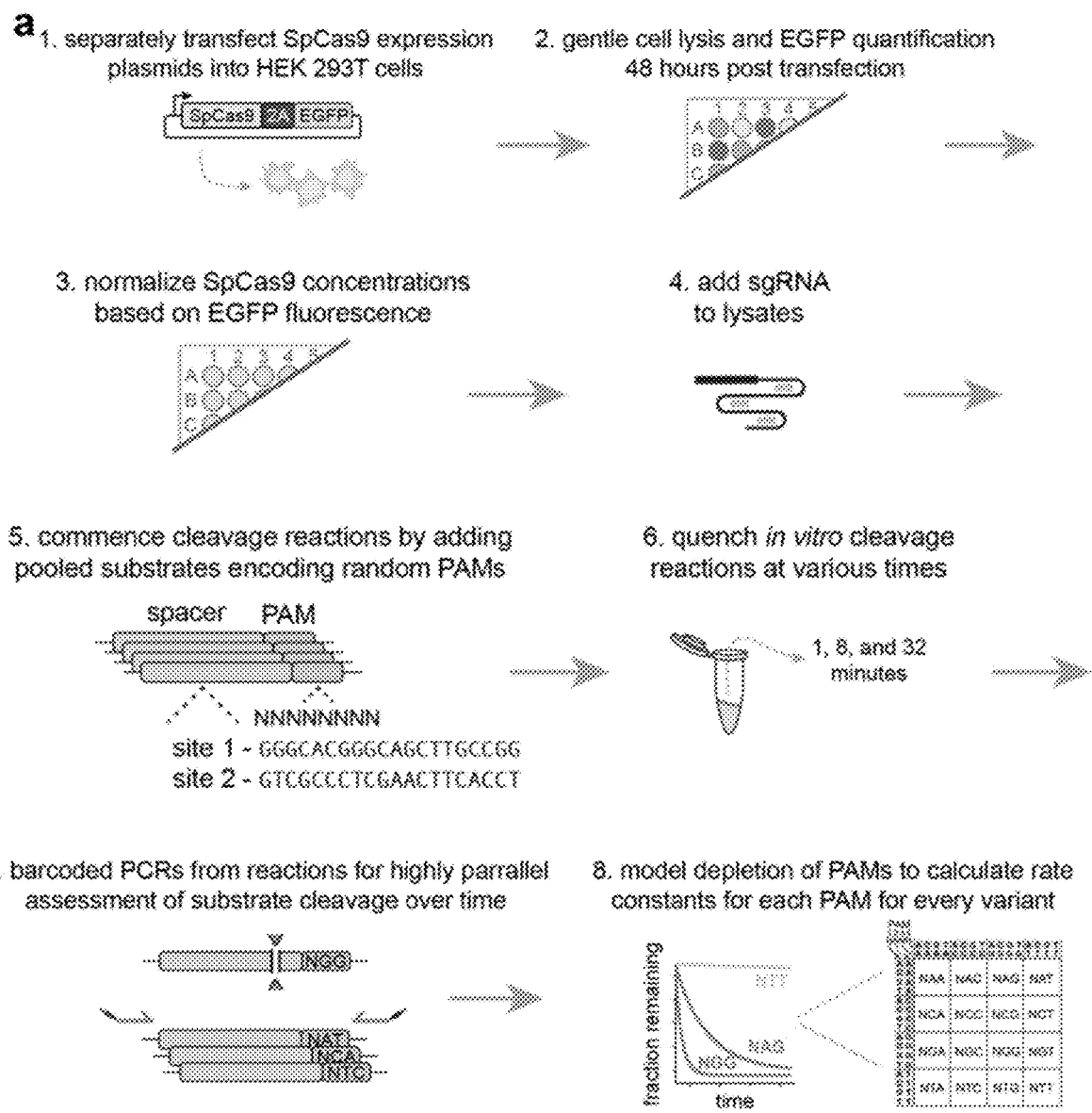

FIGS. 6A-G. Optimization and application of a high-throughput PAM determination assay (HT-PAMDA). a, Schematic of the HT-PAMDA workflow. SpCas9 proteins are expressed in human cells and harvested by gentle lysis, with SpCas9 concentrations normalized by EGFP fluorescence. Two libraries harboring randomized PAMs with separate spacer sequences are subjected to timecourse in vitro cleavage reactions using SpCas9 lysate complexed with sgRNAs. PAM depletion over time is monitored by deep sequencing and modeled to generate rate constants for each PAM. FIG. 6A discloses SEQ ID NOS 61-62, respectively, in order of appearance. b, Correlation of HT-PAMDA $\log_{10}$ rates (k) for NNNN PAMs across two randomized PAM libraries with distinct spacer sequences (wild-type SpCas9: $r^2=0.9167$; SpCas9-VQR: $r^2=0.9065$). c, Correlation of HT-PAMDA rates for NNNN PAMs across two technical replicates, where each technical replicate is the average of experiments on the two libraries harboring distinct spacer sequences (wild-type SpCas9: $r^2=0.9770$; SpCas9-VQR: $r^2=0.9329$). In panels b and c, HT-PAMDA logo (k) were set to a minimum value of −4. d, HT-PAMDA NNNN profiles of the well-characterized WT SpCas9, SpCas9-VQR, and SpCas9-VRER nucleases[5-7]. e, HT-PAMDA NGNN profiles of WT SpCas9 and engineered variants; some variants are shown twice for completeness. f, HT-PAMDA NNNN PAM profiles of SpG, SpCas9-NG, and xCas9 (3.7). g, HT-PAMDA NNNN PAM profiles of SpG with L1111R and A1322R substitutions, SpCas9-NG without the requisite L1111R and A1322R substitutions, and xCas9 (3.7) without the A262T, R324L, S409I, E480K, E543D, and M694I substitutions. For panels d-g, HT-PAMDA $\log_{10}$ (k) are the mean of at least two replicates against two distinct spacer sequences.

FIGS. 7A-D. Nuclear localization signal (NLS) architecture assessment for SpCas9. a, Schematics of the thirteen NLS architectures tested with wild-type SpCas9. Constructs 7 and 13 are similar to as previously described[8,9]. b-d, Modification of two sites in HEK 293T cells bearing NGG PAMs using WT SpCas9 with the NLS architectures described in (a), using 29 ng (b), 5.8 ng (c), or 1.2 ng (d) of SpCas9-expression plasmid. Percent modified reads in b-d assessed by targeted sequencing; mean, s.e.m., and individual data points shown for n=3. Constructs harboring a C-terminal BP (SV40) NLS-3xFLAG-P2A-EGFP sequence (construct #7) were utilized for all human cell experiments unless otherwise indicated.

FIGS. 8A-F. Engineering SpG for efficient targeting of NGN PAMs. a, Modification of endogenous sites in HEK 293T cells bearing NGAT, NGCC, NGGG, and NGTA PAMs by WT SpCas9, SpCas9-VRQR[10], and derivative variants of SpCas9-VRQR. b, Modification of endogenous sites in HEK 293T cells bearing NGAT, NGCC, NGGG, and NGTA PAMs by WT SpCas9 and variants bearing substitutions at positions D1135, S1136, G1218, E1219, R1335, and T1337. c-f, Modification of 16 sites in HEK293T cells bearing NGNN PAMs by SpCas9-NG and derivatives lacking one or both of the requisite L1111R and A1322R substitutions (bar plots of data in c; summary of data in d), and by SpG and derivatives harboring one or both of the L1111R and A1322R substitutions (bar plots of data in e; summary of data in f). Percent modified reads in a-f assessed by targeted sequencing; mean, s.e.m., and individual data points shown for n=3.

FIGS. 9A-F. Characterization of SpCas9 nucleases capable of targeting NGN PAMs. a, Modification of 78 endogenous sites in HEK 293T cells bearing NGNN PAMs by WT SpCas9, xCas9, SpCas9-NG, and SpG. Percent modification assessed by targeted sequencing; mean, s.e.m., and individual data points shown for n=3. b-d, Summaries of the results in a, but grouped by the base identity of the $1^{st}$ spacer proximal nt of the PAM (NGNN; b), the $4^{th}$ nt of the PAM (NGNN; c), or the $1^{st}$ PAM proximal nt of the spacer (d). e, Summary of the results in a for WT and xCas9, but separated by both canonical NGG PAM versus non-canonical NGH PAMs (where H=A, C, or T) and the corresponding $4^{th}$ nt base of the PAM for C versus D (where D=A, G, or T). In b-e, mean modification of each site from a is shown; mean modification across each subset of PAMs is shown as a line. f, Correlation between HT-PAMDA logo (k) (see FIGS. 6e and f) and mean human cell modification from a for each NGNN PAM (WT SpCas9: $r^2$=0.9918; xCas9: $r^2$=0.8715; SpCas9-NG: $r^2$=0.6461; SpG: $r^2$=0.4754). HT-PAMDA $\log_{10}$(k) were set to a minimum value of −4.

Figure 10A:
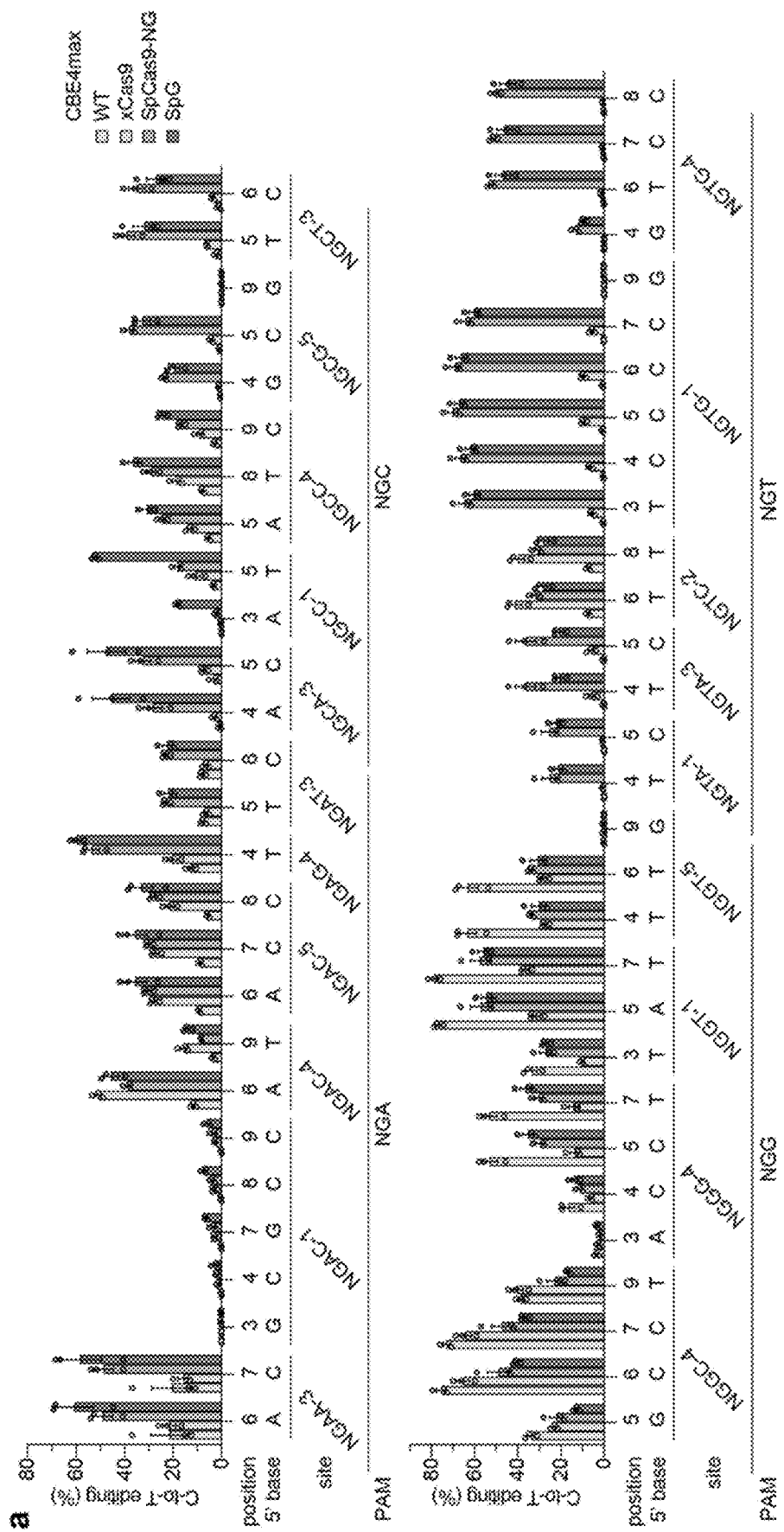

FIGS. 10A-E. Characterization of C-to-T base editors capable of targeting NGN PAMs. a, C-to-T base editing of 57 cytosines across 20 endogenous sites in HEK 293T cells bearing NGN PAMs with WT SpCas9, xCas9, SpCas9-NG, and SpG CBE4max contructs. C-to-T editing within the edit window (positions 3 through 9) assessed by targeted sequencing; mean, s.e.m. and individual data points shown for n=3. b, Scatterplots of C-to-T editing of all cytosines in the spacer compared to position in the spacer for sites from a, to define the edit window and the impact of the identity of the preceeding base 5' of each cytosine. Mean and s.e.m. shown for n=3. c, Schematic of the cytosine base editor (CBE) HT-PAMDA (CBE-HT-PAMDA) workflow. CBE4max variants are expressed in human cells and harvested by gentle lysis, with CBE4max concentrations normalized by EGFP fluorescence. A library harboring randomized PAMs is subjected to timecourse in vitro reactions using CBE4max lysate complexed with sgRNAs. Following termination of each reaction, USER enzyme is added to convert C-to-U deamination events to double-strand breaks when they co-occur with SpCas9-HNH domain mediated DNA nicks. PAM depletion over time is monitored by deep sequencing and modeled to generate rate constants for each PAM. FIG. 10C discloses SEQ ID NO: 62. d, CBE-HT-PAMDA NNNN profiles for WT SpCas9, xCas9, SpCas9-NG, and SpG CBE4max constructs. e, Correlation of HT-PAMDA $\log_{10}$ rate constants (k) with CBE-HT PAMDA $\log_{10}$ rate constants (WT CBE4max: $r^2$=0.9691; xCas9 CBE4max: $r^2$=0.8553; SpCas9-NG CBE4max: $r^2$=0.8342; SpG CBE4max: $r^2$=0.9452). HT-PAMDA logo (k) and CBE-HT-PAMDA $\log_{10}$ (k) were set to minimum values of −4 and −5, respectively.

FIGS. 11A-B. Characterization of A-to-G base editors capable of targeting NGN PAMs. a, A-to-G base editing of 26 adenines across 21 endogenous sites in HEK 293T cells bearing NGN PAMs with WT SpCas9, xCas9, SpCas9-NG, and SpG ABEmax constructs. A-to-G editing within the edit window (positions 5 through 7) assessed by targeted sequencing; mean, s.e.m. and individual data points shown for n=3. b, Scatterplots of A-to-G editing of all adenines in the spacer compared to position in the spacer for sites from a, to define the edit window and the impact of identity of the preceding base 5' of each adenine. Mean and s.e.m. shown for n=3.

FIGS. 12A-D. Engineering SpRY for efficient targeting of NR PAM sequences. a, b, HT-PAMDA NRNN nt PAM profiles of SpG (L1111R/A1322R) derivatives bearing all possible amino acid substitutions at R1333 (panel a), and of SpG (L1111R/A1322R) derivatives bearing substitutions at A61, G1104, and N1317 in the context of R1333A/C/P (panel b). c, Modification of four endogenous sites in HEK 293T cells bearing NRN PAMs by SpG (L1111R/A1322R) derivatives. Percent modification assessed by targeted sequencing; mean, s.e.m., and individual data points shown for n=3. d, HT-PAMDA NNNN PAM profiles of SpG, SpRY, and selected intermediate variants. For panels a, b, and d, HT-PAMDA $\log_{10}$ (k) are the mean of at least two replicates against two distinct spacer sequences.

FIGS. 13A-J. Characterization of SpRY nuclease activities. a, b, Modification of 32 endogenous sites in HEK 293T cells bearing NANN PAMs with WT SpCas9 and SpRY (a), and 32 sites bearing NGNN PAMs with WT SpCas9, SpG and SpRY (b). Percent modification assessed by targeted sequencing; mean, s.e.m., and individual data points shown for n=3. c, Summary of the results in b, grouped by $3^{rd}$ nt of the PAM for WT, SpG, and SpRY. d, Molecular mechanisms for recognition of the $2^{nd}$ base of the PAM for WT SpCas9 (left) and the R1333P variant (right) with key residues shown. Structures were visualized in PyMOL (v 2.3.3) using PDB ID 4UN3 (WT SpCas9)[1]; certain protein and nucleic acid residues were omitted for clarity. e, Modification of 31 endogenous sites bearing NYNN PAMs by WT SpCas9 and SpRY. Percent modification assessed by targeted sequencing; mean, s.e.m., and individual data points shown for n=3. f, Correlation between HT-PAMDA $\log_{10}$ (k) for WT and SpRY (see FIGS. 6e and 12d, respectively) and mean human cell modification from a, b, and e for each NNN PAM (WT SpCas9: 12=0.9868; SpRY-Cas9: $r^2$=0.4589). g-j, Summaries of the results in a, b, and e grouped by $1^{st}$ nt of the PAM (g), $3^{rd}$ nt of the PAM (h), $4^{th}$ nt of the PAM (i), and $1^{st}$ PAM proximal nt of the spacer (j) for WT and SpRY.

FIGS. 14A-F. Characterization of SpRY base editor activities. a, b, Summaries of the C-to-T editing activities of WT- and SpRY-CBE from FIGS. 3c and 3d, respectively.

Each data point represents the mean of the 3 replicates; horizontal line signifies the mean. c, Scatterplots of C-to-T editing of all cytosines in the spacer compared to position in the spacer for sites from FIGS. 3c and 3d, to define the edit window and the impact of the identity of the preceding base 5' of each cytosine for WT- and SpRY-CBE, respectively. Mean and s.e.m. shown for n=3. d, e, Summaries of the A-to-G editing activities of WT- and SpRY-ABE from FIGS. 3e and 3f, respectively. Each data point represents the mean of the 3 replicates; horizontal line signifies the mean. f, Scatterplots of A-to-G editing of all adenines in the spacer compared to position in the spacer for sites from FIGS. 3e and 3f, to define the edit window and the impact of the identity of the preceding base 5' of each adenine for WT- and SpRY-ABE, respectively. Mean and s.e.m. shown for n=3.

Figure 15:
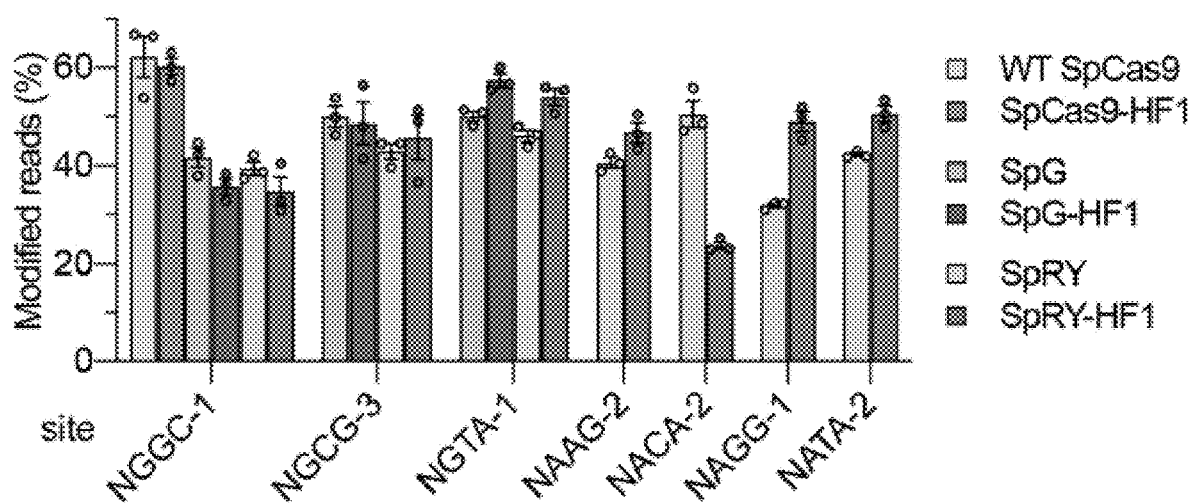

FIG. 15. Compatibility of SpG and SpRY with specificity improving substitutions. Modification of endogenous sites in HEK 293T cells by WT SpCas9, SpG, and SpRY and their respective HF1 derivatives (bearing N497A/R661A/Q695A/Q926A substitutions). Percent modification assessed by targeted sequencing; mean, s.e.m., and individual data points shown for n=3.

FIGS. 16A-C. On-target and genome-wide specificity analysis of high-fidelity PAM variants. (A) Relative nuclease activity plots for SpCas9-HF1, SpCas9-NG-HF1, SpG-HF1, and SpRY-HF1 compared to their parental variants across 3-10 endogenous sites in HEK 293T cells. Mean modification from sites in FIG. 17A shown as dots, with black line representing the mean of those sites, and the grey outline is a violin plot. The HF1 variants additionally encode N497A, R661A, Q695A, and Q926A substitutions. (B) The number of GUIDE-seq detected off-target sites for SpCas9 variants across sites with NGG, NGN, and NAN PAMs (see FIGS. 7A-C, respectively). (C) Fraction of GUIDE-seq reads attributed to the on- and off-target sites for WT SpCas9, SpG, SpRY, and their respective HF1 variants across 2-6 targets (see also FIGS. 18A-C).

FIGS. 17A-F. Evaluation of on-target editing with WT, SpG, SpRY, and their respective HF1 variants. (A, B). Modification of endogenous sites in HEK 293T cells by WT SpCas9, SpCas9-NG, SpG, SpRY, and their respective high-fidelity (HF1) derivatives from transfections without (A) or containing (B) the GUIDE-seq double-stranded oligodeoxynucleotide (dsODN) tag. Percent modification assessed by targeted sequencing; mean, s.e.m., and individual data points shown for n=3. (C) Summary of the mean relative nuclease activity of the HF1 derivatives of WT, SpG, and SpRY (from B). The black line represents the mean of 3-10 sites for each pair of variants), and the grey outline is a violin plot. (D) GUIDE-seq dsODN capture at on-target sites by WT SpCas9, SpG, SpRY, and their respective HF1 variants. Percent modification assessed by targeted sequencing; mean, s.e.m., and individual data points shown for n=3. (E) Summary of the mean relative dsODN capture of the HF1 derivatives of WT, SpG, and SpRY (from panel D). The black line represents the mean of 3-10 sites for each pair of variants), and the grey outline is a violin plot. (F) Ratio of GUIDE-seq dsODN tag capture (D) to overall mutagenesis (B) for WT SpCas9, SpG, SpRY, and their respective HF1 variants. The black line represents the mean of 3-10 sites for each pair of variants), and the grey outline is a violin plot; HF1 variants encode N497A, R661A, Q695A, and Q926A substitutions.

Figure 18A:
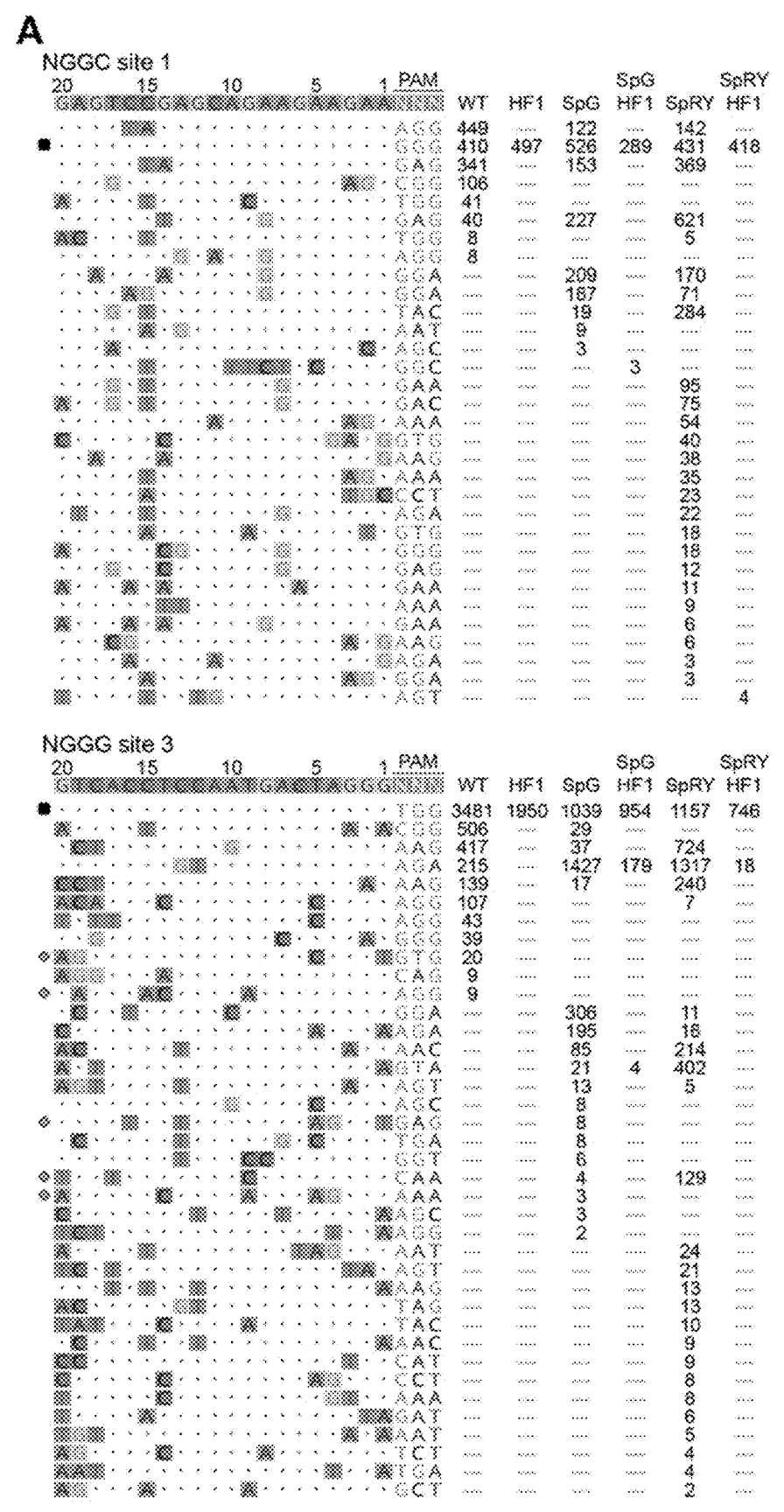
Figure 18B:
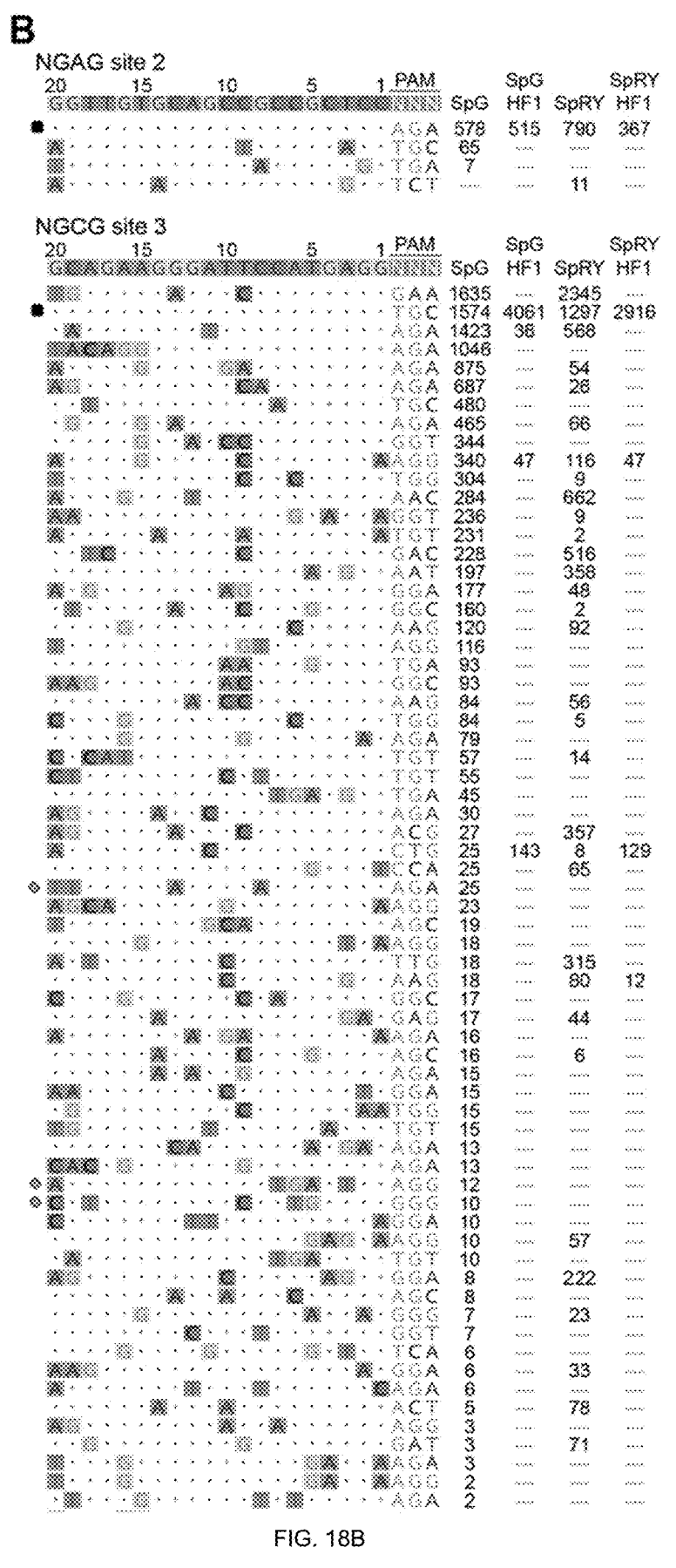
Figure 18C:
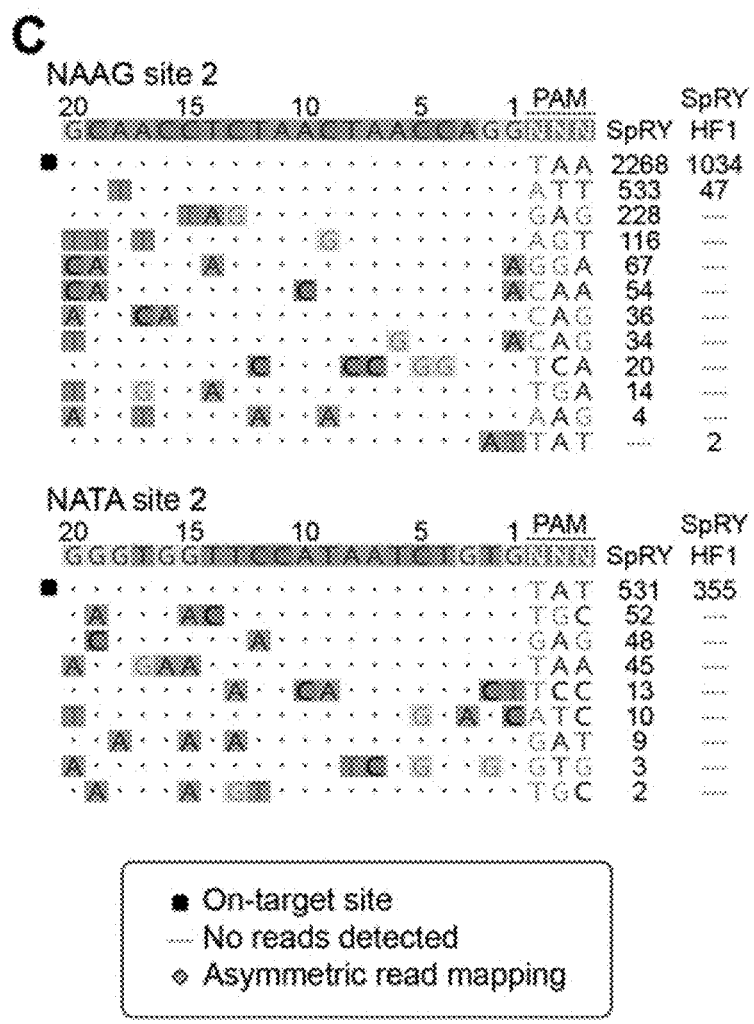

FIGS. 18A-C. Genome-wide specificity assessments of relaxed PAM variants. GUIDE-seq genome-wide specificity profiles of WT, SpG, SpRY and their respective high-fidelity (HF1) derivatives with gRNAs targeted to sites harboring NGG (panel A), NGN (panel B), or NRN (panel C) PAMs. Mismatched positions in the spacers of the off-target sites are highlighted; GUIDE-seq read counts from consolidated unique molecular events for each variant are shown to the right of the sequence plots; diamonds indicate sites that are only supported by asymmetric GUIDE-seq reads; nucleotides within the PAMs of the on- and off-target sites are shown for clarity. HF1 variants encode N497A, R661A, Q695A, and Q926A substitutions. FIGS. 18A-C disclose SEQ ID NOS 63-292, respectively, in order of appearance.

FIGS. 19A-B. Characterization of improved A-to-G base editor fusions to relaxed PAM variants. (A) A-to-G base editing on an endogenous site with an NGG PAM in HEK 293T cells by SpCas9, SpG, and SpRY fusions to ABE (7.10), ABE (8.20 m), and ABE8e deaminase domains. A-to-G editing assessed by targeted sequencing; individual datapoints within the heatmaps are the mean of 3 replicates. FIG. 19A discloses SEQ ID NO: 293. (B) A-to-G base editing on two additional endogenous sites with NCT PAMs in HEK 293T cells by SpRY fusions to ABE (7.10), ABE (8.20 m), and ABE8e deaminase domains. A-to-G editing assessed by targeted sequencing; individual datapoints within the heatmaps are the mean of 3 replicates. FIG. 19B discloses SEQ ID NOS 294-295, respectively, in order of appearance.

Figure 20:
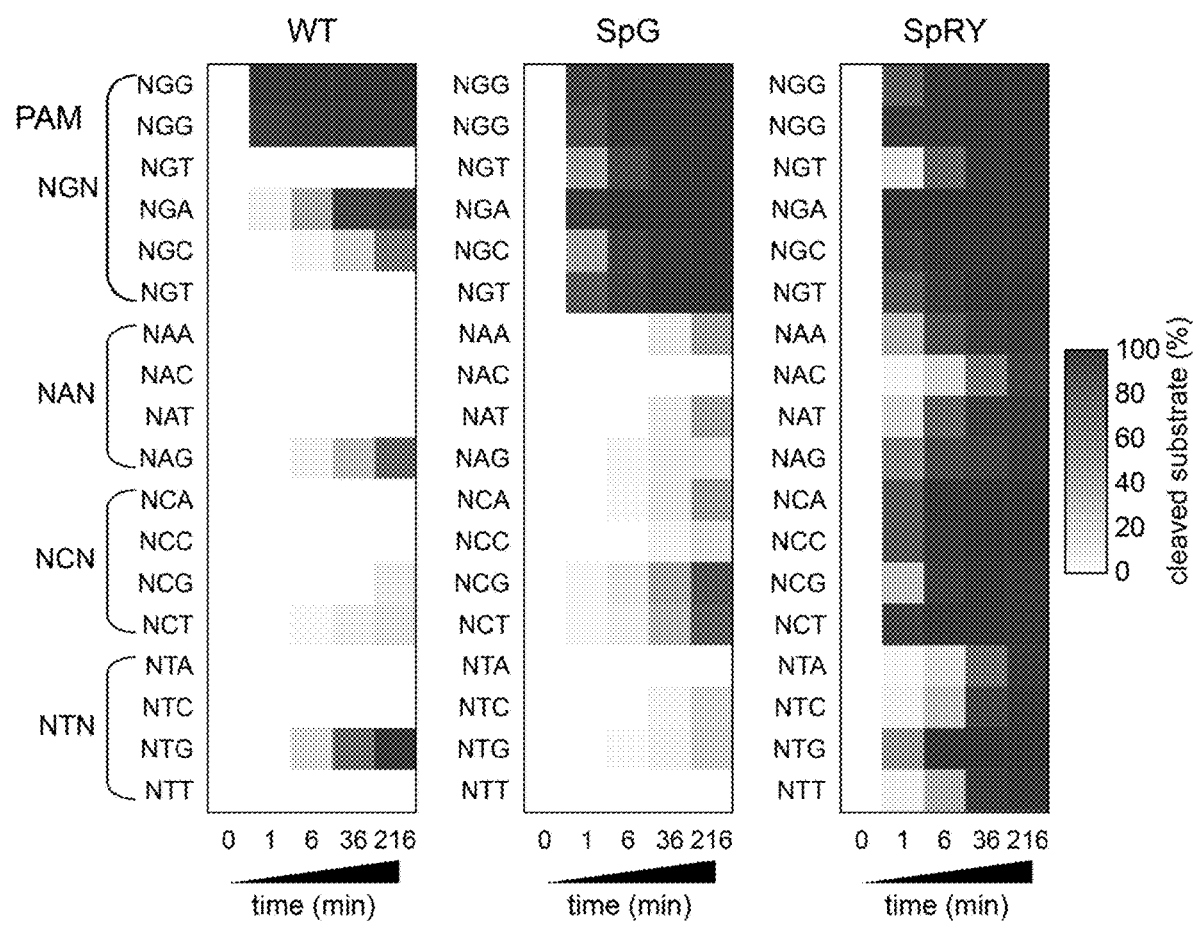

FIG. 20. in vitro digests of DNA substrates using SpCas9 variants. A linearized plasmid DNA was used a substrate for in vitro cleavage reactions with wild-type SpCas9, SpG, or SpRY proteins complexed with various gRNAs targeted to sites in the substrate plasmid harboring different PAMs. Aliquots of the cleavage reactions were stopped at four timepoints (1, 6, 36, and 216 minutes) prior to analysis to determine the percentage of substrate that was cleaved in a site-specific manner. Individual datapoints within the heatmaps are the mean of 3 replicates.

REFERENCES FOR FIGURE LEGENDS

1. Anders, C., Niewoehner, O., Duerst, A. & Jinek, M. Structural basis of PAM-dependent target DNA recognition by the Cas9 endonuclease. Nature 513, 569-73 (2014).
2. Hu, J. H. et al. Evolved Cas9 variants with broad PAM compatibility and high DNA specificity. Nature 556, 57-63 (2018).
3. Nishimasu, H. et al. Engineered CRISPR-Cas9 nuclease with expanded targeting space. Science 361, 1259-1262 (2018).
4. Hirano, S., Nishimasu, H., Ishitani, R. & Nureki, O. Structural Basis for the Altered PAM Specificities of Engineered CRISPR-Cas9. Mol Cell 61, 886-94 (2016).
5. Jinek, M. et al. A Programmable Dual-RNA-Guided DNA Endonuclease in Adaptive Bacterial Immunity. Science 337, 816-821 (2012).
6. Jiang, W., Bikard, D., Cox, D., Zhang, F. & Marraffini, L. A. RNA-guided editing of bacterial genomes using CRISPR-Cas systems. Nat Biotechnol 31, 233-9 (2013).
7. Kleinstiver, B. P. et al. Engineered CRISPR-Cas9 nucleases with altered PAM specificities. Nature 523, 481-5 (2015).
8. Suzuki, K. et al. In vivo genome editing via CRISPR/Cas9 mediated homology-independent targeted integration. Nature 540, 144-149 (2016).
9. Wu, Y. et al. Highly efficient therapeutic gene editing of human hematopoietic stem cells. Nat Med 25, 776-783 (2019).

10. Kleinstiver, B. P. et al. High-fidelity CRISPR-Cas9 nucleases with no detectable genome-wide off-target effects. Nature 529, 490-5 (2016).

DETAILED DESCRIPTION

One method to improve the targeting range of genome editing technologies is to purposefully engineer CRISPR enzymes that can target previously inaccessible PAMs. SpCas9 primarily recognizes its optimal NGG PAM by direct molecular readout of the guanine DNA bases via the amino acid side chains of R1333 and R1335[20] (FIGS. 1a, 1b and FIG. 5a). Modification of either arginine alone ablates SpCas9 nuclease activity against sites with NGG, NAG, or NGA PAMs[8,20], necessitating the use of molecular evolution to alter PAM preference by mutation of other amino acids in the PAM interacting (PI) domain. Several protein engineering strategies have been pursued towards expanding targeting with SpCas9, including using directed evolution or structure-guided engineering to develop variants with altered PAM profiles[8,21] (e.g. SpCas9-VQR, VRQR, and VRER) or relaxed PAM preferences[22,23] (e.g. SpCas9-NG and xCas9). While these variants expand the potential targeting space of SpCas9, target sites encoding the majority of non-canonical PAMs still remain inaccessible for genome editing.

Here we describe a protein engineering approach to nearly completely relax the strict PAM requirement of SpCas9. First, we used our previously described SpCas9-VRQR variant[21] (that recognizes NGAN>NGNG PAMs) as a molecular scaffold to engineer a series of new variants capable of targeting sites bearing more divergent PAMs. Rational engineering of SpCas9-VRQR enabled the generation of the most active NGN PAM variant described to-date (named SpG), and subsequent optimization of SpG led to an SpCas9 variant able to edit nearly all PAMs (named SpRY). SpRY mediates robust nuclease, cytosine base editor, and adenine base editor activities on sites with NRN PAMs and can also target sites with NYN PAMs, albeit at a reduced relative efficiency. We demonstrate that SpG and the nearly unconstrained targeting of SpRY significantly improve editing resolution, offering new genome editing capabilities for applications that require highly accurate editing, including for base editing and the introduction of protective genetic single nucleotide polymorphisms (SNPs).

While the PAM requirement of CRISPR systems is a biologically important property that enables bacteria to distinguish self from non-self, for genome editing applications the necessity of PAM recognition constrains use across genomic loci that lack or sparsely encode PAMs. The SpG and SpRY variants described herein circumvent this limitation by relaxing or almost entirely removing the dependence of SpCas9 on a requisite PAM. In doing so, we demonstrate for the first-time the ability to edit endogenous sequences in human cells harboring previously inaccessible NAN, NCN, and NTN PAMs. While we validated the utility of these variants for generating protective genetic SNPs that were previously inaccessible with WT SpCas9, these variants should enable unconstrained targeting for a variety of applications that require the precise position of DNA breaks, nicks, deamination, or binding events (e.g. for interrogating regions of the genome, for conducting CRISPR screens of various compositions, for performing HDR-based edits, for molecular biology, etc.).

In principle, the strategy we utilized to reduce or eliminate the PAM requirement should be applicable to other CRISPR-Cas9 and -Cas12a orthologs for which there is structural information, and for those that have previously been amenable to PAM engineering. Without wishing to be bound by theory, we speculate that SpRY achieves its expanded targeting range through a combination of mechanism: the removal of the canonical base-specific interactions that are instead supported by a combination of variable base-specific interactions depending on PAM sequence context, displacement of the PAM DNA to facilitate interactions in the major groove of the PAM, and energetic compensation by the addition of novel non-specific protein: DNA contacts. More practically, when contemplating which enzyme to utilize for experiments when on-target activity is the primary objective, we suggest utilizing WT SpCas9 for sites harboring NGG PAMs, SpG for NGH PAMs, and SpRY for targets encoding the remaining NHN PAMs (with NAN>NCN/NTN).

A primary consideration for genome editing applications is the potential for undesirable off-target effects and methods to mitigate them. As we and others have previously observed when developing engineered CRISPR-Cas12a and -Cas9 enzymes with expanded PAM tolerances, relaxation of the PAM can reduce specificity[22,36]. However, both enAsCas12a and SpCas9-NG were compatible with substitutions to enhance genome-wide specificity, improving the safety profiles of these enzymes. With SpG and SpRY we found that they were compatible with SpCas9-HF1 substitutions previously shown to eliminate off-target effects[21] (FIG. 15), demonstrating a path towards more specific editing with these enzymes for applications that require higher fidelity.

In summary, by using protein engineering to eliminate a fundamental biological constraint of CRISPR-Cas enzymes, we developed SpCas9 variants capable of high-resolution editing for various applications. With SpRY supporting the editing of many sites containing NRN>NYN PAMs, the vast majority of the genome is now targetable.

Engineered Cas9 Variants with Altered PAM Specificities

The SpCas9 variants engineered in this study greatly increase the range of target sites accessible by wild-type SpCas9, further enhancing the opportunities to use the CRISPR-Cas9 platform, e.g., to practice efficient HDR, to target NHEJ-mediated indels to small genetic elements, and to exploit the requirement for a PAM to distinguish between two different alleles in the same cell. The selection and rational design of variants that can now target formerly inaccessible sites and improve the prospects for accurate and high-resolution genome-editing. The altered PAM specificity SpCas9 variants can efficiently disrupt endogenous gene sites that are not currently targetable by SpCas9 in both bacterial and human cells, suggesting that they will work in a variety of different cell types and organisms.

All of the SpCas9 variants described herein can be rapidly incorporated into existing and widely used vectors, e.g., by simple site-directed mutagenesis, and because they require only a small number of mutations contained within the PAM-interacting domain, the variants should also work with other previously described improvements to the SpCas9 platform (e.g., truncated sgRNAs (Tsai et al., Nat Biotechnol 33, 187-197 (2015); Fu et al., Nat Biotechnol 32, 279-284 (2014)), nickase mutations (Mali et al., Nat Biotechnol 31, 833-838 (2013); Ran et al., Cell 154, 1380-1389 (2013)), dimeric FokI-dCas9 fusions (Guilinger et al., Nat Biotechnol 32, 577-582 (2014); Tsai et al., Nat Biotechnol 32, 569-576 (2014)); and high-fidelity variants (Kleinstiver et al. Nature 2016).

SpCas9 Variants

Thus, provided herein are SpCas9 variants. The SpCas9 wild type sequence is as follows:

```
                                          (SEQ ID NO: 1)
          10         20         30         40
    MDKKYSIGLD IGTNSVGWAV ITDEYKVPSK KFKVLGNTDR 50         60         70         80
    HSIKKNLIGA LLFDSGETAE ATRLKRTARR RYTRRKNRIC 90        100        110        120
    YLQEIFSNEM AKVDDSFFHR LEESFLVEED KKHERHPIFG 130        140        150        160
    NIVDEVAYHE KYPTIYHLRK KLVDSTDKAD LRLIYLALAH 170        180        190        200
    MIKFRGHFLI EGDLNPDNSD VDKLFIQLVQ TYNQLFEENP 210        220        230        240
    INASGVDAKA ILSARLSKSR RLENLIAQLP GEKKNGLFGN 250        260        270        280
    LIALSLGLTP NFKSNFDLAE DAKLQLSKDT YDDDLDNLLA 290        300        310        320
    QIGDQYADLF LAAKNLSDAI LLSDILRVNT EITKAPLSAS 330        340        350        360
    MIKRYDEHHQ DLTLLKALVR QQLPEKYKEI FFDQSKNGYA 370        380        390        400
    GYIDGGASQE EFYKFIKPIL EKMDGTEELL VKLNREDLLR 410        420        430        440
    KQRTFDNGSI PHQIHLGELH AILRRQEDFY PFLKDNREKI 450        460        470        480
    EKILTFRIPY YVGPLARGNS RFAWMTRKSE ETITPWNFEE 490        500        510        520
    VVDKGASAQS FIERMTNFDK NLPNEKVLPK HSLLYEYFTV 530        540        550        560
    YNELTKVKYV TEGMRKPAFL SGEQKKAIVD LLFKTNRKVT 570        580        590        600
    VKQLKEDYFK KIECFDSVEI SGVEDRFNAS LGTYHDLLKI 610        620        630        640
    IKDKDFLDNE ENEDILEDIV LTLTLFEDRE MIEERLKTYA 650        660        670        680
    HLFDDKVMKQ LKRRRYTGWG RLSRKLINGI RDKQSGKTIL 690        700        710        720
    DFLKSDGFAN RNFMQLIHDD SLTFKEDIQK AQVSGQGDSL 730        740        750        760
    HEHIANLAGS PAIKKGILQT VKVVDELVKV MGRHKPENIV 770        780        790        800
    IEMARENQTT QKGQKNSRER MKRIEEGIKE LGSQILKEHP 810        820        830        840
    VENTQLQNEK LYLYYLQNGR DMYVDQELDI NRLSDYDVDH 850        860        870        880
    IVPQSFLKDD SIDNKVLTRS DKNRGKSDNV PSEEVVKKMK 890        900        910        920
    NYWRQLLNAK LITQRKFDNL TKAERGGLSE LDKAGFIKRQ 930        940        950        960
    LVETRQITKH VAQILDSRMN TKYDENDKLI REVKVITLKS 970        980        990       1000
    KLVSDFRKDF QFYKVREINN YHHAHDAYLN AVVGTALIKK 1010       1020       1030       1040
    YPKLESEFVY GDYKVYDVRK MIAKSEQEIG KATAKYFFYS 1050       1060       1070       1080
    NIMNFFKTEI TLANGEIRKR PLIETNGETG EIVWDKGRDF 1090       1100       1110       1120
    ATVRKVLSMP QVNIVKKTEV QTGGFSKESI LPKRNSDKLI 1130       1140       1150       1160
    ARKKDWDPKK YGGFDSPTVA YSVLVVAKVE KGKSKKLKSV 1170       1180       1190       1200
    KELLGITIME RSSFEKNPID FLEAKGYKEV KKDLIIKLPK 1210       1220       1230       1240
    YSLFELENGR KRMLASAGEL QKGNELALPS KYVNFLYLAS 1250       1260       1270       1280
    HYEKLKGSPE DNEQKQLFVE QHKHYLDEII EQISEFSKRV 1290       1300       1310       1320
    ILADANLDKV LSAYNKHRDK PIREQAENII HLFTLTNLGA 1330       1340       1350       1360
    PAAFKYFDTT IDRKRYTSTK EVLDATLIHQ SITGLYETRI

DLSQLGGD
```

The SpCas9 variants described herein can include mutations at one, two, three, four, five, or all six of the following positions: at E1219X (e.g., E to Q/H/S/V); S1136X (e.g., S to W/F/A/V); D1135X (e.g., D to L/A/W/F); G1218X (e.g., G to R/K/S); R1335X (e.g., R to Q); and/or T1337X (e.g., T to R/K), where X is any amino acid (or at positions analogous thereto). In some embodiments, the SpCas9 variants are at least 80%, e.g., at least 85%, 90%, or 95% identical to the amino acid sequence of SEQ ID NO:1, e.g., have differences at up to 5%, 10%, 15%, or 20% of the residues of SEQ ID NO: 1 replaced, e.g., with conservative mutations. In preferred embodiments, the variant retains desired activity of the parent, e.g., the nuclease activity (except where the parent is a nickase or a dead Cas9), and/or the ability to interact with a guide RNA and target DNA).

To determine the percent identity of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90% or 100%. The nucleotides at corresponding amino acid positions or nucleotide positions are then compared. When a position in the first sequence is occupied by the same nucleotide as the corresponding position in the second sequence, then the molecules are identical at that position (as used herein nucleic acid "identity" is equivalent to nucleic acid "homology"). The percent identity between the two sequences is a function of the number of identical positions shared by the sequences, taking into account the number of gaps, and the length of each gap, which need to be introduced for optimal alignment of the two sequences. Percent identity between two polypeptides or nucleic acid sequences is determined in various ways that are within the skill in the art, for instance, using publicly available computer software such as Smith Waterman Alignment (Smith, T. F. and M. S. Waterman (1981) J Mol Biol 147:195-7); "BestFit" (Smith and Waterman, Advances in Applied Mathematics, 482-489 (1981)) as incorporated into GeneMatcher Plus™, Schwarz and Dayhof (1979) Atlas of Protein Sequence and Structure, Dayhof, M. O., Ed, pp 353-358; BLAST program (Basic Local Alignment Search Tool; (Altschul, S. F., W. Gish, et al. (1990) J Mol Biol 215:403-10), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the length of the sequences being compared. In general, for proteins or nucleic acids, the length of comparison can be any length, up to and including full length (e.g., 5%, 10%, 20%, 30%, 40%, 50%, 60%, 70%, 80%, 90%, 95%, or 100%). For purposes of the present compositions and methods, at least 80% of the full length of the sequence is aligned using the BLAST algorithm and the default parameters.

For purposes of the present invention, the comparison of sequences and determination of percent identity between two sequences can be accomplished using a Blossum 62 scoring matrix with a gap penalty of 12, a gap extend penalty of 4, and a frameshift gap penalty of 5.

Conservative substitutions typically include substitutions within the following groups: glycine, alanine; valine, iso-leucine, leucine; aspartic acid, glutamic acid, asparagine, glutamine; serine, threonine; lysine, arginine; and phenyl-alanine, tyrosine.

In some embodiments, the SpCas9 variant is a variant with NGN PAM preference, e.g., that includes a set of mutations shown in Tables 1, e.g., a set of mutations at E1219 (e.g., E to Q/H/S/V); S1136 (e.g., S to W/F/A/V); D1135 (e.g., D to L/A/W/F); G1218 (e.g., G to R/K/S); R1335 (e.g., R to Q); and/or T1337 (e.g., T to R/K).

TABLE 1

Engineering SpG (variants with NGN PAM preference)

| short name* | Full substitutions description |
|---|---|
| LWKQQR ("SpG") | D1135L/S1136W/G1218K/E1219Q/R1335Q/T1337R |
| LWRQQR | D1135L/S1136W/G1218R/E1219Q/R1335Q/T1337R |
| LWSQQR | D1135L/S1136W/G1218S/E1219Q/R1335Q/T1337R |
| LWKHQR | D1135L/S1136W/G1218K/E1219H/R1335Q/T1337R |
| LWKSQR | D1135L/S1136W/G1218K/E1219S/R1335Q/T1337R |
| LWRSQR | D1135L/S1136W/G1218R/E1219S/R1335Q/T1337R |
| LWRSQK | D1135L/S1136W/G1218R/E1219S/R1335Q/T1337K |
| LWSHQR | D1135L/S1136W/G1218S/E1219H/R1335Q/T1337R |
| LWRHQR | D1135L/S1136W/G1218R/E1219H/R1335Q/T1337R |
| LWRQQK | D1135L/S1136W/G1218R/E1219Q/R1335Q/T1337K |
| LWSQQK | D1135L/S1136W/G1218S/E1219Q/R1335Q/T1337K |
| LSKQQR | D1135L/S1136/G1218K/E1219Q/R1335Q/T1337R |
| LWKQQK | D1135L/S1136W/G1218K/E1219Q/R1335Q/T1337K |

TABLE 1-continued

Engineering SpG (variants with NGN PAM preference)

| short name* | Full substitutions description |
|---|---|
| LSKHQR | D1135L/S1136/G1218K/E1219H/R1335Q/T1337R |
| LWKSQK | D1135L/S1136W/G1218K/E1219S/R1335Q/T1337K |
| LSRHQR | D1135L/S1136/G1218R/E1219H/R1335Q/T1337R |
| LWRVQK | D1135L/S1136W/G1218R/E1219V/R1335Q/T1337K |
| LFRQQR | D1135L/S1136F/G1218R/E1219Q/R1335Q/T1337R |
| LSRQQR | D1135L/S1136/G1218R/E1219Q/R1335Q/T1337R |
| LSRHQR | D1135L/S1136/G1218R/E1219H/R1335Q/T1337R |
| LSRSQR | D1135L/S1136/G1218R/E1219S/R1335Q/T1337R |
| LARQQR | D1135L/S1136A/G1218R/E1219Q/R1335Q/T1337R |
| LSRVQR | D1135L/S1136/G1218R/E1219V/R1335Q/T1337R |
| ASREQR | D1135A/S1136/G1218R/E1219E/R1335Q/T1337R |
| WSREQR | D1135W/S1136/G1218R/E1219E/R1335Q/T1337R |
| LSREQR | D1135L/S1136/G1218R/E1219E/R1335Q/T1337R |
| FSREQR | D1135F/S1136/G1218R/E1219E/R1335Q/T1337R |
| LSRQQR | D1135L/S1136/G1218R/E1219Q/R1335Q/T1337R |
| LSKSQR | D1135L/S1136/G1218K/E1219S/R1335Q/T1337R |
| LWKVQK | D1135L/S1136W/G1218K/E1219V/R1335Q/T1337K |
| LWKHQK | D1135L/S1136W/G1218K/E1219H/R1335Q/T1337K |
| LWSSQK | D1135L/S1136W/G1218S/E1219S/R1335Q/T1337K |
| LWSHQK | D1135L/S1136W/G1218S/E1219H/R1335Q/T1337K |
| LWSSQR | D1135L/S1136W/G1218S/E1219S/R1335Q/T1337R |
| LSRSQR | D1135L/S1136/G1218R/E1219S/R1335Q/T1337R |
| LWRVQR | D1135L/S1136W/G1218R/E1219V/R1335Q/T1337R |
| LSKVQR | D1135L/S1136/G1218K/E1219V/R1335Q/T1337R |
| LWRHQK | D1135L/S1136W/G1218R/E1219H/R1335Q/T1337K |
| LSSQQR | D1135L/S1136/G1218S/E1219Q/R1335Q/T1337R |
| LWKVQR | D1135L/S1136W/G1218K/E1219V/R1335Q/T1337R |
| LSRVQR | D1135L/S1136/G1218R/E1219V/R1335Q/T1337R |
| LWSVQK | D1135L/S1136W/G1218S/E1219V/R1335Q/T1337K |
| LSSHQR | D1135L/S1136/G1218S/E1219H/R1335Q/T1337R |
| LWSVQR | D1135L/S1136W/G1218S/E1219V/R1335Q/T1337R |
| LSSVQR | D1135L/S1136/G1218S/E1219V/R1335Q/T1337R |
| LSKQQK | D1135L/S1136/G1218K/E1219Q/R1335Q/T1337K |
| LSRVQK | D1135L/S1136/G1218R/E1219V/R1335Q/T1337K |
| LSKVQK | D1135L/S1136/G1218K/E1219V/R1335Q/T1337K |
| LSSSQR | D1135L/S1136/G1218S/E1219S/R1335Q/T1337R |
| LSKSQK | D1135L/S1136/G1218K/E1219S/R1335Q/T1337K |
| LSSVQK | D1135L/S1136/G1218S/E1219V/R1335Q/T1337K |
| LSRQQK | D1135L/S1136/G1218R/E1219Q/R1335Q/T1337K |
| LSSQQK | D1135L/S1136/G1218S/E1219Q/R1335Q/T1337K |
| LSRSQK | D1135L/S1136/G1218R/E1219S/R1335Q/T1337K |
| LSKHQK | D1135L/S1136/G1218K/E1219H/R1335Q/T1337K |

*short name based on identities at D1135, S1136, G1218, E1219, R1335, T1337

In some embodiments, the SpCas9 variant is a variant with NRN>NYN PAM preference, e.g., that includes a set of mutations shown in Table 1, e.g., a set of mutations at E1219 (e.g., E to Q/H/S/V); S1136 (e.g., S to W/F/[S]/A/V); D1135 (e.g., D to L/A/W/F); G1218 (e.g., G to R/K/S); R1335 (e.g., R to Q); and/or T1337 (e.g., T to R/K), and a mutation in R1333 (e.g., R to P/C/A/V/G/K/L/S/T/Y/Q/I/H/N/M/D/E/F/W), e.g., as shown in Table 2.

TABLE 2

Engineering SpRY (variants with NRN > NYN PAM preference)-step 1: R1333X substitutions in SpG**

| R1333 substitution | name | Full substitutions description |
|---|---|---|
| R1333P | SpG + R1333P | D1135L/S1136W/G1218K/E1219Q/R1333P/R1335Q/T1337R |
| R1333C | SpG + R1333C | D1135L/S1136W/G1218K/E1219Q/R1333C/R1335Q/T1337R |
| R1333A | SpG + R1333A | D1135L/S1136W/G1218K/E1219Q/R1333A/R1335Q/T1337R |
| R1333V | SpG + R1333V | D1135L/S1136W/G1218K/E1219Q/R1333V/R1335Q/T1337R |
| R1333G | SpG + R1333G | D1135L/S1136W/G1218K/E1219Q/R1333G/R1335Q/T1337R |
| R1333S | SpG + R1333S | D1135L/S1136W/G1218K/E1219Q/R1333S/R1335Q/T1337R |
| R1333T | SpG + R1333T | D1135L/S1136W/G1218K/E1219Q/R1333T/R1335Q/T1337R |
| R1333K | SpG + R1333K | D1135L/S1136W/G1218K/E1219Q/R1333K/R1335Q/T1337R |
| R1333L | SpG + R1333L | D1135L/S1136W/G1218K/E1219Q/R1333L/R1335Q/T1337R |
| R1333Y | SpG + R1333Y | D1135L/S1136W/G1218K/E1219Q/R1333Y/R1335Q/T1337R |

TABLE 2-continued

Engineering SpRY (variants with NRN > NYN PAM preference)-step 1:
R1333X substitutions in SpG**

| R1333 substitution | name | Full substitutions description |
|---|---|---|
| R1333Q | SpG + R1333Q | D1135L/S1136W/G1218K/E1219Q/R1333Q/R1335Q/T1337R |
| R1333I | SpG + R1333I | D1135L/S1136W/G1218K/E1219Q/R1333I/R1335Q/T1337R |
| R1333H | SpG + R1333H | D1135L/S1136W/G1218K/E1219Q/R1333H/R1335Q/T1337R |
| R1333N | SpG + R1333N | D1135L/S1136W/G1218K/E1219Q/R1333N/R1335Q/T1337R |
| R1333M | SpG + R1333M | D1135L/S1136W/G1218K/E1219Q/R1333M/R1335Q/T1337R |
| R1333D | SpG + R1333D | D1135L/S1136W/G1218K/E1219Q/R1333D/R1335Q/T1337R |
| R1333E | SpG + R1333E | D1135L/S1136W/G1218K/E1219Q/R1333E/R1335Q/T1337R |
| R1333F | SpG + R1333F | D1135L/S1136W/G1218K/E1219Q/R1333F/R1335Q/T1337R |
| R1333W | SpG + R1333W | D1135L/S1136W/G1218K/E1219Q/R1333W/R1335Q/T1337R |

**These mutations in R1333 are shown in the context of SpG*, but could be in any other variant from Table 1; SpG has D1135L/S1136W/G1218K/E1219Q/R1335Q/T1337R (LWKQQR) substitutions.

These mutants are referred to herein as LWKQPQR; LWKQCQR; LWKQAQR; LWKQVQR; LWKQGQR; LWKQSQR; LWKQTQR; LWKQKQR; LWKQLQR; LWKQYQR; LWKQQQR; LWKQIQR; LWKQHQR; LWKQNQR; LWKQMQR; LWKQDQR; LWKQEQR; LWKQFQR; and LWKQWQR, respectively.

In some embodiments, the SpCas9 variant is a variant with NRN>NYN PAM preference, e.g., that includes a set of mutations shown in Table 1, e.g., a set of mutations at E1219 (e.g., E to Q/H/S/V); S1136 (e.g., S to W/F/A/V); D1135 (e.g., D to L/A/W/F); G1218 (e.g., G to R/K/S); R1335 (e.g., R to Q); and/or T1337 (e.g., T to R/K), and a mutation in R1333 (e.g., R to P/C/A/V/G/K/L/S/T/Y/Q/I/H/N/M/D/E/F/W), e.g., as shown in Table 2, and one or more on-target activity-increasing ("up-activity") mutations, e.g., at G1104 (e.g., G to K/H/R); A61 (e.g., A to R/K/H); N1317 (e.g. N to R/K/H/Q); L1111 (e.g., L to R/K); and/or A1322 (e.g., A to R/K), e.g., at L1111R or A1322R; see U.S. Ser. No. 62/965,671 (incorporated herein by reference) and Nishimasu et al., Science. 361 (6408): 1259-1262 (2018). In some embodiments the up-activity mutations are made in a SpG+R1333X variant, e.g., SpG+R1333P, SpG+R1333C, SpG+R1333A, SpG+R1333V, SpG+R1333G, or SpG+R1333S variant with any of the single substitutions shown in Table 3.

TABLE 3

Exemplary variants with single up-activity substitution variants

| single up-activity mutation | parental variant | name | Full substitutions description |
|---|---|---|---|
| N1317R | SpG + R1333P | SpG + R1333P + N1317R | D1135L/S1136W/G1218K/E1219Q/R1333P/R1335Q/T1337R/N1317R |
| G1104K | SpG + R1333P | SpG + R1333P + G1104K | D1135L/S1136W/G1218K/E1219Q/R1333P/R1335Q/T1337R/G1104K |
| A61R | SpG + R1333P | SpG + R1333P + A61R | D1135L/S1136W/G1218K/E1219Q/R1333P/R1335Q/T1337R/A61R |
| N1317R | SpG + R1333C | SpG + R1333C + N1317R | D1135L/S1136W/G1218K/E1219Q/R1333C/R1335Q/T1337R/N1317R |
| G1104K | SpG + R1333C | SpG + R1333C + G1104K | D1135L/S1136W/G1218K/E1219Q/R1333C/R1335Q/T1337R/G1104K |
| A61R | SpG + R1333C | SpG + R1333C + A61R | D1135L/S1136W/G1218K/E1219Q/R1333C/R1335Q/T1337R/A61R |
| N1317R | SpG + R1333A | SpG + R1333A + N1317R | D1135L/S1136W/G1218K/E1219Q/R1333A/R1335Q/T1337R/N1317R |
| G1104K | SpG + R1333A | SpG + R1333A + G1104K | D1135L/S1136W/G1218K/E1219Q/R1333A/R1335Q/T1337R/G1104K |
| A61R | SpG + R1333A | SpG + R1333A + A61R | D1135L/S1136W/G1218K/E1219Q/R1333A/R1335Q/T1337R/A61R |
| L1111R | SpG + R1333P | SpG + R1333P + L1111R | D1135L/S1136W/G1218K/E1219Q/R1333P/R1335Q/T1337R/L1111R |
| A1322R | SpG + R1333P | SpG + R1333P + A1322R | D1135L/S1136W/G1218K/E1219Q/R1333P/R1335Q/T1337R/A1322R |
| L1111R | SpG + R1333C | SpG + R1333C + L1111R | D1135L/S1136W/G1218K/E1219Q/R1333C/R1335Q/T1337R/L1111R |
| A1322R | SpG + R1333C | SpG + R1333C + A1322R | D1135L/S1136W/G1218K/E1219Q/R1333C/R1335Q/T1337R/A1322R |
| L1111R | SpG + R1333A | SpG + R1333A + L1111R | D1135L/S1136W/G1218K/E1219Q/R1333A/R1335Q/T1337R/L1111R |
| A1322R | SpG + R1333A | SpG + R1333A + A1322R | D1135L/S1136W/G1218K/E1219Q/R1333A/R1335Q/T1337R/A1322R |
| N1317K | SpG + R1333P | SpG + R1333P + N1317K | D1135L/S1136W/G1218K/E1219Q/R1333P/R1335Q/T1337R/N1317K |

TABLE 3-continued

Exemplary variants with single up-activity substitution variants

| single up-activity mutation | parental variant | name | Full substitutions description |
|---|---|---|---|
| N1317H | SpG + R1333P | SpG + R1333P + N1317H | D1135L/S1136W/G1218K/E1219Q/R1333P/R1335Q/T1337R/N1317H |
| A61K | SpG + R1333P | SpG + R1333P + A61K | D1135L/S1136W/G1218K/E1219Q/R1333P/R1335Q/T1337R/A61K |
| A61H | SpG + R1333P | SpG + R1333P + A61H | D1135L/S1136W/G1218K/E1219Q/R1333P/R1335Q/T1337R/A61H |
| N1317K | SpG + R1333C | SpG + R1333C + N1317K | D1135L/S1136W/G1218K/E1219Q/R1333C/R1335Q/T1337R/N1317K |
| N1317H | SpG + R1333C | SpG + R1333C + N1317H | D1135L/S1136W/G1218K/E1219Q/R1333C/R1335Q/T1337R/N1317H |
| A61K | SpG + R1333C | SpG + R1333C + A61K | D1135L/S1136W/G1218K/E1219Q/R1333C/R1335Q/T1337R/A61K |
| A61H | SpG + R1333C | SpG + R1333C + A61H | D1135L/S1136W/G1218K/E1219Q/R1333C/R1335Q/T1337R/A61H |
| N1317K | SpG + R1333A | SpG + R1333A + N1317K | D1135L/S1136W/G1218K/E1219Q/R1333A/R1335Q/T1337R/N1317K |
| N1317H | SpG + R1333A | SpG + R1333A + N1317H | D1135L/S1136W/G1218K/E1219Q/R1333A/R1335Q/T1337R/N1317H |
| A61K | SpG + R1333A | SpG + R1333A + A61K | D1135L/S1136W/G1218K/E1219Q/R1333A/R1335Q/T1337R/A61K |
| A61H | SpG + R1333A | SpG + R1333A + A61H | D1135L/S1136W/G1218K/E1219Q/R1333A/R1335Q/T1337R/A61H |
| G1104H | SpG + R1333P | SpG + R1333P + G1104H | D1135L/S1136W/G1218K/E1219Q/R1333P/R1335Q/T1337R/G1104H |
| L1111K | SpG + R1333P | SpG + R1333P + L1111K | D1135L/S1136W/G1218K/E1219Q/R1333P/R1335Q/T1337R/L1111K |
| A1322K | SpG + R1333P | SpG + R1333P + A1322K | D1135L/S1136W/G1218K/E1219Q/R1333P/R1335Q/T1337R/A1322K |
| L1111H | SpG + R1333P | SpG + R1333P + L1111H | D1135L/S1136W/G1218K/E1219Q/R1333P/R1335Q/T1337R/L1111H |
| A1322H | SpG + R1333P | SpG + R1333P + A1322H | D1135L/S1136W/G1218K/E1219Q/R1333P/R1335Q/T1337R/A1322H |
| G1104R | SpG + R1333P | SpG + R1333P + G1104R | D1135L/S1136W/G1218K/E1219Q/R1333P/R1335Q/T1337R/G1104R |
| G1104H | SpG + R1333C | SpG + R1333C + G1104H | D1135L/S1136W/G1218K/E1219Q/R1333C/R1335Q/T1337R/G1104H |
| L1111K | SpG + R1333C | SpG + R1333C + L1111K | D1135L/S1136W/G1218K/E1219Q/R1333C/R1335Q/T1337R/L1111K |
| A1322K | SpG + R1333C | SpG + R1333C + A1322K | D1135L/S1136W/G1218K/E1219Q/R1333C/R1335Q/T1337R/A1322K |
| L1111H | SpG + R1333C | SpG + R1333C + L1111H | D1135L/S1136W/G1218K/E1219Q/R1333C/R1335Q/T1337R/L1111H |
| A1322H | SpG + R1333C | SpG + R1333C + A1322H | D1135L/S1136W/G1218K/E1219Q/R1333C/R1335Q/T1337R/A1322H |
| G1104R | SpG + R1333C | SpG + R1333C + G1104R | D1135L/S1136W/G1218K/E1219Q/R1333C/R1335Q/T1337R/G1104R |
| G1104H | SpG + R1333A | SpG + R1333A + G1104H | D1135L/S1136W/G1218K/E1219Q/R1333A/R1335Q/T1337R/G1104H |
| L1111K | SpG + R1333A | SpG + R1333A + L1111K | D1135L/S1136W/G1218K/E1219Q/R1333A/R1335Q/T1337R/L1111K |
| A1322K | SpG + R1333A | SpG + R1333A + A1322K | D1135L/S1136W/G1218K/E1219Q/R1333A/R1335Q/T1337R/A1322K |
| L1111H | SpG + R1333A | SpG + R1333A + L1111H | D1135L/S1136W/G1218K/E1219Q/R1333A/R1335Q/T1337R/L1111H |
| A1322H | SpG + R1333A | SpG + R1333A + A1322H | D1135L/S1136W/G1218K/E1219Q/R1333A/R1335Q/T1337R/A1322H |
| G1104R | SpG + R1333A | SpG + R1333A + G1104R | D1135L/S1136W/G1218K/E1219Q/R1333A/R1335Q/T1337R/G1104R |

TABLE 4

Exemplary variants with combinations of up-activity substitution variants

| combinations of up-activity mutations | parental variant | name |
|---|---|---|
| A61R + N1317R | SpG + R1333P | SpG + R1333P + A61R + N1317R |
| G1104K + N1317R | SpG + R1333P | SpG + R1333P + G1104K + N1317R |

TABLE 4-continued

Exemplary variants with combinations of up-activity substitution variants

| combinations of up-activity mutations | parental variant | name |
|---|---|---|
| A61R + G1104K | SpG + R1333P | SpG + R1333P + A61R + G1104K |
| A61R + G1104K + N1317R | SpG + R1333P | SpG + R1333P + A61R + G1104K + N1317R |
| N1317R + L1111R | SpG + R1333P + L1111R | SpG + R1333P + N1317R + L1111R |
| G1104K + L1111R | SpG + R1333P + L1111R | SpG + R1333P + G1104K + L1111R |
| A61R + L1111R | SpG + R1333P + L1111R | SpG + R1333P + A61R + L1111R |
| A61R + N1317R + L1111R | SpG + R1333P + L1111R | SpG + R1333P + A61R + N1317R + L1111R |
| G1104K + N1317R + L1111R | SpG + R1333P + L1111R | SpG + R1333P + G1104K + N1317R + L1111R |
| A61R + G1104K + L1111R | SpG + R1333P + L1111R | SpG + R1333P + A61R + G1104K + L1111R |
| A61R + G1104K + N1317R + L1111R | SpG + R1333P + L1111R | SpG + R1333P + A61R + G1104K + N1317R + L1111R |
| N1317R + A1322R | SpG + R1333P + A1322R | SpG + R1333P + N1317R + A1322R |
| G1104K + A1322R | SpG + R1333P + A1322R | SpG + R1333P + G1104K + A1322R |
| A61R + A1322R | SpG + R1333P + A1322R | SpG + R1333P + A61R + A1322R |
| A61R + N1317R + A1322R | SpG + R1333P + A1322R | SpG + R1333P + A61R + N1317R + A1322R |
| G1104K + N1317R + A1322R | SpG + R1333P + A1322R | SpG + R1333P + G1104K + N1317R + A1322R |
| A61R + G1104K + A1322R | SpG + R1333P + A1322R | SpG + R1333P + A61R + G1104K + A1322R |
| A61R + G1104K + N1317R + A1322R | SpG + R1333P + A1322R | SpG + R1333P + A61R + G1104K + N1317R + A1322R |
| N1317R + L1111R + A1322R | SpG + R1333P + L1111R + A1322R | SpG + R1333P + N1317R + L1111R + A1322R |
| G1104K + L1111R + A1322R | SpG + R1333P + L1111R + A1322R | SpG + R1333P + G1104K + L1111R + A1322R |
| A61R + L1111R + A1322R | SpG + R1333P + L1111R + A1322R | SpG + R1333P + A61R + L1111R + A1322R |
| A61R + N1317R + L1111R + A1322R | SpG + R1333P + L1111R + A1322R | SpG + R1333P + A61R + N1317R + L1111R + A1322R |
| G1104K + N1317R + L1111R + A1322R | SpG + R1333P + L1111R + A1322R | SpG + R1333P + G1104K + N1317R + L1111R + A1322R |
| A61R + G1104K + L1111R + A1322R | SpG + R1333P + L1111R + A1322R | SpG + R1333P + A61R + G1104K + L1111R + A1322R |
| A61R + G1104K + N1317R + L1111R + A1322R | SpG + R1333P + L1111R + A1322R | SpG + R1333P + A61R + G1104K + N1317R + L1111R + A1322R |
| A61R + N1317R | SpG + R1333C | SpG + R1333C + A61R + N1317R |
| G1104K + N1317R | SpG + R1333C | SpG + R1333C + G1104K + N1317R |
| A61R + G1104K | SpG + R1333C | SpG + R1333C + A61R + G1104K |
| A61R + G1104K + N1317R | SpG + R1333C | SpG + R1333C + A61R + G1104K + N1317R |
| N1317R + L1111R | SpG + R1333C + L1111R | SpG + R1333C + N1317R + L1111R |
| G1104K + L1111R | SpG + R1333C + L1111R | SpG + R1333C + G1104K + L1111R |
| A61R + L1111R | SpG + R1333C + L1111R | SpG + R1333C + A61R + L1111R |
| A61R + N1317R + L1111R | SpG + R1333C + L1111R | SpG + R1333C + A61R + N1317R + L1111R |
| G1104K + N1317R + L1111R | SpG + R1333C + L1111R | SpG + R1333C + G1104K + N1317R + L1111R |
| A61R + G1104K + L1111R | SpG + R1333C + L1111R | SpG + R1333C + A61R + G1104K + L1111R |
| A61R + G1104K + N1317R + L1111R | SpG + R1333C + L1111R | SpG + R1333C + A61R + G1104K + N1317R + L1111R |
| N1317R + A1322R | SpG + R1333C + A1322R | SpG + R1333C + N1317R + A1322R |
| G1104K + A1322R | SpG + R1333C + A1322R | SpG + R1333C + G1104K + A1322R |
| A61R + A1322R | SpG + R1333C + A1322R | SpG + R1333C + A61R + A1322R |
| A61R + N1317R + A1322R | SpG + R1333C + A1322R | SpG + R1333C + A61R + N1317R + A1322R |
| G1104K + N1317R + A1322R | SpG + R1333C + A1322R | SpG + R1333C + G1104K + N1317R + A1322R |
| A61R + G1104K + A1322R | SpG + R1333C + A1322R | SpG + R1333C + A61R + G1104K + A1322R |
| A61R + G1104K + N1317R + A1322R | SpG + R1333C + A1322R | SpG + R1333C + A61R + G1104K + N1317R + A1322R |
| N1317R + L1111R + A1322R | SpG + R1333C + L1111R + A1322R | SpG + R1333C + N1317R + L1111R + A1322R |
| G1104K + L1111R + A1322R | SpG + R1333C + L1111R + A1322R | SpG + R1333C + G1104K + L1111R + A1322R |
| A61R + L1111R + A1322R | SpG + R1333C + L1111R + A1322R | SpG + R1333C + A61R + L1111R + A1322R |
| A61R + N1317R + L1111R + A1322R | SpG + R1333C + L1111R + A1322R | SpG + R1333C + A61R + N1317R + L1111R + A1322R |

TABLE 4-continued

Exemplary variants with combinations of up-activity substitution variants

| combinations of up-activity mutations | parental variant | name |
|---|---|---|
| G1104K + N1317R + L1111R + A1322R | SpG + R1333C + L1111R + A1322R | SpG + R1333C + G1104K + N1317R + L1111R + A1322R |
| A61R + G1104K + L1111R + A1322R | SpG + R1333C + L1111R + A1322R | SpG + R1333C + A61R + G1104K + L1111R + A1322R |
| A61R + G1104K + N1317R + L1111R + A1322R | SpG + R1333C + L1111R + A1322R | SpG + R1333C + A61R + G1104K + N1317R + L1111R + A1322R |
| A61R + N1317R | SpG + R1333A | SpG + R1333A + A61R + N1317R |
| G1104K + N1317R | SpG + R1333A | SpG + R1333A + G1104K + N1317R |
| A61R + G1104K | SpG + R1333A | SpG + R1333A + A61R + G1104K |
| A61R + G1104K + N1317R | SpG + R1333A | SpG + R1333A + A61R + G1104K + N1317R |
| N1317R + L1111R | SpG + R1333A + L1111R | SpG + R1333A + N1317R + L1111R |
| G1104K + L1111R | SpG + R1333A + L1111R | SpG + R1333A + G1104K + L1111R |
| A61R + L1111R | SpG + R1333A + L1111R | SpG + R1333A + A61R + L1111R |
| A61R + N1317R + L1111R | SpG + R1333A + L1111R | SpG + R1333A + A61R + N1317R + L1111R |
| G1104K + N1317R + L1111R | SpG + R1333A + L1111R | SpG + R1333A + G1104K + N1317R + L1111R |
| A61R + G1104K + L1111R | SpG + R1333A + L1111R | SpG + R1333A + A61R + G1104K + L1111R |
| A61R + G1104K + N1317R + L1111R | SpG + R1333A + L1111R | SpG + R1333A + A61R + G1104K + N1317R + L1111R |
| N1317R + A1322R | SpG + R1333A + A1322R | SpG + R1333A + N1317R + A1322R |
| G1104K + A1322R | SpG + R1333A + A1322R | SpG + R1333A + G1104K + A1322R |
| A61R + A1322R | SpG + R1333A + A1322R | SpG + R1333A + A61R + A1322R |
| A61R + N1317R + A1322R | SpG + R1333A + A1322R | SpG + R1333A + A61R + N1317R + A1322R |
| G1104K + N1317R + A1322R | SpG + R1333A + A1322R | SpG + R1333A + G1104K + N1317R + A1322R |
| A61R + G1104K + A1322R | SpG + R1333A + A1322R | SpG + R1333A + A61R + G1104K + A1322R |
| A61R + G1104K + N1317R + A1322R | SpG + R1333A + A1322R | SpG + R1333A + A61R + G1104K + N1317R + A1322R |
| N1317R + L1111R + A1322R | SpG + R1333A + L1111R + A1322R | SpG + R1333A + N1317R + L1111R + A1322R |
| G1104K + L1111R + A1322R | SpG + R1333A + L1111R + A1322R | SpG + R1333A + G1104K + L1111R + A1322R |
| A61R + L1111R + A1322R | SpG + R1333A + L1111R + A1322R | SpG + R1333A + A61R + L1111R + A1322R |
| A61R + N1317R + L1111R + A1322R | SpG + R1333A + L1111R + A1322R | SpG + R1333A + A61R + N1317R + L1111R + A1322R |
| G1104K + N1317R + L1111R + A1322R | SpG + R1333A + L1111R + A1322R | SpG + R1333A + G1104K + N1317R + L1111R + A1322R |
| A61R + G1104K + L1111R + A1322R | SpG + R1333A + L1111R + A1322R | SpG + R1333A + A61R + G1104K + L1111R + A1322R |
| A61R + G1104K + N1317R + L1111R + A1322R | SpG + R1333A + L1111R + A1322R | SpG + R1333A + A61R + G1104K + N1317R + L1111R + A1322R |

In some embodiments, the SpCas9 variant comprises mutations at D1135L/S1136W/G1218K/E1219Q/R1333P/R1335Q/T1337R/A61R+N1317R; D1135L/S1136W/G1218K/E1219Q/R1333P/R1335Q/T1337R/G1104K+N1317R; D1135L/S1136W/G1218K/E1219Q/R1333P/R1335Q/T1337R/A61R+G1104K; D1135L/S1136W/G1218K/E1219Q/R1333P/R1335Q/T1337R/A61R+G1104K+N1317R; D1135L/S1136W/G1218K/E1219Q/R1333P/R1335Q/T1337R/N1317R+L1111R; D1135L/S1136W/G1218K/E1219Q/R1333P/R1335Q/T1337R/G1104K+L1111R; D1135L/S1136W/G1218K/E1219Q/R1333P/R1335Q/T1337R/A61R+L1111R; D1135L/S1136W/G1218K/E1219Q/R1333P/R1335Q/T1337R/A61R+N1317R+L1111R; D1135L/S1136W/G1218K/E1219Q/R1333P/R1335Q/T1337R/G1104K+N1317R+L1111R; D1135L/S1136W/G1218K/E1219Q/R1333P/R1335Q/T1337R/A61R+G1104K+L1111R; D1135L/S1136W/G1218K/E1219Q/R1333P/R1335Q/T1337R/A61R+G1104K+N1317R+L1111R; D1135L/S1136W/G1218K/E1219Q/R1333P/R1335Q/T1337R/N1317R+A1322R; D1135L/S1136W/G1218K/E1219Q/R1333P/R1335Q/T1337R/G1104K+A1322R; D1135L/S1136W/G1218K/E1219Q/R1333P/R1335Q/T1337R/A61R+A1322R; D1135L/S1136W/G1218K/E1219Q/R1333P/R1335Q/T1337R/A61R+N1317R+A1322R; D1135L/S1136W/G1218K/E1219Q/R1333P/R1335Q/T1337R/G1104K+N1317R+A1322R; D1135L/S1136W/G1218K/E1219Q/R1333P/R1335Q/T1337R/A61R+G1104K+A1322R; D1135L/S1136W/G1218K/E1219Q/R1333P/R1335Q/T1337R/A61R+G1104K+N1317R+A1322R; D1135L/S1136W/G1218K/E1219Q/R1333P/R1335Q/T1337R/N1317R+L1111R+A1322R; D1135L/S1136W/G1218K/E1219Q/R1333P/R1335Q/T1337R/G1104K+L1111R+A1322R; D1135L/S1136W/G1218K/E1219Q/R1333P/R1335Q/T1337R/A61R+L1111R+A1322R; D1135L/S1136W/G1218K/E1219Q/R1333P/R1335Q/T1337R/A61R+N1317R+L1111R+A1322R; D1135L/S1136W/G1218K/E1219Q/R1333P/R1335Q/T1337R/

G1104K+N1317R+L1111R+A1322R; D1135L/S1136W/G1218K/E1219Q/R1333P/R1335Q/T1337R/A61R+G1104K+L1111R+A1322R; D1135L/S1136W/G1218K/E1219Q/R1333P/R1335Q/T1337R/A61R+G1104K+N1317R+L1111R+A1322R; D1135L/S1136W/G1218K/E1219Q/R1333P/R1335Q/T1337R/A61R+N1317R; D1135L/S1136W/G1218K/E1219Q/R1333P/R1335Q/T1337R/G1104K+N1317R; D1135L/S1136W/G1218K/E1219Q/R1333P/R1335Q/T1337R/A61R+G1104K; D1135L/S1136W/G1218K/E1219Q/R1333P/R1335Q/T1337R/A61R+G1104K+N1317R; D1135L/S1136W/G1218K/E1219Q/R1333P/R1335Q/T1337R/N1317R+L1111R; D1135L/S1136W/G1218K/E1219Q/R1333P/R1335Q/T1337R/G1104K+L1111R; D1135L/S1136W/G1218K/E1219Q/R1333P/R1335Q/T1337R/A61R+L1111R; D1135L/S1136W/G1218K/E1219Q/R1333P/R1335Q/T1337R/A61R+N1317R+L1111R; D1135L/S1136W/G1218K/E1219Q/R1333P/R1335Q/T1337R/G1104K+N1317R+L1111R; D1135L/S1136W/G1218K/E1219Q/R1333P/R1335Q/T1337R/A61R+G1104K+L1111R; D1135L/S1136W/G1218K/E1219Q/R1333P/R1335Q/T1337R/A61R+G1104K+N1317R+L1111R; D1135L/S1136W/G1218K/E1219Q/R1333P/R1335Q/T1337R/N1317R+A1322R; D1135L/S1136W/G1218K/E1219Q/R1333P/R1335Q/T1337R/G1104K+A1322R; D1135L/S1136W/G1218K/E1219Q/R1333P/R1335Q/T1337R/A61R+A1322R; D1135L/S1136W/G1218K/E1219Q/R1333P/R1335Q/T1337R/A61R+N1317R+A1322R; D1135L/S1136W/G1218K/E1219Q/R1333P/R1335Q/T1337R/G1104K+N1317R+A1322R; D1135L/S1136W/G1218K/E1219Q/R1333P/R1335Q/T1337R/A61R+G1104K+A1322R; D1135L/S1136W/G1218K/E1219Q/R1333P/R1335Q/T1337R/A61R+G1104K+N1317R+A1322R; D1135L/S1136W/G1218K/E1219Q/R1333P/R1335Q/T1337R/N1317R+L1111R+A1322R; D1135L/S1136W/G1218K/E1219Q/R1333P/R1335Q/T1337R/G1104K+L1111R+A1322R; D1135L/S1136W/G1218K/E1219Q/R1333P/R1335Q/T1337R/A61R+L1111R+A1322R; D1135L/S1136W/G1218K/E1219Q/R1333P/R1335Q/T1337R/A61R+N1317R+L1111R+A1322R; D1135L/S1136W/G1218K/E1219Q/R1333P/R1335Q/T1337R/G1104K+N1317R+L1111R+A1322R; D1135L/S1136W/G1218K/E1219Q/R1333P/R1335Q/T1337R/A61R+G1104K+L1111R+A1322R; D1135L/S1136W/G1218K/E1219Q/R1333P/R1335Q/T1337R/A61R+G1104K+N1317R+L1111R+A1322R; D1135L/S1136W/G1218K/E1219Q/R1333P/R1335Q/T1337R/A61R+N1317R; D1135L/S1136W/G1218K/E1219Q/R1333P/R1335Q/T1337R/G1104K+N1317R; D1135L/S1136W/G1218K/E1219Q/R1333P/R1335Q/T1337R/A61R+G1104K; D1135L/S1136W/G1218K/E1219Q/R1333P/R1335Q/T1337R/A61R+G1104K+N1317R; D1135L/S1136W/G1218K/E1219Q/R1333P/R1335Q/T1337R/N1317R+L1111R; D1135L/S1136W/G1218K/E1219Q/R1333P/R1335Q/T1337R/G1104K+L1111R; D1135L/S1136W/G1218K/E1219Q/R1333P/R1335Q/T1337R/A61R+L1111R; D1135L/S1136W/G1218K/E1219Q/R1333P/R1335Q/T1337R/A61R+N1317R+L1111R; D1135L/S1136W/G1218K/E1219Q/R1333P/R1335Q/T1337R/G1104K+N1317R+L1111R; D1135L/S1136W/G1218K/E1219Q/R1333P/R1335Q/T1337R/A61R+G1104K+L1111R; D1135L/S1136W/G1218K/E1219Q/R1333P/R1335Q/T1337R/A61R+G1104K+N1317R+L1111R; D1135L/S1136W/G1218K/E1219Q/R1333P/R1335Q/T1337R/N1317R+A1322R; D1135L/S1136W/G1218K/E1219Q/R1333P/R1335Q/T1337R/G1104K+A1322R; D1135L/S1136W/G1218K/E1219Q/R1333P/R1335Q/T1337R/A61R+A1322R; D1135L/S1136W/G1218K/E1219Q/R1333P/R1335Q/T1337R/A61R+N1317R+A1322R; D1135L/S1136W/G1218K/E1219Q/R1333P/R1335Q/T1337R/G1104K+N1317R+A1322R; D1135L/S1136W/G1218K/E1219Q/R1333P/R1335Q/T1337R/A61R+G1104K+A1322R; D1135L/S1136W/G1218K/E1219Q/R1333P/R1335Q/T1337R/A61R+G1104K+N1317R+A1322R; D1135L/S1136W/G1218K/E1219Q/R1333P/R1335Q/T1337R/N1317R+L1111R+A1322R; D1135L/S1136W/G1218K/E1219Q/R1333P/R1335Q/T1337R/G1104K+L1111R+A1322R; D1135L/S1136W/G1218K/E1219Q/R1333P/R1335Q/T1337R/A61R+L1111R+A1322R; D1135L/S1136W/G1218K/E1219Q/R1333P/R1335Q/T1337R/A61R+N1317R+L1111R+A1322R; D1135L/S1136W/G1218K/E1219Q/R1333P/R1335Q/T1337R/G1104K+N1317R+L1111R+A1322R; D1135L/S1136W/G1218K/E1219Q/R1333P/R1335Q/T1337R/A61R+G1104K+L1111R+A1322R; or D1135L/S1136W/G1218K/E1219Q/R1333P/R1335Q/T1337R/A61R+G1104K+N1317R+L1111R+A1322R, which are listed in the order they appear in Table 4.

TABLE 5

| PREFERRED VARIANTS | | |
|---|---|---|
| combinations of up-activity | parental variant | name |
| A61R + N1317R + L1111R + A1322R | SpG + R1333P + L1111R + A1322R | SpG + R1333P + A61R + N1317R + L1111R + A1322R |
| G1104K + N1317R + L1111R + A1322R | SpG + R1333P + L1111R + A1322R | SpG + R1333P + G1104K + N1317R + L1111R + A1322R |
| G1104K + N1317R + L1111R + A1322R | SpG + R1333C + L1111R + A1322R | SpG + R1333C + G1104K + N1317R + L1111R + A1322R |
| A61R + G1104K + N1317R + L1111R + A1322R | SpG + R1333C + L1111R + A1322R | SpG + R1333C + A61R + G1104K + N1317R + L1111R + A1322R |
| A61R + G1104K + L1111R + A1322R | SpG + R1333P + L1111R + A1322R | SpG + R1333P + A61R + G1104K + L1111R + A1322R |
| A61R + G1104K + N1317R + L1111R + A1322R | SpG + R1333P + L1111R + A1322R | SpG + R1333P + A61R + G1104K + N1317R + L1111R + A1322R |
| A61R + N1317R + L1111R + A1322R | SpG + R1333C + L1111R + A1322R | SpG + R1333C + A61R + N1317R + L1111R + A1322R |
| A61R + G1104K + L1111R + A1322R | SpG + R1333C + L1111R + A1322R | SpG + R1333C + A61R + G1104K + L1111R + A1322R |
| G1104K + N1317R + L1111R + A1322R | SpG + R1333A + L1111R + A1322R | SpG + R1333A + G1104K + N1317R + L1111R + A1322R |

TABLE 5-continued

PREFERRED VARIANTS

| combinations of up-activity | parental variant | name |
|---|---|---|
| A61R + G1104K + N1317R + L1111R + A1322R | SpG + R1333A + L1111R + A1322R | SpG + R1333A + A61R + G1104K + N1317R + L1111R + A1322R |
| A61R + N1317R + L1111R + A1322R | SpG + R1333A + L1111R + A1322R | SpG + R1333A + A61R + N1317R + L1111R + A1322R |
| A61R + G1104K + L1111R + A1322R | SpG + R1333A + L1111R + A1322R | SpG + R1333A + A61R + G1104K + L1111R + A1322R |
| G1104K + L1111R + A1322R | SpG + R1333P + L1111R + A1322R | SpG + R1333P + G1104K + L1111R + A1322R |
| N1317R + L1111R + A1322R | SpG + R1333P + L1111R + A1322R | SpG + R1333P + N1317R + L1111R + A1322R |
| A61R + L1111R + A1322R | SpG + R1333P + L1111R + A1322R | SpG + R1333P + A61R + L1111R + A1322R |
| N1317R + L1111R + A1322R | SpG + R1333C + L1111R + A1322R | SpG + R1333C + N1317R + L1111R + A1322R |
| G1104K + L1111R + A1322R | SpG + R1333C + L1111R + A1322R | SpG + R1333C + G1104K + L1111R + A1322R |
| A61R + L1111R + A1322R | SpG + R1333C + L1111R + A1322R | SpG + R1333C + A61R + L1111R + A1322R |
| G1104K + L1111R + A1322R | SpG + R1333A + L1111R + A1322R | SpG + R1333A + G1104K + L1111R + A1322R |
| N1317R + L1111R + A1322R | SpG + R1333A + L1111R + A1322R | SpG + R1333A + N1317R + L1111R + A1322R |
| A61R + L1111R + A1322R | SpG + R1333A + L1111R + A1322R | SpG + R1333A + A61R + L1111R + A1322R |

These variants are, in order, D1135L/S1136W/G1218K/E1219Q/R1333P/R1335Q/T1337R/A61R+N1317R+L1111R+A1322R; D1135L/S1136W/G1218K/E1219Q/R1333P/R1335Q/T1337R/G1104K+N1317R+L1111R+A1322R; D1135L/S1136W/G1218K/E1219Q/R1333P/R1335Q/T1337R/G1104K+N1317R+L1111R+A1322R; D1135L/S1136W/G1218K/E1219Q/R1333P/R1335Q/T1337R/A61R+G1104K+N1317R+L1111R+A1322R; D1135L/S1136W/G1218K/E1219Q/R1333P/R1335Q/T1337R/A61R+G1104K+L1111R+A1322R; D1135L/S1136W/G1218K/E1219Q/R1333P/R1335Q/T1337R/A61R+G1104K+N1317R+L1111R+A1322R; D1135L/S1136W/G1218K/E1219Q/R1333P/R1335Q/T1337R/A61R+N1317R+L1111R+A1322R; D1135L/S1136W/G1218K/E1219Q/R1333P/R1335Q/T1337R/A61R+G1104K+L1111R+A1322R; D1135L/S1136W/G1218K/E1219Q/R1333P/R1335Q/T1337R/G1104K+N1317R+L1111R+A1322R; D1135L/S1136W/G1218K/E1219Q/R1333P/R1335Q/T1337R/A61R+G1104K+N1317R+L1111R+A1322R; D1135L/S1136W/G1218K/E1219Q/R1333P/R1335Q/T1337R/A61R+N1317R+L1111R+A1322R; D1135L/S1136W/G1218K/E1219Q/R1333P/R1335Q/T1337R/A61R+G1104K+L1111R+A1322R; D1135L/S1136W/G1218K/E1219Q/R1333P/R1335Q/T1337R/G1104K+L1111R+A1322R; D1135L/S1136W/G1218K/E1219Q/R1333P/R1335Q/T1337R/N1317R+L1111R+A1322R; D1135L/S1136W/G1218K/E1219Q/R1333P/R1335Q/T1337R/A61R+L1111R+A1322R; D1135L/S1136W/G1218K/E1219Q/R1333P/R1335Q/T1337R/N1317R+L1111R+A1322R; D1135L/51136W/G1218K/E1219Q/R1333P/R1335Q/T1337R/G1104K+L1111R+A1322R; D1135L/S1136W/G1218K/E1219Q/R1333P/R1335Q/T1337R/A61R+L1111R+A1322R; D1135L/S1136W/G1218K/E1219Q/R1333P/R1335Q/T1337R/G1104K+L1111R+A1322R; D1135L/S1136W/G1218K/E1219Q/R1333P/R1335Q/T1337R/N1317R+L1111R+A1322R; and D1135L/S1136W/G1218K/E1219Q/R1333P/R1335Q/T1337R/A61R+L1111R+A1322R.

In some embodiments, the SpCas9 variants also include mutations at one of the following amino acid positions, which reduce or destroy the nuclease activity of the Cas9: D10, E762, D839, H983, or D986 and H840 or N863, e.g., D10A/DION and H840A/H840N/H840Y, to render the nuclease portion of the protein catalytically inactive; substitutions at these positions could be alanine (as they are in Nishimasu al., Cell 156, 935-949 (2014)), or other residues, e.g., glutamine, asparagine, tyrosine, serine, or aspartate, e.g., E762Q, H983N, H983Y, D986N, N863D, N863S, or N863H (see WO 2014/152432). In some embodiments, the variant includes mutations at D10A or H840A (which creates a single-strand nickase), or mutations at D10A and H840A (which abrogates nuclease activity; this mutant is known as dead Cas9 or dCas9).

In some embodiments, the SpCas9 variants also include mutations at one or more amino acid positions that increase the specificity of the protein (i.e., reduce off-target effects). In some embodiments, the SpCas9 variants include one, two, three, four, five, six, seven, eight, nine, ten, or all eleven of the following mutations: N497A, R661A, N692A, M694A, Q695A, H698A, K810A, K848A, Q926A, K1003A, and/or R1060A.

In some embodiments, the SpCas9 variants include mutations at one, two, three, four, five, six or all seven of the following positions: L169A, Y450, N497, R661, Q695, Q926, and/or D1135E, e.g., in some embodiments, the variant SpCas9 proteins comprise mutations at one, two, three, or all four of the following: N497, R661, Q695, and Q926, e.g., one, two, three, or all four of the following mutations: N497A, R661A, Q695A, and Q926A. In some embodiments, the variant SpCas9 proteins comprise mutations at Q695 and/or Q926, and optionally one, two, three, four or all five of L169, Y450, N497, R661 and D1135E, e.g., including but not limited to Y450A/Q695A, L169A/Q695A, Q695A/Q926A, Q695A/D1135E, Q926A/D1135E, Y450A/D1135E, L169A/Y450A/Q695A, L169A/Q695A/Q926A, Y450A/Q695A/Q926A, R661A/Q695A/Q926A, N497A/Q695A/Q926A, Y450A/Q695A/D1135E, Y450A/

Q926A/D1135E, Q695A/Q926A/D1135E, L169A/Y450A/ Q695A/Q926A, L169A/R661A/Q695A/Q926A, Y450A/ R661A/Q695A/Q926A, N497A/Q695A/Q926A/D1135E, R661A/Q695A/Q926A/D1135E, and Y450A/Q695A/ Q926A/D1135E. See, e.g., Kleinstiver et al., Nature 529: 490-495 (2016); WO 2017/040348; U.S. Pat. No. 9,512,446).

In some embodiments, the SpCas9 variants also include mutations at one, two, three, four, five, six, seven, or more of the following positions: F491, M495, T496, N497, G582, V583, E584, D585, N588, T657, G658, W659, R661, N692, M694, Q695, H698, K918, V922, and/or R925, and optionally at Q926, preferably comprising a sequence that is at least 80% identical to the amino acid sequence of SEQ ID NO:1 with mutations at one, two, three, four, five, six, seven, or more of the following positions: F491, M495, T496, N497, G582, V583, E584, D585, N588, T657, G658, W659, R661, N692, M694, Q695, H698, K918, V922, and/or R925, and optionally at Q926.

In some embodiments, the SpCas9 variants include one or more of a nuclear localization sequence, cell penetrating peptide sequence, and/or affinity tag.

In some embodiments, the proteins comprise mutations at one, two, three, or all four of the following: N692, M694, Q695, and H698; G582, V583, E584, D585, and N588; T657, G658, W659, and R661; F491, M495, T496, and N497; or K918, V922, R925, and Q926.

In some embodiments, the proteins comprise one, two, three, four, or all of the following mutations: N692A, M694A, Q695A, and H698A; G582A, V583A, E584A, D585A, and N588A; T657A, G658A, W659A, and R661A; F491A, M495A, T496A, and N497A; or K918A, V922A, R925A, and Q926A.

In some embodiments, the proteins comprise mutations: N692A/M694A/Q695A/H698A.

In some embodiments, the proteins comprise mutations: N692A/M694A/Q695A/H698A/Q926A; N692A/M694A/ Q695A/Q926A; N692A/M694A/H698A/Q926A; N692A/ Q695A/H698A/Q926A; M694A/Q695A/H698A/Q926A; N692A/Q695A/H698A; N692A/M694A/Q695A; N692A/ H698A/Q926A; N692A/M694A/Q926A; N692A/M694A/ H698A; M694A/Q695A/H698A; M694A/Q695A/Q926A; Q695A/H698A/Q926A; G582A/V583A/E584A/D585A/ N588A/Q926A; G582A/V583A/E584A/D585A/N588A; T657A/G658A/W659A/R661A/Q926A; T657A/G658A/ W659A/R661A; F491A/M495A/T496A/N497A/Q926A; F491A/M495A/T496A/N497A; K918A/V922A/R925A/ Q926A; or 918A/V922A/R925A. See, e.g., Chen et al., "Enhanced proofreading governs CRISPR-Cas9 targeting accuracy," bioRxiv, doi.org/10.1101/160036 (Aug. 12, 2017) and Nature, 550 (7676): 407-410 (Oct. 19, 2017).

In some embodiments, the variant proteins include mutations at one or more of R780, K810, R832, K848, K855, K968, R976, H982, K1003, K1014, K1047, and/or R1060, e.g., R780A, K810A, R832A, K848A, K855A, K968A, R976A, H982A, K1003A, K1014A, K1047A, and/or R1060A, e.g., K855A; K810A/K1003A/R1060A; (also referred to as eSpCas9 1.0); or K848A/K1003A/R1060A (also referred to as eSpCas9 1.1) (see Slaymaker et al., Science. 2016 Jan. 1; 351 (6268): 84-8).

In some embodiments, the variant proteins include mutations at R691, e.g. R691A. See, e.g. Vakulskas et al., Nat Med. 2018 August; 24 (8): 1216-1224.

In some embodiments, the variant proteins include mutations at one or more of M495, Y515, K526, and R661, e.g., M495V, Y515N, K526E, R661Q, R661L, and/or R661S, e.g. M495V/Y515N/K526E/R661Q; M495V/Y515N/ K526E/R661L; or M495V/Y515N/K526E/R661S. See, e.g. Casini et al., Nat Biotechnol. 2018 March; 36(3): 265-271.

Also provided herein are isolated nucleic acids encoding the SpCas9 variants, vectors comprising the isolated nucleic acids, optionally operably linked to one or more regulatory domains for expressing the variant proteins, and host cells, e.g., mammalian host cells, comprising the nucleic acids, and optionally expressing the variant proteins.

The variant proteins described herein can be used in place of SpCas9 proteins in fusion proteins, including those described in the foregoing references with guide RNAs that target sequences that have PAM sequences according to Tables 1, 2, or 3.

In addition, the variants described herein can be used in fusion proteins in place of the wild-type Cas9 or other Cas9 mutations (such as the dCas9 or Cas9 nickase described above) as known in the art, e.g., a fusion protein with a heterologous functional domain, e.g., as described in WO 2014/124284. In some embodiments, the heterologous functional domain has a DNA-modifying activity. For example, the variants, preferably comprising one or more nuclease-reducing or killing mutation, can be fused on the N or C terminus of the Cas9 to a transcriptional activation domain or other heterologous functional domains (e.g., transcriptional repressors (e.g., KRAB, ERD, SID, and others, e.g., amino acids 473-530 of the ets2 repressor factor (ERF) repressor domain (ERD), amino acids 1-97 of the KRAB domain of KOX1, or amino acids 1-36 of the Mad mSIN3 interaction domain (SID); see Beerli et al., PNAS USA 95:14628-14633 (1998)) or silencers such as Heterochromatin Protein 1 (HP1, also known as swi6), e.g., HP1α or HP1β; proteins or peptides that could recruit long non-coding RNAs (lncRNAs) fused to a fixed RNA binding sequence such as those bound by the MS2 coat protein, endoribonuclease Csy4, or the lambda N protein; enzymes that modify the methylation state of DNA (e.g., DNA methyltransferase (DNMT) or TET proteins); enzymes that modify histone subunits (e.g., histone acetyltransferases (HAT), histone deacetylases (HDAC), histone methyltransferases (e.g., for methylation of lysine or arginine residues) or histone demethylases (e.g., for demethylation of lysine or arginine residues)) (see, e.g., Komor et al., Nature. 2016 May 19; 533(7603): 420-4; Nishida et al., Science. 2016 Sep. 16; 353(6305). pii: aaf8729; Rees et al., Nat Commun. 2017 Jun. 6; 8:15790; or Kim et al., Nat Biotechnol. 2017 April; 35 (4):371-376) as are known in the art can also be used. A number of sequences for such domains are known in the art, e.g., a domain that catalyzes hydroxylation of methylated cytosines in DNA. Exemplary proteins include the Ten-Eleven-Translocation (TET) 1-3 family, enzymes that converts 5-methylcytosine (5-mC) to 5-hydroxymethylcytosine (5-hmC) in DNA.

Sequences for human TET1-3 are known in the art and are shown in the following table:

| Gene | GenBank Accession Nos. | |
|---|---|---|
| | Amino Acid | Nucleic Acid |
| TET1 | NP_085128.2 | NM_030625.2 |
| TET2* | NP_001120680.1 (var 1) | NM_001127208.2 |
| | NP_060098.3 (var 2) | NM_017628.4 |
| TET3 | NP_659430.1 | NM_144993.1 |

*Variant (1) represents the longer transcript and encodes the longer isoform (a). Variant (2) differs in the 5' UTR and in the 3' UTR and coding sequence compared to variant 1. The resulting isoform (b) is shorter and has a distinct C-terminus compared to isoform a.

In some embodiments, all or part of the full-length sequence of the catalytic domain can be included, e.g., a catalytic module comprising the cysteine-rich extension and the 2OGFeDO domain encoded by 7 highly conserved exons, e.g., the Tet1 catalytic domain comprising amino acids 1580-2052, Tet2 comprising amino acids 1290-1905 and Tet3 comprising amino acids 966-1678. See, e.g., FIG. 1 of Iyer et al., Cell Cycle. 2009 Jun. 1; 8 (11): 1698-710. Epub 2009 Jun. 27, for an alignment illustrating the key catalytic residues in all three Tet proteins, and the supplementary materials thereof for full length sequences (see, e.g., seq 2c); in some embodiments, the sequence includes amino acids 1418-2136 of Tet1 or the corresponding region in Tet2/3.

Other catalytic modules can be from the proteins identified in Iyer et al., 2009.

In some embodiments, the heterologous functional domain is a biological tether, and comprises all or part of (e.g., DNA binding domain from) the MS2 coat protein, endoribonuclease Csy4, or the lambda N protein. These proteins can be used to recruit RNA molecules containing a specific stem-loop structure to a locale specified by the dCas9 gRNA targeting sequences. For example, a dCas9 variant fused to MS2 coat protein, endoribonuclease Csy4, or lambda N can be used to recruit a long non-coding RNA (lncRNA) such as XIST or HOTAIR; see, e.g., Keryer-Bibens et al., Biol. Cell 100:125-138 (2008), that is linked to the Csy4, MS2 or lambda N binding sequence. Alternatively, the Csy4, MS2 or lambda N protein binding sequence can be linked to another protein, e.g., as described in Keryer-Bibens et al., supra, and the protein can be targeted to the dCas9 variant binding site using the methods and compositions described herein. In some embodiments, the Csy4 is catalytically inactive. In some embodiments, the Cas9 variant, preferably a dCas9 variant, is fused to FokI as described in WO 2014/204578.

In some embodiments, the heterologous functional domain comprises a base editor, e.g., a cytidine deaminase domain, e.g., from the apolipoprotein B mRNA-editing enzyme, catalytic polypeptide-like (APOBEC) family of deaminases, including APOBEC1, APOBEC2, APOBEC3A, APOBEC3B, APOBEC3C, APOBEC3D/E, APOBEC3F, APOBEC3G, APOBEC3H, or APOBEC4; activation-induced cytidine deaminase (AID), e.g., activation induced cytidine deaminase (AICDA); cytosine deaminase 1 (CDA1) or CDA2; or cytosine deaminase acting on tRNA (CDAT). In some embodiments, the heterologous functional domain is a deaminase that modifies adenosine DNA bases, e.g., the deaminase domain is from an adenosine deaminase 1 (ADA1), ADA2; adenosine deaminase acting on RNA 1 (ADAR1), ADAR2, ADAR3; adenosine deaminase acting on tRNA 1 (ADAT1), ADAT2, ADAT3; and naturally occurring or engineered tRNA-specific adenosine deaminase (TadA). Such proteins comprising a base editing domain include cytosine or adenine base editors (CBEs or ABEs), or variants thereof, e.g., variants with reduced RNA editing activity, e.g., the SElective Curbing of Unwanted RNA Editing (SECURE)-BE3 variants and SECURE-ABE variants. See, e.g., Gaudelli et al., Nature 551, 464-471 (2017). Grünewald et al., Nature. 2019 May; 569 (7756): 433-437; Grünewald et al., bioRxiv 631721; doi.org/10.1101/631721; Grünewald et al., Nat Biotechnol. 2019 September; 37(9): 1041-1048; Abudayyeh et al., Science. 2019 Jul. 26; 365(6451): 382-386; and Gehrke et al., Nat Biotechnol. 2018 November; 36(10):977-982.

In some embodiments, the base editing domain is an adenosine deaminase domain, e.g., a wild type and/or engineered adenosine deaminase TadA monomer or dimer (e.g., homodimeric or heterodimeric TadA domains from ABEmax, ABE7.10, or ABE8e; other options include monomer or dimer TadAs from ABEs 0.1, 0.2, 1.1, 1.2, 2.1, 2.2, 2.3, 2.4, 2.5, 2.6, 2.7, 2.8, 2.9, 2.10, 2.11, 2.12, 3.1, 3.2, 3.3, 3.4, 3.5, 3.6, 3.7, 3.8, 4.1, 4.2, 4.3, 5.1, 5.2, 5.3, 5.4, 5.5, 5.6, 5.7, 5.8, 5.9, 5.10, 5.11, 5.12, 5.13, 5.14, 6.1, 6.2, 6.3, 6.4, 6.5, 6.6, 7.1, 7.2, 7.3, 7.4, 7.5, 7.6, 7.7, 7.8, 7.9, 7.10, or ABEmax, or ABE8.8, ABE8.13, ABE8.17, ABE8.20, ABE8e—as well as K20A/R21A, V82G, or V106W variants thereof), E. coli TadA monomer, or homo- or heterodimers thereof fused to the N or C terminus, bearing one or more mutations in either or both monomers (e.g., the TadA mutant used in miniABEmax-V82G, miniABEmax-K20A/R21A, miniABEmax-V106W or any other variant thereof, that decrease RNA editing activity while preserving DNA editing activity; see, e.g., Grünewald et al., Nature Biotechnology volume 38, pages 861-864 (2020) and references cited therein.

In some embodiments, the heterologous functional domain is an enzyme, domain, or peptide that inhibits or enhances endogenous DNA repair or base excision repair (BER) pathways, e.g., uracil DNA glycosylase inhibitor (UGI) that inhibits uracil DNA glycosylase (UDG, also known as uracil N-glycosylase, or UNG) mediated excision of uracil to initiate BER; or DNA end-binding proteins such as Gam from the bacteriophage Mu.

In some embodiments, the heterologous functional domain is a prime editor, e.g., a reverse-transcriptase (RT) domain (e.g., Moloney murine leukaemia virus (M-MLV) RT or other RT enzyme), e.g., fused to a Cas9 nickase. In such embodiments, the variant is used in conjunction with a prime editing guide RNA (pegRNA) that both specifies the target site and encodes the desired edit. See, e.g., Anzalone et al., Nature December 2019; 576 (7785): 149-157.

In some embodiments, the fusion proteins include a linker between the dCas9 variant and the heterologous functional domains. Linkers that can be used in these fusion proteins (or between fusion proteins in a concatenated structure) can include any sequence that does not interfere with the function of the fusion proteins. In preferred embodiments, the linkers are short, e.g., 2-20 amino acids, and are typically flexible (i.e., comprising amino acids with a high degree of freedom such as glycine, alanine, and serine). In some embodiments, the linker comprises one or more units consisting of GGGS (SEQ ID NO:2) or GGGGS (SEQ ID NO:3), e.g., two, three, four, or more repeats of the GGGS (SEQ ID NO:2) or GGGGS (SEQ ID NO:3) unit. Other linker sequences can also be used.

Methods of Use

The variants described herein have a number of uses; for example, they can be used for altering the genome of a cell; the methods generally include expressing the variant proteins in the cells, along with a guide RNA having a region complementary to a selected portion of the genome of the cell. Alternatively or in addition, they can be used to alter dsDNA in vitro, e.g., acting on DNA in a tube; for example, the SpRY variant described herein can be used is as a 'PAMless' restriction enzyme, to DNA anywhere, e.g., in a cell or in vitro reaction/test tube.

Methods for using CRISPR to selectively alter dsDNA, including altering the genome of a cell, are known in the art, see, e.g., U.S. Pat. No. 8,697,359; US2010/0076057; US2011/0189776; US2011/0223638; US2013/0130248; WO/2008/108989; WO/2010/054108; WO/2012/164565; WO/2013/098244; WO/2013/176772; US20150050699; US20150045546; US20150031134; US20150024500;

US20140377868; US20140357530; US20140349400; US20140335620; US20140335063; US20140315985; US20140310830; US20140310828; US20140309487; US20140304853; US20140298547; US20140295556; US20140294773; US20140287938; US20140273234; US20140273232; US20140273231; US20140273230; US20140271987; US20140256046; US20140248702; US20140242702; US20140242700; US20140242699; US20140242664; US20140234972; US20140227787; US20140212869; US20140201857; US20140199767; US20140189896; US20140186958; US20140186919; US20140186843; US20140179770; US20140179006; US20140170753; Makarova et al., "Evolution and classification of the CRISPR-Cas systems" 9(6) Nature Reviews Microbiology 467-477 (1-23) (June 2011); Wiedenheft et al., "RNA-guided genetic silencing systems in bacteria and archaea" 482 Nature 331-338 (Feb. 16, 2012); Gasiunas et al., "Cas9-crRNA ribonucleoprotein complex mediates specific DNA cleavage for adaptive immunity in bacteria" 109(39) Proceedings of the National Academy of Sciences USA E2579-E2586 (Sep. 4, 2012); Jinek et al., "A Programmable Dual-RNA-Guided DNA Endonuclease in Adaptive Bacterial Immunity" 337 Science 816-821 (Aug. 17, 2012); Carroll, "A CRISPR Approach to Gene Targeting" 20(9) Molecular Therapy 1658-1660 (September 2012); U.S. Appl. No. 61/652,086, filed May 25, 2012; Al-Attar et al., Clustered Regularly Interspaced Short Palindromic Repeats (CRISPRs): The Hallmark of an Ingenious Antiviral Defense Mechanism in Prokaryotes, Biol Chem. (2011) vol. 392, Issue 4, pp. 277-289; Hale et al., Essential Features and Rational Design of CRISPR RNAs That Function With the Cas RAMP Module Complex to Cleave RNAs, Molecular Cell, (2012) vol. 45, Issue 3, 292-302.

Delivery and Expression Systems

To use the Cas9 variants described herein, it may be desirable to express them from a nucleic acid that encodes them. This can be performed in a variety of ways. For example, the nucleic acid encoding the Cas9 variant can be cloned into an intermediate vector for transformation into prokaryotic or eukaryotic cells for replication and/or expression. Intermediate vectors are typically prokaryote vectors, e.g., plasmids, or shuttle vectors, or insect vectors, for storage or manipulation of the nucleic acid encoding the Cas9 variant for production of the Cas9 variant. The nucleic acid encoding the Cas9 variant can also be cloned into an expression vector, for administration to a plant cell, animal cell, preferably a mammalian cell or a human cell, fungal cell, bacterial cell, or protozoan cell.

To obtain expression, a sequence encoding a Cas9 variant is typically subcloned into an expression vector that contains a promoter to direct transcription. Suitable bacterial and eukaryotic promoters are well known in the art and described, e.g., in Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 2010). Bacterial expression systems for expressing the engineered protein are available in, e.g., E. coli, Bacillus sp., and Salmonella (Palva et al., 1983, Gene 22:229-235). Kits for such expression systems are commercially available. Eukaryotic expression systems for mammalian cells, yeast, and insect cells are well known in the art and are also commercially available.

The promoter used to direct expression of a nucleic acid depends on the particular application. For example, a strong constitutive promoter is typically used for expression and purification of fusion proteins. In contrast, when the Cas9 variant is to be administered in vivo for gene regulation, either a constitutive or an inducible promoter can be used, depending on the particular use of the Cas9 variant. In addition, a preferred promoter for administration of the Cas9 variant can be a weak promoter, such as HSV TK or a promoter having similar activity. The promoter can also include elements that are responsive to transactivation, e.g., hypoxia response elements, Gal4 response elements, lac repressor response element, and small molecule control systems such as tetracycline-regulated systems and the RU-486 system (see, e.g., Gossen & Bujard, 1992, Proc. Natl. Acad. Sci. USA, 89:5547; Oligino et al., 1998, Gene Ther., 5:491-496; Wang et al., 1997, Gene Ther., 4:432-441; Neering et al., 1996, Blood, 88:1147-55; and Rendahl et al., 1998, Nat. Biotechnol., 16:757-761).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the Cas9 variant, and any signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use of the Cas9 variant, e.g., expression in plants, animals, bacteria, fungus, protozoa, etc. Standard bacterial expression vectors include plasmids such as pBR322 based plasmids, pSKF, pET23D, and commercially available tag-fusion expression systems such as GST and LacZ.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

The vectors for expressing the Cas9 variants can include RNA Pol III promoters to drive expression of the guide RNAs, e.g., the H1, U6 or 7SK promoters. These human promoters allow for expression of Cas9 variants in mammalian cells following plasmid transfection.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with the gRNA encoding sequence under the direction of the polyhedrin promoter or other strong baculovirus promoters.

The elements that are typically included in expression vectors also include a replicon that functions in E. coli, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., 1989, J. Biol.

Chem., 264:17619-22; Guide to Protein Purification, in Methods in Enzymology, vol. 182 (Deutscher, ed., 1990)). Transformation of eukaryotic and prokaryotic cells are performed according to standard techniques (see, e.g., Morrison, 1977, J. Bacteriol. 132:349-351; Clark-Curtiss & Curtiss, Methods in Enzymology 101:347-362 (Wu et al., eds, 1983).

Any of the known procedures for introducing foreign nucleotide sequences into host cells may be used. These include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the Cas9 variant.

Alternatively, the methods can include delivering the Cas9 variant protein and guide RNA together, e.g., as a complex. For example, the Cas9 variant and gRNA can be can be overexpressed in a host cell and purified, then complexed with the guide RNA (e.g., in a test tube) to form a ribonucleoprotein (RNP), and delivered to cells. In some embodiments, the variant Cas9 can be expressed in and purified from bacteria through the use of bacterial Cas9 expression plasmids. For example, His-tagged variant Cas9 proteins can be expressed in bacterial cells and then purified using nickel affinity chromatography. The use of RNPs circumvents the necessity of delivering plasmid DNAs encoding the nuclease or the guide, or encoding the nuclease as an mRNA. RNP delivery may also improve specificity, presumably because the half-life of the RNP is shorter and there's no persistent expression of the nuclease and guide (as you'd get from a plasmid). The RNPs can be delivered to the cells in vivo or in vitro, e.g., using lipid-mediated transfection or electroporation. See, e.g., Liang et al. "Rapid and highly efficient mammalian cell engineering via Cas9 protein transfection." Journal of biotechnology 208 (2015): 44-53; Zuris, John A., et al. "Cationic lipid-mediated delivery of proteins enables efficient protein-based genome editing in vitro and in vivo." Nature biotechnology 33.1 (2015): 73-80; Kim et al. "Highly efficient RNA-guided genome editing in human cells via delivery of purified Cas9 ribonucleoproteins." Genome research 24.6 (2014): 1012-1019.

The present invention includes the vectors and cells comprising the vectors.

EXAMPLES

The invention is further described in the following examples, which do not limit the scope of the invention described in the claims.

Methods

The following materials and methods were used in the Examples below.

Plasmids and Oligonucleotides

New plasmids have been deposited with Addgene. Target site sequences for sgRNAs and oligonucleotide sequences are available in Tables 6 and 7, respectively. The SpCas9 nuclease human expression plasmid was generated by subcloning the SpCas9 open reading frame from pX330 (Addgene plasmid 42230; a gift from Feng Zhang) into the NotI and AgeI sites of JDS246 (Addgene plasmid 43861). Nuclease constructs harboring a C-terminal BP (SV40) NLS-3xFLAG-P2A-EGFP sequence were utilized for all human cell experiments unless otherwise indicated. Cytidine base editor (CBE) constructs were generated by subcloning the open reading frame of BE4max (Addgene plasmid 112099; a gift from David Liu) into the NotI and AgeI sites of pCAG-CFP (Addgene plasmid 11179; a gift from Connie Cepko). Adenine base editor (ABE) variants were generated by modifying ABEmax (Addgene plasmid 112101; a gift from David Liu). All modifications to plasmids, including generation of point mutations, altered nuclear localization architectures, and the addition of P2A-EGFP were generated through standard molecular cloning and isothermal assembly. Human cell expression plasmids for U6 promoter-driven SpCas9 sgRNAs were generated by annealing and ligating duplexed oligonucleotides corresponding to spacer sequences into BsmBI-digested BPK1520[8]. Plasmids for in vitro transcription of SpCas9 sgRNAs were generated by annealing and ligating oligonucleotides corresponding to spacer sequence duplexes into BsaI-digested MSP3485 for T7 promoter-driven transcription of sgRNAs.

Plasmid libraries with 8 nt randomized PAM sequences on the 3' end of the target sites were generated from two oligonucleotides encoding separate spacer sequences, similar to as previously described[36]. Briefly, Klenow(-exo) (NEB) was used to generate the bottom strand of the dsDNA sequence, and the product was digested with EcoRI prior to ligation into EcoRI and SphI digested p11-lacY-wtx1 (Addgene plasmid 69056; a gift from Huimin Zhao). Ligated plasmids were transformed into electrocompetent XL1-Blue E. coli, recovered in 9 ml of super optimal broth with catabolite repression (SOC) at 37° C. for approximately 60 minutes, and then grown for 16 hours in 150 mL of Luria-Bertani (LB) medium with 100 μg/mL carbenicillin. The complexity of each library was estimated to be greater than 105 unique PAMs based on the number of transformants. Plasmid libraries were linearized with PvuI (NEB) prior to use in the in vitro cleavage reactions.

Structural Modeling of SpCas9

The crystal structures of WT SpCas9 (PDB: 4UN3)[20], SpCas9-VQR (PDB: 5B2R)[25], and SpCas9-VRER (PDB: 5B2T)[25] were visualized using PyMOL version 2.3.3.

Human Cell Culture

Human HEK 293T cells (ATCC) were cultured in Dulbecco's Modified Eagle Medium (DMEM) supplemented with 10% heat-inactivated FBS (HI-FBS) and 1% penicillin/streptomycin. The supernatant media from cell cultures was analyzed monthly for the presence of *mycoplasma* using MycoAlert PLUS (Lonza).

Transfection of Human Cells

All experiments were performed with at least 3 independent biological replicates. For all human cell experiments, transfections were performed between 20 and 24 hours following seeding of $2 \times 10^4$ HEK 293T cells per well in 96-well plates. For nuclease experiments, 29 ng of nuclease and 12.5 ng of sgRNA expression plasmids (unless otherwise indicated) were mixed with 0.3 μL of TransIT-X2 (Mirus) in a total volume of 15 μL Opti-MEM (Thermo Fisher Scientific), incubated for 15 minutes at room temperature, and added to HEK 293T cells. For CBE and ABE experiments, 70 ng of base-editor and 30 ng of sgRNA expression plasmids were mixed with 0.72 μL of TransIT-X2 in a total volume of 15 μL Opti-MEM, incubated for 15 minutes at room temperature, and added to HEK 293T cells. Nuclease and CBE experiments were halted after 72 hours, and ABE experiments after 120 hours. Genomic DNA was collected by discarding the media, resuspending the cells in 100 μL of quick lysis buffer (20 mM Hepes pH 7.5, 100 mM KCl, 5 mM MgCl$_2$, 5% glycerol, 25 mM DTT, 0.1% Triton X-100, and 60 ng/ul Proteinase K (New England Biolabs; NEB)), heating the lysate for 6 minutes at 65° C., heating at 98° C. for 2 minutes, and then storing at −20° C.

Assessment of Nuclease and Base Editor Activities in Human Cells

The efficiency of genome modification by CRISPR nucleases, CBEs, and ABEs were determined by next-generation sequencing using a 2-step PCR-based Illumina library construction method. Briefly, genomic loci were amplified from approximately 100 ng of genomic DNA using Q5 High-fidelity DNA Polymerase (NEB). PCR products were purified using paramagnetic beads prepared as previously described[36,37]. Approximately 20 ng of purified PCR product was used as template for a second PCR to add Illumina barcodes and adapter sequences using Q5. PCR products were purified prior to quantification via capillary electrophoresis (Qiagen QIAxcel), normalization, and pooling. Final libraries were quantified by qPCR (Illumina Library qPCR Quantification Kit, KAPA Biosystems) and sequenced on a MiSeq sequencer using a 300-cycle v2 kit (Illumina). Genome editing activities were determined from the sequencing data using CRISPResso2[38] with commands for nucleases: --min_reads_to_use_region 100; for CBEs: --min_reads_to_use_region 100-w 20--cleavage_off-set-10--base_editor_output; and for ABEs: min_reads_to_use_region 100-w 20--cleavage_offset-10--base_editor_output--conversion_nuc_from A--conversion_nuc_to G. The edit window for base editor constructs was defined as PAM-distal spacer positions 3-9 for CBEs and positions 5-7 for ABEs.

In Vitro Transcription of sgRNAs

SpCas9 sgRNAs were in vitro transcribed at 37° C. for 16 hours from roughly 1 μg of HindIII linearized sgRNA T7-transcription plasmid template (cloned into MSP3485) using the T7 RiboMAX Express Large Scale RNA Production Kit (Promega). The DNA template was degraded by the addition of 1 μL RQ1 DNase at 37° C. for 15 minutes. sgRNAs were purified with the MEGAclear Transcription Clean-Up Kit (ThermoFisher) and refolded by heating to 90° C. for 5 minutes and then cooling to room temperature for 15 minutes.

Expression of SpCas9 and Base Editor Proteins in Human Cells and Normalization of Lysates To generate SpCas9 and variant proteins from human cell lysates, approximately 20-24 hours prior to transfection 1.5×10$^5$ HEK 293T cells were seeded in 24-well plates. Transfections containing 500 ng of human codon optimized nuclease expression plasmid (with a-P2A-EGFP signal) and 1.5 μL TransIT-X2 were mixed in a total volume of 50 μL of Opti-MEM, incubated at room temperature for 15 minutes, and added to the cells. The lysate was harvested after 48 hours by discarding the media and resuspending the cells in 100 ul of gentle lysis buffer (1× SIGMAFAST Protease Inhibitor Cocktail, EDTA-Free (Millipore Sigma), 20 mM Hepes pH 7.5, 100 mM KCl, 5 mM MgCl$_2$, 5% glycerol, 1 mM DTT, and 0.1% Triton X-100). The amount of SpCas9 or base editor protein was approximated from the whole-cell lysate based on EGFP fluorescence. SpCas9 nuclease and base editor lysates were normalized to 150 and 300 nM Fluorescein (Sigma), respectively, based on a Fluorescein standard curve. Fluorescence was measured in 384-well plates on a DTX 880 Multimode Plate Reader (Beckman Coulter) with $\lambda_{ex}$=485 nm and $\lambda_{em}$=535 nm.

High-Throughput PAM Determination Assay for Nucleases

The high-throughput PAM determination assay (HT-PAMDA) was performed using linearized randomized PAM-containing plasmid substrates that were subject to in vitro cleavage reactions with SpCas9 and variant proteins. First, SpCas9 ribonucleoproteins (RNPs) were complexed by mixing 4.375 μL of normalized whole-cell lysate (150 nM Fluorescein) with 8.75 pmol of in vitro transcribed sgRNA and incubating for 5 minutes at 37° C. Cleavage reactions were initiated by the addition of 43.75 fmol of randomized-PAM plasmid library and buffer to bring the total reaction volume to 17.5 L with a final composition of 10 mM Hepes pH 7.5, 150 mM NaCl, and 5 mM MgCl$_2$. Reactions were performed at 37° C. and aliquots were terminated at timepoints of 1, 8, and 32 minutes by removing 5 μL aliquots from the reaction and mixing with 5 μL of stop buffer (50 mM EDTA and 2 mg/ml Proteinase K (NEB)), incubating at room temperature for 10-minutes, and heat inactivating at 98° C. for 5 minutes. For all variants characterized, time courses were completed on both libraries harboring distinct spacer sequences for n=2; several variants were characterized with additional replicates to evaluate reproducibility of the assay (FIG. 8b), where for those variants the final data is an average of all replicates.

Next, approximately 3 ng of digested PAM library for each SpCas9 variant and reaction timepoint was PCR amplified using Q5 polymerase (NEB) and barcoded using unique combinations of i5 and i7 primers. PCR products were pooled for each time point, purified using paramagnetic beads, and prepared for sequencing using one of two library preparation methods. Pooled amplicons were prepared for sequencing using either (1) the KAPA HTP PCR-free Library Preparation Kit (KAPA BioSystems), or (2) a PCR-based method where pooled amplicons were treated with Exonuclease I, purified using paramagnetic beads, amplified using Q5 polymerase and selected primers with approximately 250 pg of pooled amplicons at template, and again purified using paramagnetic beads. Libraries constructed via either method were quantified using the Universal KAPA Illumina Library qPCR Quantification Kit (KAPA Biosystems) and sequenced on a NextSeq sequencer using a either 150-cycle (method 1) or 75-cycle (method 2) NextSeq 500/550 High Output v2.5 kits (Illumina). Identical cleavage reactions prepared and sequenced via either library preparation method did not exhibit substantial differences.

Sequencing reads were analyzed using a custom Python script to determine cleavage rates for all SpCas9 nucleases on each substrate with unique spacers and PAMs, similar to as previously described[36]. Briefly, reads were assigned to specific SpCas9 variants based on based on custom pooling barcodes, assigned timepoints based on the combination of i5 and i7 primer barcodes, assigned to a plasmid library based on the spacer sequence, and assigned to a 3 (NNNN) or 4 (NNNN) nt PAM based on the identities of the DNA bases adjacent to the spacer sequence. Counts for all PAMs were computed for every SpCas9 variant, plasmid library, and timepoint, corrected for inter-sample differences in sequencing depth, converted to a fraction of the initial representation of that PAM in the original plasmid library (as determined by an untreated control), and then normalized to account for the increased fractional representation of uncut substrates over time due to depletion of cleaved substrates (by selecting the five PAMs with the highest average fractional representation across all time points to represent the profile of uncleavable substrates). The depletion of each PAM over time was then fit to an exponential decay model (y (t)=Ae-kt, where y (t) is the normalized PAM count, t is the time (seconds), k is the rate constant, and A is a constant), by nonlinear regression. Reported rates are the average across both spacer sequences and across technical replicates when performed. Nonlinear least squares curve fitting was utilized to model Cas9 nuclease and CBE activities, whereas linear least squares curve fitting was previously used for our Cas12a PAMDA assay[36].

CBE-HT-PAMDA

The cytosine base editor high-throughput PAM determination assay (CBE-HT-PAMDA) was performed using a linearized randomized PAM-containing plasmid library that was subjected to in vitro reactions with base editor variants. First, base editor proteins were complexed with sgRNAs by mixing 8.75 µL of normalized whole-cell lysate (300 nM Fluorescein) with 14 pmol of in vitro transcribed sgRNA and incubating for 5 minutes at 37° C. Cleavage reactions were initiated by the addition of 43.75 fmol of randomized-PAM plasmid library and buffer to bring the total reaction volume to 17.5 µL with a final composition of 10 mM Hepes pH 7.5, 150 mM NaCl, and 5 mM $MgCl_2$. Reactions were performed at 37° C. and aliquots were terminated at timepoints of 4, 32, and 256 minutes by removing 5 µL aliquots from the reaction and mixing with 5 µL of stop buffer (50 mM EDTA and 2 mg/ml Proteinase K (NEB)), incubating at room temperature for 10-minutes, and heat inactivating at 98° C. for 5 minutes. Deamination and nicking events were converted to double strand breaks through the addition of 1 unit of USER enzyme (NEB) in 5 µL of 1×NEB buffer 4 to each reaction, bringing the total volume to 15 µL. After an hour incubation at 37° C., reactions were stopped by adding of 5 ul of 4 mg/mL Proteinase K in 1 mM Tris pH 8.0, incubating at room temperature for 10-minutes, and heat inactivating at 98° C. for 5 minutes. Reactions were carried out on a single plasmid library for each base editor. Samples were subsequently processed as described above for HT-PAMDA for nucleases, with the exception that depletion rates are for a single spacer sequence for CBE-HT-PAMDA, rather than the average of two spacer sequences as in the nuclease analysis.

Additional Methods for Example 15

Human Cell Culture and GUIDE-Seq

Human HEK 293T cells (ATCC) were cultured in Dulbecco's Modified Eagle Medium (DMEM) supplemented with 10% heat-inactivated FBS (HI-FBS) and 1% penicillin/streptomycin. The supernatant media from cell cultures was analyzed monthly for the presence of *mycoplasma* using MycoAlert PLUS (Lonza). All experiments were performed with at least 3 independent biological replicates. For all human cell experiments, transfections were performed between 20 and 24 hours following seeding of 2×10⁴ HEK 293T cells per well in 96-well plates. For GUIDE-seq experiments, 29 ng of nuclease and 12.5 ng of sgRNA expression plasmids, 1 pmol of the GUIDE-seq double-stranded oligodeoxynucleotide (dsODN; oSQT685/686) tag (31), and 0.3 µL of TransIT-X2 (Mirus) were mixed in a total volume of 16 µL Opti-MEM, incubated for 15 minutes at room temperature, and added to HEK 293T cells. Genomic DNA was extracted ~72 hours post-transfection by discarding the media, resuspending the cells in 100 µL of overnight lysis buffer (100 mM Tris pH 7.5, 100 mM NaCl, 5 mM EDTA, 0.05% SDS, 5 µL PK (NEB), and 25 mM DTT), and incubating lysate at 55° C. for 15-18 hours shaking at approximately 200 rpm. Following incubation, genomic DNA was purified using a 0.7× ratio of paramagnetic beads.

GUIDE-seq samples were prepared for sequencing as previously described (Tsai and Zheng et al., *Nature Biotechnology,* 2015) and sequenced on an Illumina NextSeq sequencer in manual mode for custom Index2 read length. Binary base call files were converted to fastq format using bcl2fastq v2.17.1.14. GUIDE-seq data was analyzed using guideseq v1.0.2 (github.com/aryeelab/guideseq) with custom input parameters: demultiplex_min_reads 500,000 for all nucleases; max_mismatches 6 and an NGG PAM for WT SpCas9 samples; max_mismatches 7 and an NGN PAM for SpG samples; and max_mismatches 8 and an NNN PAM for SpRY samples; cell-type specific SNP correction was not performed.

Additional Methods for Example 17

Plasmids pCMV-T7-SpCas9-P2A-EGFP human codon optimized plasmids for wild-type SpCas9 (RTW3027), SpG (RTW4177), and SpRY (RTW4830) were used for expression in human cells (Addgene plasmids 139987, 139988, and 139989 respectively). A pUC19 derivative plasmid (pUC19-U6-EMX1-NGGC-SpCas9_sgRNA; KAC833) was used as a linear double-stranded DNA substrate for in vitro cleavage reactions. This substrate plasmid was first linearized with HindIII (New England Biolabs; NEB).

Human Cell Culture

Human HEK 293T cells (ATCC) were cultured in Dulbecco's Modified Eagle Medium (DMEM) supplemented with 10% heat-inactivated FBS (HI-FBS) and 1% penicillin/streptomycin. The supernatant media from cell cultures was analyzed monthly for the presence of *mycoplasma* using MycoAlert PLUS (Lonza).

In Vitro Transcription of sgRNAs

Target specific oligonucleotides (oligos) encoding a T7 promoter, the target spacer, and a partial sequence of the SpCas9 crRNA were ordered (Integrated DNA Technologies) to the generate DNA templates needed for in vitro transcription (IVT) of SpCas9 single guide RNAs (gRNAs) (Table 8). The target specific oligos were annealed with a common oligo gRNA oligo (oKAC682; AAAAGCACCGACTCGGTGCCACTTTTTCAAGTT-GATAACGGACTAGCCTT ATTTTAACTTGCTAT-TCTAGCTCTAAAAC (SEQ ID NO:40)) that encodes the remainder of the SpCas9 scaffold. The final double-stranded DNA templates for in vitro transcription were generated by annealing a target specific oligo with the common SpCas9 scaffold oligo, and extending the duplex with either Klenow Fragment (3'→5' exo-) (NEB) at 37° C. for 30 minutes. Oligo-derived sgRNA T7-transcription DNA templates were cleaned up using the MinElute PCR Purification Kit (Qiagen). SpCas9 sgRNAs were in vitro transcribed at 37° C. for 16 hours using the T7 RiboMAX Express Large Scale RNA Production Kit (Promega). The DNA template was degraded by the addition of 1 µL RQ1 DNase at 37° C. for 15 minutes. sgRNAs were purified using paramagnetic beads prepared as previously described and refolded by heating to 90° C. for 5 minutes and then cooling to room temperature for 15 minutes.

Expression of SpCas9 Proteins in Human Cells and Normalization of Lysates

To generate SpCas9, SpG, and SpRY proteins from human cell lysates, approximately 20-24 hours prior to transfection 1.5×10⁵ HEK 293T cells were seeded in 24-well plates. Transfections mixtures containing 500 ng of human codon optimized nuclease expression plasmid (with a-P2A-EGFP signal) and 1.5 µL TransIT-X2 were mixed in a total volume of 50 µL of Opti-MEM, incubated at room temperature for 15 minutes, and added to the cells. The lysate was harvested after 48 hours by discarding the media and resuspending the cells in 100 ul of gentle lysis buffer (1×SIGMAFAST Protease Inhibitor Cocktail, EDTA-Free (Millipore Sigma), 20 mM Hepes pH 7.5, 100 mM KCl, 5 mM $MgCl_2$, 5% glycerol, 1 mM DTT, and 0.1% Triton X-100). The amount of SpCas9 protein was approximated from the whole-cell lysate based on EGFP fluorescence. SpCas9 lysates were normalized to 150 nM Fluorescien (Sigma, based on a Fluorescein standard curve. Fluorescence was measured in 384-well plates on a DTX 880 Multimode Plate Reader (Beckman Coulter) with $\lambda_{ex}$=485 nm and $\lambda_{cm}$=535 nm.

In Vitro Cleavage Reactions

SpCas9 ribonucleoproteins (RNPs) were complexed by mixing 9 μL of normalized whole-cell lysate (normalized to 150 nM Fluorescien) with 11.25 pmol of in vitro transcribed sgRNA and incubating for 5 minutes at 37° C. Cleavage reactions were initiated by the addition of 34.82 fmol of HindIII (NEB) linearized plasmid substrate in a total reaction volume of 22.5 μL with a final composition of 10 mM Hepes pH 7.5, 150 mM NaCl, and 5 mM $MgCl_2$. Reactions were performed at 37° C. Aliquots of 5 μL removed at timepoints of 1, 6, 36 and 216 minutes stopped by mixing with 5 μL of stop buffer (50 mM EDTA and 2 mg/ml Proteinase K (NEB)) and incubating at room temperature for 10 minutes. Uncleaved and cleaved fragments from the DNA substrate were purified using paramagnetic beads and quantified via capillary electrophoresis (Qiagen QIAxcel).

Example 1. Structure-Guided Mutagenesis to Relax SpCas9 PAM Preference

Towards eliminating the PAM requirement of SpCas9, we first developed a highly active variant capable of recognizing a reduced NGN PAM compared to the canonical NGG sequence. Our previous work on altering SpCas9 PAM preference motivated our engineering efforts by illuminating several PAM-proximal residues important for PAM recognition[8] (FIG. 1b), observations supported by structural studies[20,24,25] (FIG. 5a-e and see other Examples below). Previous characterizations of SpCas9-VQR (harboring D1135V/R1335Q/T1337R substitutions) and the derivative SpCas9-VRQR variant (that additionally encodes G1218R) demonstrated that these enzymes were able to target an expanded number of non-canonical PAMs including those with variable bases in the $3^{rd}$ position of the PAM (NGAN>NGNG)[8,21]. Based on these observations, we hypothesized that R1335Q-harboring variants with other PI domain substitutions could recognize an expanded number of PAMs (FIGS. 5f-1i). Thus, for our present engineering approach we utilized SpCas9-VRQR as a molecular scaffold to further relax SpCas9 PAM preference.

Figure 6E:
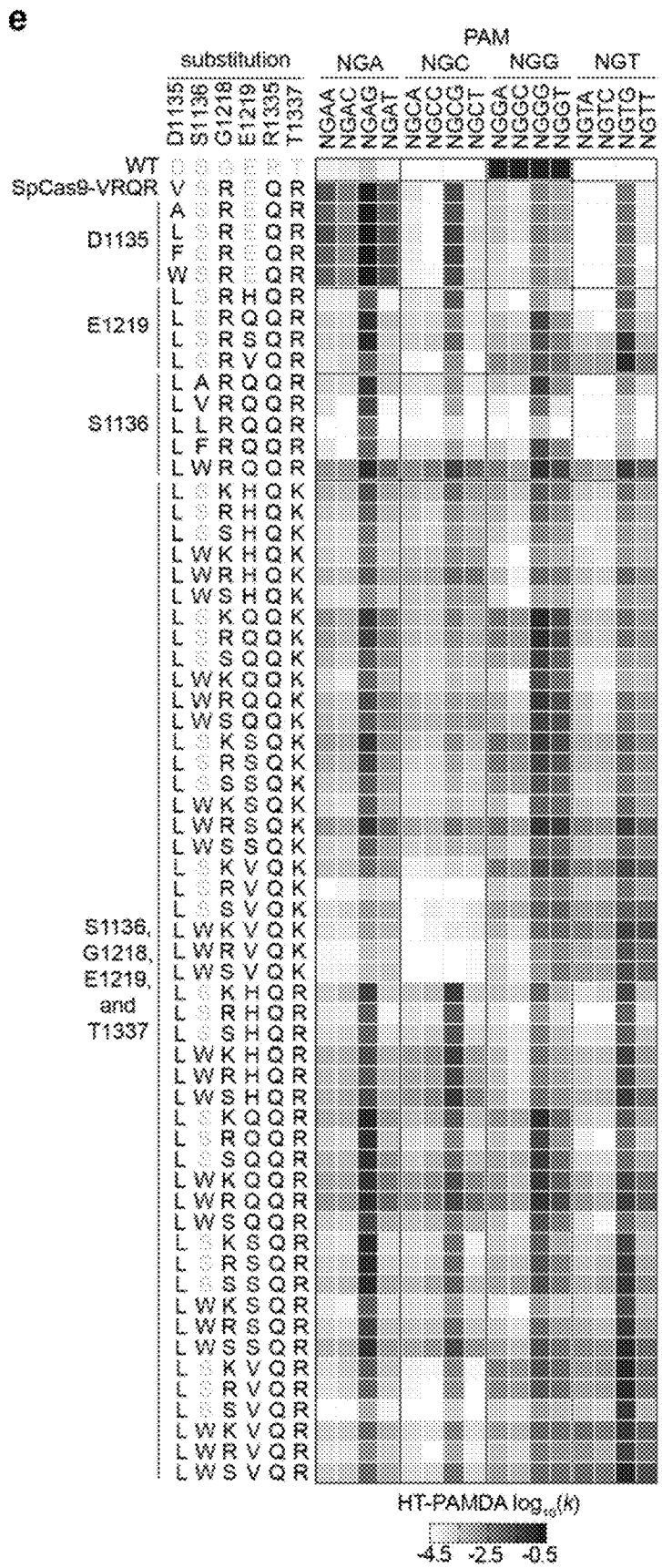

To more thoroughly investigate the impacts of amino acid substitutions in PI domain residues, we first developed a high-throughput PAM determination assay (HT-PAMDA) to comprehensively profile the PAM preferences of a large number of SpCas9 variants (FIGS. 6a-d and see other Examples below). HT-PAMDA accurately replicated the PAM profiles of wild-type (WT) SpCas9 and other previously described variants (FIG. 1c and FIG. 6d). To engineer an SpCas9 variant capable of more relaxed targeting, we utilized HT-PAMDA to sequentially determine the contributions of dozens of substitutions at five PI-critical positions D1135, S1136, G1218, E1219, and T1337 in the context of SpCas9-VRQR (FIG. 6e and see other Examples below). We identified several variants bearing combinations of rational substitutions at these five important residues that exhibited more balanced tolerances for any nucleotide at the $3^{rd}$ and $4^{th}$ PAM positions (FIG. 1c and FIG. 6e). One variant bearing D1135L/S1136W/G1218K/E1219Q/R1335Q/T1337R substitutions, henceforth named SpG, exhibited the most even targeting of NGA, NGC, NGG, and NGT PAMs.

We then compared the human cell activities of WT SpCas9 to SpG and nearly all intermediate variants to corroborate our HT-PAMDA findings. Using an optimal NLS architecture[26] (FIGS. 7A-D), we examined the human cell editing activities of this large collection of variants on four sites with NGA, NGC, NGG, and NGT PAMs (FIGS. 8a and 8b, and see other Examples below). These experiments revealed high-activity editing on the four NGN PAM sites with SpG (FIG. 1d), results that were consistent with the PAM preference of SpG characterized using HT-PAMDA (FIG. 6f). We then sought to bolster the activity of SpG through the addition of non-specific contacts mediated by L1111R and A1322R substitutions, mutations that are necessary for the NGN PAM tolerance of SpCas9-NG[22] (FIGS. 8c and 8d). However, the L1111R and A1322R substitutions were detrimental to the human cell editing activities of SpG, albeit without alteration of PAM preference (FIGS. 8e-f and 6f-g, respectively; see other Examples below).

Example 2. SpG Activities as a Nuclease, CBE, and ABE

Given the broad compatibility of SpG with NGN PAMs as determined by HT-PAMDA but across only four target sites in human cells, we sought to more thoroughly compare its nuclease activity in human cells against WT SpCas9, xCas9 (3.7), and SpCas9-NG. We directly compared the editing activities of SpG to these three nucleases on 78 sites bearing NGNN PAM sequences that encompassed an approximately even distribution of nucleotide identities in the $3^{rd}$ and $4^{th}$ positions of the PAM (FIG. 9a). Our assessment recapitulated the PAM preference of WT SpCas9[7,8], with a mean editing activity of 72.8% on sites with NGG PAMs and greatly reduced 4.7% mean editing across the remaining NGH sites (where H is A, C, or T; FIG. 1e). SpG exhibited the highest mean editing activities across all NGN PAM sites, averaging 51.2% on sites with NGG PAMs and 53.7% on sites with NGH PAMs (FIG. 1e). Finally, of the two variants previously reported to recognize sites with NGN PAMs, xCas9 displayed more modest editing (42.2% on NGG and 12.5% across NGH), while SpCas9-NG editing activities were even across NGN PAM sites but lower compared to SpG (46.9% on NGG and 46.0% across NGH; FIG. 1e).

To better understand the PAM requirements of each of the NGN-PAM variants, we utilized HT-PAMDA to profile SpG, xCas9, and SpCas9-NG (FIG. 1f, FIG. 6f). These experiments demonstrated that SpG exhibited the most even and robust targeting of all NGN PAMs (ranking SpG>SpCas9-NG>xCas9; FIG. 1f), findings that were consistent with the results of our 78 site human cell experiment (FIG. 1e). Closer inspection of our HT-PAMDA and human cell data revealed minor evidence of $1^{st}$ PAM, $4^{th}$ PAM, or $1^{st}$ spacer position bias for WT SpCas9, SpG, or SpCas9-NG (FIGS. 9b-d and see other Examples below); this analysis also attributed the decreased activities observed with xCas9 to a preference for a $4^{th}$ PAM position C, making targeting of sites with NGND PAMs (where D is A, G, or T) less efficient (FIG. 9e and see other Examples below). Generally, HT-PAMDA values for each NGNN PAM class correlated well with mean editing activities in human cells (FIG. 9f).

Together, these results demonstrate that SpG is the most efficient and broadly targeting NGN PAM nuclease described to-date.

Given the ubiquitous use of base editor (BE) technologies to mediate single nucleotide substitutions in various organisms[17,18,27], next we investigated whether the improved activities of SpG could enhance BE activities across sites with NGN PAMs. We compared C-to-T editing with WT SpCas9, xCas9, SpCas9-NG, and SpG BE4max cytosine base editor[28] (CBE) constructs across 22 endogenous sites in human cells bearing NGNN PAMs (FIG. 10a). We observed that whereas WT- and xCas9-CBE exhibited mean C-to-T editing efficiencies above 15% only on sites with NGG PAMs, both SpG- and SpCas9-NG-CBE were capable of mean C-to-T editing above 23% across NGN sites (FIG. 1g) and displayed typical CBE substrate preferences (FIG. 10b). To ensure that the CBE versions of the PAM variants harbored the same PAM profiles as the nucleases, we developed a modified CBE high-throughput PAM determination assay (CBE-HT-PAMDA) (FIG. 10c and see other Examples below). The PAM compatibilities of the CBEs were largely consistent with the preferences of the nucleases (compare FIGS. 1h and 1f, respectively, and see FIGS. 10d and e).

Beyond C-to-T editing, adenine base editor (ABE) constructs have also been developed that mediate A-to-G edits[18]. Thus, we also compared the A-to-G editing potencies of WT SpCas9, xCas9, SpCas9-NG, and SpG in the ABEmax architecture[28] across 21 endogenous sites harboring NGNN PAMs (FIG. 11a). Similar to our observations for CBEs, WT- and xCas9-ABE could only efficiently perform A-to-G edits on target sites with NGG PAMs (FIG. 1i). However, both SpG- and SpCas9-NG-ABE efficiently edited target sites with NGNN PAMs, where SpG-ABE exhibited the most robust activity across all NGNN sites (FIG. 1i) with typical ABE substrate preferences (FIG. 11b).

Collectively, these results demonstrate that SpCas9 PAM preference can be relaxed to a single NGN nucleotide motif by rationally designing a more tolerant PI domain, and that the SpG variant derived using this strategy exhibits the most robust nuclease, CBE, and ABE activities across NGN PAMs described to-date.

Example 3. Engineering SpCas9 Variants Capable of Targeting NR PAMs

Notwithstanding the efficient modification of sites with NGN PAMs using SpG, many genomic regions remain inaccessible to genome editing. Because we observed efficient modification of sites bearing NGN PAMs with SpG, we speculated that SpG could be utilized as a molecular scaffold upon which to further relax PAM specificity. To alter recognition of the $2^{nd}$ position of the PAM, we focused on mutating R1333 since substitution to glutamine might enable access to sites harboring NAN PAMs, presumably by forming a base specific contact with the adenine base in the second position of the PAM[8,20,24] (FIG. 2a). However, our initial tests of SpG (R1333Q) nearly abolished activity in human cells against four sites bearing NRN PAMs (where R is A and G) (FIG. 2b), revealing that the R1333Q alone was insufficient to enable highly active targeting of NAN PAMs (consistent with previous reports for WT SpCas9[8,20]). Interestingly, contrary to our previous finding that L1111R and A1322R substitutions negatively impacted SpG activity (FIG. 8d), we now observed that the addition of these non-specific DNA contacts were able to rescue activity of SpG (R1333Q) across the four sites bearing NRN PAMs in human cells (FIG. 2b). Concurrent HT-PAMDA experiments to analyze the same variants corroborated a general relaxation of PAM specificity against NR PAMs but with a lower overall activity (FIG. 2c).

Next, to determine whether the R1333Q substitution was the most permissive for recognition of an expanded number of PAMs, we utilized HT-PAMDA to investigate whether variants harboring other amino acid substitutions at residue 1333 might be more amenable to highly active and broad targeting of NRN PAMs. Systematic evaluation of SpG (L1111R/A1322R) variants harboring all 20 possible amino acids at residue 1333 revealed that the range substitutions at this position cause different $2^{nd}$ PAM position preferences and overall levels of activity (FIG. 12a). Surprisingly, variants bearing R1333 substitutions to alanine, cysteine, or proline conferred the most efficient collective targeting of NRN PAMs. Human cell experiments against the same four sites harboring NRN PAMs demonstrated that one SpG (L1111R/A1322R) variant that also harbored an R1333P substitutions exhibited greater activity on NRN PAMs compared to the precursor R1333Q-containing variants (FIG. 2b). HT-PAMDA experiments confirmed these observations (FIG. 2c).

Given that the addition of L1111R and A1322R to SpG improved on-target activity, we wondered whether additional analogous substitutions could further enhance editing of sites with NRN PAMs. To do so, we utilized SpCas9 crystal structures to identify other positions in the PI domain whose substitution to positively charged residues might be expected to increase activity by forming novel non-specific DNA contacts (FIG. 2a). We utilized HT-PAMDA to determine the single or combinatorial effects of three such substitutions, A61R, G1104K, or N1317R, in the context of SpG (L1111R/A1322R) variants also bearing R1333A, R1333C, or R1333P substitutions (FIG. 2c and FIG. 12b). This analysis revealed that different combinations of the three non-specific substitutions were well-tolerated by nearly all variants, and that the NRN PAM-preferences of variants harboring R1333A, C, or P substitutions were similar by HT-PAMDA.

Figure 12C:
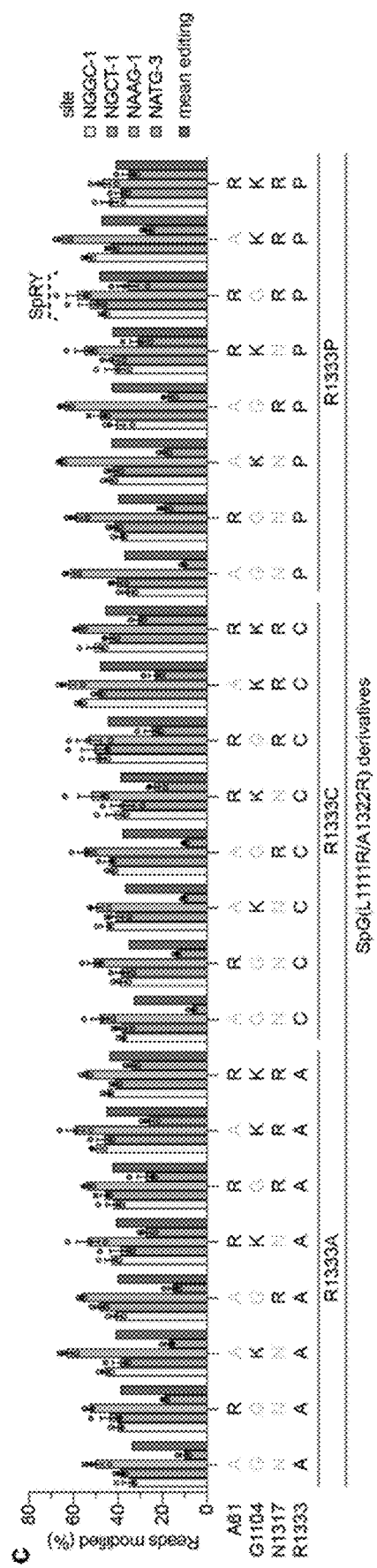
Figure 12D:
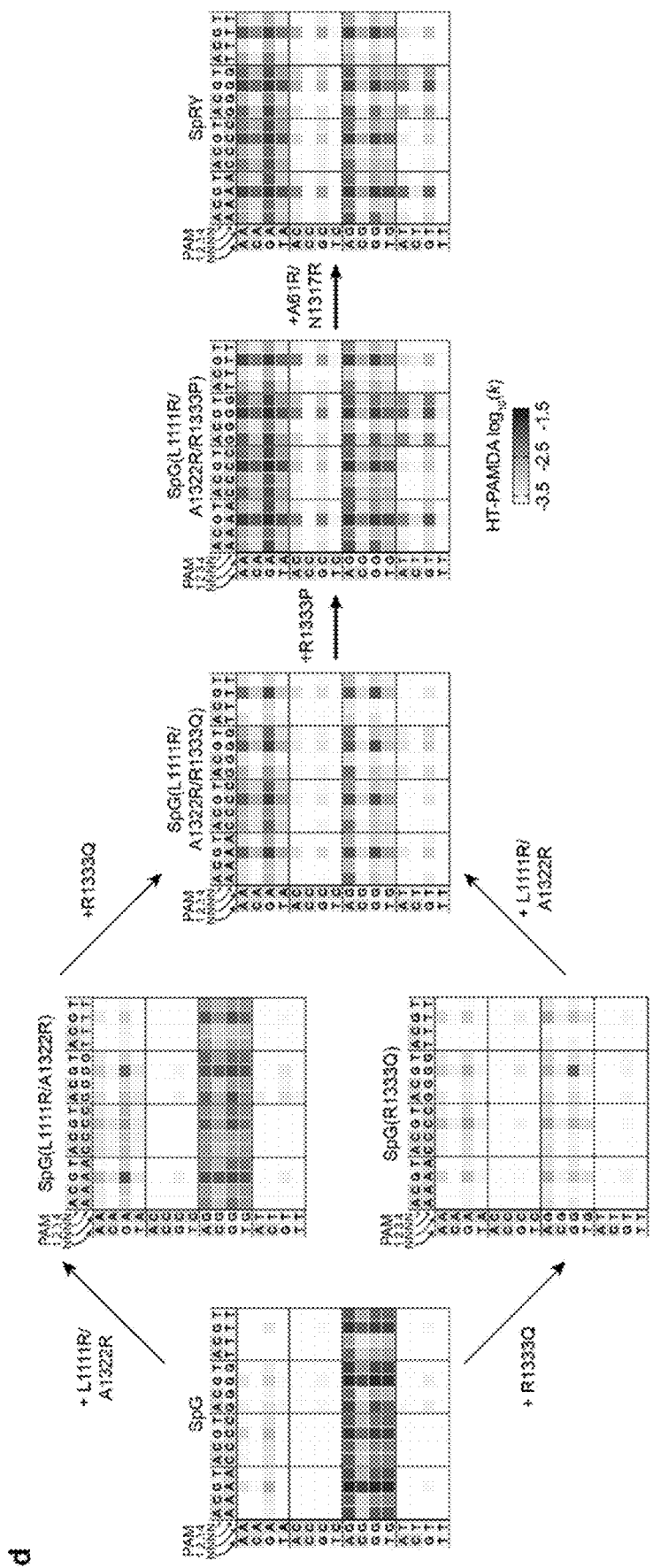

To determine which variant exhibited the highest on-target activity in human cells, we tested this large series of variants against four additional sites bearing NRN PAMs (FIG. 12c). We observed that the SpG (L1111R/A1322R) variant harboring the R1333P substitution and a combination of A61R/N1317R offered the greatest mean editing against NRN PAMs (FIG. 2d). Use of HT-PAMDA to examine the sequential effects of the substitutions encoded by this variant demonstrated a step-wise progression from NGN to NRN PAM preference, and also revealed the surprising finding that this variant may target some NYN PAMs (where Y is C or T; FIG. 12d). Taken together, our human cell and HT-PAMDA data suggest that the SpG (L1111R/A1322R) derivative containing A61R, N1317R, and R1333P substitutions (henceforth referred to as SpRY, for SpCas9 variant capable of targeting NRN>NYN PAMs) enables targeting of sites with NR PAMs.

Example 4. SpRY Activities as a Nuclease, CBE, and ABE in Human Cells

Having established the potential of SpRY to widely expand sequence targeting, we more thoroughly assessed its nuclease activities in human cells. We compared the on-target editing of WT SpCas9 and SpRY across 64 sites, 32 each harboring NANN and NGNN PAMs (FIGS. 13a and 13b, respectively). Using non-saturating nuclease expression conditions in HEK 293T cells, consistent with prior reports[7,8] we observed that WT SpCas9 preferred NGG>NAG>NGA PAMs with negligible targeting of the remaining NRN PAMs (FIG. 3a). In comparison, SpRY was far more effective than WT at targeting sites encoding NRN PAMs, except for sites harboring canonical NGG PAMs (FIG. 3a). Across the 32 sites with NGN PAMs, SpRY often exhibited comparable activities to SpG, though SpG remained the most effective NGN PAM variant (FIGS. 13b and c). Overall, SpRY was capable of efficiently targeting the majority of target sites with NRN PAMs, where the range of activities could not necessarily be explained by PAM preference alone. These results demonstrate, for the first time, the ability to effectively target a range of sites with NAN PAMs using a Cas9 variant.

Combined with our prior observation of modest levels of NYN targeting with SpRY in HT-PAMDA (FIG. 12d), structural analysis of the R1333P substitution in SpRY led us to speculate that R1333P-containing variants might also enable targeting of any base in the $2^{nd}$ PAM position (including thus far unexamined NYN PAMs; FIG. 13d). To test this hypothesis, we examined the activities of WT SpCas9 and SpRY across 31 sites with NYN PAMs (15 NCNN and 16 NTNN sites; FIG. 13e). Surprisingly, SpRY was able to edit 13 of 31 sites (42%) with NYN PAMs to levels higher than 20% modification, compared to 0 sites with WT SpCas9 (FIG. 3b). While the mean editing activities on sites with NYN PAMs were approximately half of what we observed on sites with NRN PAMs, the activities were far greater than the essentially negligible editing with WT SpCas9 (FIG. 3b). The PAM preference of SpRY as determined by HT-PAMDA was generally consistent with the mean nuclease editing levels for each PAM class (FIG. 13f and see other Examples below), and additional experiments may be required to more thoroughly investigate the substrate requirements of SpRY (FIGS. 13g-j). Collectively, these results demonstrate the ability to target sites with NRN PAMs and some NYN PAMs with SpCas9 for the first time.

Because SpRY enables nuclease targeting of many sites with NNN PAMs in human cells, we examined its compatibility with base editors given their dependence on the availability of PAMs to appropriately position the CBE or ABE edit windows. Assessment of SpRY-CBE across 14 sites bearing NRN PAMs revealed mean C-to-T editing of 38.0% across all substrate cytosines (FIG. 3c), with SpRY-CBE achieving greater than 20% modification of at least one cytosine per site for all but one site (FIG. 14a). Comparatively, WT-CBE modified sites bearing NGG PAMs most efficiently, though was also capable of modifying sites bearing NAG and NGA PAMs, albeit at lower efficiency that SpRY (FIG. 3c and FIG. 14a). We also assessed the activities SpRY-CBE on five high-activity NYN PAM sites from our previous nuclease datasets (see FIG. 13e). For these pre-selected high-activity sites, we observed robust levels of editing compared to negligible editing with WT-CBE (FIG. 3d and FIG. 14b). Similar to our observations for SpG-CBE, SpRY-CBE exhibited typical CBE substrate preferences (FIG. 14c).

We then examined the A-to-G editing activities of SpRY-ABE across 13 sites with NRN PAMs, and also for 5 high-activity sites with NYN PAMs (the latter from FIG. 13e). For the NRN PAM sites, we observed mean A-to-G editing activities of 34.7% with SpRY-ABE on substrate adenines and achieved greater than 20% modification on at least one adenine for 10 of 13 sites (FIG. 3e). With WT-ABE, the most efficient editing was observed on the NGG PAM site and minor editing detected on 3 sites with non-canonical PAMs (FIG. 3e). Across the five pre-selected high activity sites harboring NY PAMs, A-to-G editing activities were generally more modest with SpRY but we did observe editing of one adenine to near 90%; no editing with WT ABEmax was observed on any of the five sites (FIG. 3f). Overall, SpRY-ABE exhibited greater mean A-to-G editing compared to WT-ABE across sites containing NRN and NYN PAMs with typical ABE substrate requirements (FIGS. 14d-f).

Example 5. Expanded Targeting of SpG and SpRY Enables the Generation of Protective Genetic Variants Since the requirement for a PAM by DNA-targeting CRISPR enzymes fundamentally limits applications that require precision targeting, we sought to demonstrate the enabling potential of our broadly targeting variants. In a proof-of-concept application, we leveraged the activities of SpG and the near-PAMless qualities of SpRY to generate biologically relevant substitutions that were previously inaccessible due to a lack of nearby canonical NGG PAMs. We selected ten genetic variants implicated to protect individuals against various diseases including coronary heart disease, type 2 diabetes, osteoporosis, chronic pain, and others[29-35]. To generate the SNPs, we systematically evaluated target sites harboring NRN PAMs using WT-, SpG-, and SpRY-CBEs that would position the intended C-to-T edit within the CBE edit window (FIG. 4). First, with WT-CBE we found that we were unable to efficiently generate the intended edit due to a lack of canonical NGG PAMs for 8 of 10 SNPs, reinforcing the need for variants with expanded targeting capabilities. For the remaining two sites (SLC30A8 M50I and MSTN IVS1), the intended edit was possible with WT-CBEs using targets harboring NAG and NGG PAMs, respectively, but with potentially deleterious bystander editing of other cytosines in the edit window or at lower efficiencies than with SpG- or SpRY-CBEs.

With the expanded targeting ranges of SpG and SpRY, we were able to screen many additional target sites for each SNP. Using the CBE versions of these variants, we efficiently introduced the intended C-to-T edit across all ten targets (FIG. 4). For the majority of the SNPs, we were able to avoid deleterious bystander editing by selecting from several possible target sites, providing options to choose between targets that produce silent or tolerable collateral edits (for example, alternate stop codons in the context of a SNP that causes a premature stop codon) instead of those that cause non-synonymous C-to-T changes. These results demonstrate the utility of SpG and SpRY for higher resolution targeting not only for enabling access to previously un-editable genomic sites, but also the capability to examine additional target sites to avoid detrimental bystander edits.

Example 6. Rationale for Targeted Engineering of SpCas9 PAM Preference

Crystal structures of wild-type (WT) SpCas9 have clearly elucidated the molecular mechanism of PAM recognition by SpCas9, which occurs via bidentate hydrogen bonds between R1333 and R1335 residues in the PAM-interacting (PI) domain and $dG_2$ and $dG_3$ of the NGG PAM, respectively[20] (FIG. 5a). We and others have previously shown that modifications to R1333 or R1335 abrogate nuclease activity[20,8], confirming their indispensable roles for SpCas9 PAM recognition and activity. These observations suggested that other residues must be altered in concert with changes to R1333 and R1335 to retain SpCas9 function while altering PAM specificity. Our previous work to evolve SpCas9 variants that target non-canonical PAMs utilized an unbiased mutagenic approach and identified other PAM-proximal amino acids whose substitution were critical to for altering activity (including D1135, S1136, G1218, E1219, and T1337)[8,21]. The SpCas9-VQR (D1135V/R1335Q/T1337R), VRER (D1135V/G1218R/R1335E/T1337R), and VRQR (D1135V/G1218R/R1335Q/T1337R) variants achieve efficient targeting of non-canonical PAMs through the coordinated substitution of R1335 (to alter the $3^{rd}$ PAM position preference) along with other amino acids mutations in these neighboring positions[8,21].

Structural studies of SpCas9-VQR and VRER revealed the mechanisms of non-canonical PAM recognition by these variants[24,25]. The formation of new base-specific contacts through the R1335Q and R1335E mutations are essential, but not sufficient, for altering recognition of the $3^{rd}$ position of the PAM. For example, structures of SpCas9-VQR bound to an NGAG PAM revealed bidentate hydrogen bonds between R1335Q and $dA_3$ of the non-target strand (NTS) (FIG. 5b). However, the shortened sidechain length of R1335Q necessitates a 1.5 Å displacement of the PAM DNA essential for this interaction (FIG. 5c), a molecular rearrangement supported by the D1135V substitution in the minor groove[8,24,25]. Additionally, the T1337R substitution of SpCas9-VQR can form base-specific hydrogen bond contacts with $dG_4$ of the NTS, contributing to PAM DNA displacement (FIG. 5d). Crystal structures of SpCas9-VRER, an SpCas9 variant that we previously engineered to target NGCG PAM sequences, suggest that the G1218R mutation can form electrostatic interactions with the DNA phosphate group between the third and fourth nucleotides of the NTS[8,24,25] (FIG. 5e). We speculate that the G1218R substitution of SpCas9-VRQR might perform a similar function.

Importantly, for both SpCas9-VQR and SpCas9-VRER no single substitution altered PAM preference while maintaining potent activity, suggesting a strong interdependence and co-evolutionary relationship of the residues surrounding the PAM DNA bases for PAM recognition[8]. Together, our previous engineering studies and subsequent structural work on SpCas9 PAM variants suggest three important considerations and mechanisms for engineering SpCas9 PAM preference: (1) generating amino acid substitutions that create novel base-specific contacts, (2) substitutions that displace the PAM DNA bases to accommodate novel base-specific contacts, and (3) the addition of non-specific contacts to stabilize PAM binding. Furthermore, the observation that individual substitutions did not generate functional variants with altered PAM preferences foretold the necessity of a higher-throughput method to analyze larger collections of variants bearing more complex combinations of substitutions.

Example 7. Hypotheses for Engineering an SpCas9 Variant with a Relaxed PAM Preference To engineer a more broadly targeting SpCas9 variant, we focused on modifying six PAM-proximal residues (D1135, S1136, G1218, E1219, R1335, and T1337). We utilized SpCas9-VRQR as a scaffold for our engineering approach to relax PAM preference since it already possessed a somewhat relaxed PAM preference of NGA>NGNG, it displayed improved activities relative to SpCas9-VQR, and because we could leverage the structural studies of SpCas9-VQR and VRER to infer potential mechanisms of PAM recognition[8, 21, 24, 25].

We first speculated how structure-motivated substitutions of the six PAM-proximal amino acids could relax PAM preference. Because SpCas9-VRQR had demonstrated the ability to target NGNG PAMs (and thus possessed a relaxed tolerance in the $3^{rd}$ position of the PAM), we elected to maintain the R1335Q substitution of SpCas9-VRQR while varying the other five positions. Since a D1135V substitution contributes to the displacement of the PAM DNA bases, we hypothesized that we could tune the displacement of the PAM bases with a combination of hydrophobic substitutions at D1135 and S1136 and that modulating this displacement could facilitate interactions within the major groove (FIG. 5c). We also sought to form non-specific contacts to the DNA by varying the identity of G1218, similar to those formed by G1218R in SpCas9-VRQR and -VRER (FIG. 5e). In SpCas9-VQR the E1219 side chain forms hydrogen bonds that stabilize the R1335Q-$dA_3$ interaction (FIGS. 5b and f), leading us to speculate that E1219 may prevent R1335Q from adopting alternate conformations capable of accommodating different bases in the $3^{rd}$ position of the PAM. We hypothesized that a more electrostatically neutral E1219Q substitution might support alternative conformations of R1335Q that could lead to a more relaxed tolerance within the $3^{rd}$ PAM position (FIGS. 5f-i). Finally, we hypothesized that positively charged arginine or lysine substitutions at position T1337 might form compensatory contacts to stabilize PAM DNA binding and contribute to the displacement of the DNA towards R1335Q.

Example 8. Optimization and Validation of HT-PAMDA

To facilitate a large-scale rational engineering approach to develop SpCas9 variants capable of targeting NGN PAM sequences, we required a high-throughput PAM determination assay (HT-PAMDA) that could rapidly and comprehensively profile the PAM preferences of dozens or even hundreds of SpCas9 variants. A scalable assay to fulfill these criteria would: (1) preclude protein expression and purification (as we and others have previously done for Cas12a variants[36,39]), (2) would optimally be performed in vitro with conditions approximating a human cell context, and (3) would not be performed in bacteria or bacterial lysates (as we had done previously for SpCas9 and SaCas9 variants[8,40]). To enable our studies, we developed the HT-PAMDA that first relies on the expression of SpCas9 variants in human cells, a step that can be easily arrayed and thus performed in high-throughput (FIG. 6a). The variable expression of SpCas9 proteins across different transfections is measurably linked to the expression of a 2A-EGFP fluorescence, permitting the normalization of SpCas9 protein concentrations by using a defined amount of EGFP based on a fluorescein standard curve. A constant amount of SpCas9 human cell lysate is then subject to a time-course in vitro cleavage reaction of two separate libraries harboring distinct spacer sequences and 8 nucleotide randomized PAM sequences (FIG. 6a). Targeted sequencing of the libraries at various time points allowed quantitation of the rate of depletion of each PAM from the population over time; the rate constant for each PAM therefore enables us to calculate comprehensive PAM preferences for each SpCas9 variant. In general, we found that the HT-PAMDA profiles for WT SpCas9 and SpCas9-VQR were highly reproducible across two different spacer sequences (FIG. 6b) and across technical replicates (FIG. 6c). Furthermore, the HT-PAMDA profiles of WT SpCas9, SpCas9-VQR, and SpCas9-VRER were consistent with their previously described PAM preferences established using alternate methods (FIG. 6d). These results demonstrate that HT-PAMDA recapitulates known PAM preferences and can in principle be scaled to large numbers of SpCas9 variants.

Example 9. Engineering of SpG for Targeting Sites with NGN PAMs

To relax the PAM preference of SpCas9, we generated a series of variants bearing structure-motivated substitutions in residues D1135, S1136, G1218, E1219, R1335, and T1337 using SpCas9-VRQR as a scaffold. Based on this hypotheses (see above), we sequentially tested hydrophobic substitutions at D1135, substitutions bearing different charges at E1219, and hydrophobic substitutions at S1136. The PAM preferences for variants bearing these substitutions were determined by HT-PAMDA, revealing differential contributions to PAM recognition by substitutions at D1135, S1136, and E1219 (FIG. 1c and FIG. 6e). Examination of the activities of this collection of variants against sites bearing NGAT, NGCC, NGGG, and NGTA PAMs in human cells recapitulated our HT-PAMDA observations and demonstrated that the concurrent substitution of several amino acids enables high activity targeting of non-canonical PAMs (FIG. 8a). One variant bearing D1135V/S1136W/ G1218R/E1219Q/R1335Q/T1337R substitutions improved human cell editing relative to SpCas9-VRQR by 2 to 53-fold on the non-NGA sites, and maintained 87% of the activity on the NGAT site (FIG. 8a). While this variant displayed robust activity, our method of sequential mutagenesis to this point did not allow us to examine the more complete interdependence of the amino acid substitutions. We proceeded to assess all combinations of wild-type residues and the substitutions S1136W, E1219S/V/H/Q, G1218R/K/S, and T1337R/K. The forty-eight variants bearing combinations of the wild-type and substituted residues were profiled by HT-PAMDA (FIG. 1c and FIG. 6e) and assessed for on-target editing using the same four sites in human cells with NGAT, NGCC, NGGG, and NGTA PAMs (FIG. 8b). The combined HT-PAMDA and human cell analysis revealed that the variant encoding D1135L/S1136W/G1218K/ E1219Q/R1335Q/T1337R substitutions (re-named to SpG) displayed the most even PAM tolerance and the highest average activity across the four sites in human cells.

Example 10. Energetic Supplementation Via Non-Specific Contacts

To further improve the on-target activity of SpG, we wondered whether the variant could tolerate other substitutions intended to form non-specific DNA contacts and thus improve the overall interaction energy of SpG with the PAM. A similar strategy was previously described for SpCas9-NG, which harbors L1111R and A1322R substitutions hypothesized to form DNA backbone contacts to compensate for the loss of base-specific interactions to the $3^{rd}$ position of the PAM caused by the R1335V substitution[22]. To investigate this hypothesis, we first determined whether the L1111R and A1322R substitutions are essential for the activities of SpCas9-NG. We compared the on-target editing of SpCas9-NG to the R1111L, R1322A, and R1111L/ R1322A derivative variants that lack the supplementary energetic contacts across 16 sites harboring NGNN PAMs in human cells (FIGS. 8c and d). We found that the inclusion of both arginine substitutions is necessary for the activities observed with SpCas9-NG.

We then determined whether the same substitutions could improve the editing efficiencies of SpG by generating derivative variants harboring L1111R, A1322R, or both substitutions. When we assessed the activities of these variants across the same 16 sites harboring NGNN in human cells, we surprisingly observed a reduction in the on-target activities for 14 of 16 sites with most variants (FIGS. 8e and f). These results suggest that the substitutions in SpG that result in expanded PAM recognition do not require energetic supplementation, or possibly that the L1111R and A1322R substitutions are not compatible with SpG residues. HT-PAMDA experiments to determine the PAM profiles of these variants showed that the presence or absence of L1111R and A1322R in either variant did not appear to alter their PAM preferences (FIGS. 6f and 6g), supporting the hypothesis that the major roles of L1111R and A1322R substitutions are energetic rather than PAM preference altering.

Example 11. Sequence Preferences of WT, xCas9, SpCas9-NG, and SpG

We utilized our HT-PAMDA and human cell datasets (FIGS. 6A-G and 9A-F respectively) to more thoroughly characterize the sequence preferences of WT SpCas9, xCas9 $(3.7)^{23}$, SpCas$^9$-NG$^9$, and SpG. We observed reasonable correlations between average human cell editing efficiencies on NGNN PAMs and the $\log_{10}$ PAMDA rate constants, verifying that the preferences revealed in HT-PAMDA were replicated in human cells (FIG. 9f). Our characterization of WT SpCas9 PAM preference is largely consistent with prior reports[8,5,7], revealing that sites encoding NGG PAMs were most efficiently targeted followed by a minor preference for sites with NAG>NGA PAMs (FIG. 6d). For WT SpCas9, xCas9, SpCas9-NG, and SpG, we observed minimal evidence of a $1^{st}$ PAM position preference (FIGS. 6d, 6f, and 9b) and minor influence of the $1^{st}$ position of the spacer (FIG. 9d).

Based on our HT-PAMDA and human cell editing data (FIGS. 6f and 9a, respectively), we examined the $3^{rd}$ PAM position preferences for each NG variant. We found that xCas9 preferred NGG>>NGA=NGT>NGC, and that SpCas9-NG and SpG exhibited more even tolerances of NGN PAMs (see FIG. 1e and FIG. 6f). When considering the $4^{th}$ PAM position, xCas9 preferred NGNC>NGND where once again SpCas9-NG and SpG were capable of more even targeting of NGNN PAMs (see FIGS. 6f and 9c). Our human cell-based cytosine and adenine base editor (CBE and ABE, respectively) PAM characterizations of xCas9, SpCas9-NG, and SpG were largely consistent with our nuclease observations, with differences likely attributable to the fact that we performed fewer CBE and ABE experiments (22 and 21 sites, respectively) compared to our nuclease datasets (78 sites; FIGS. 1e, 1g and 1i).

Example 12. PAM Profile for xCas9

While the initial description of xCas9 reported targeting capabilities including NGN PAMs in human cells[23], our data suggests the targeting range of xCas9 to be more narrow. Across 78 sites in human cells, xCas9 averaged lower modification rates than WT SpCas9 and did not surpass 20% mean modification of sites encoding NGA, NGC, or NGT PAMs (FIG. 1e). HT-PAMDA also revealed that xCas9 can only appreciably target NGAC, NGTC, and NGGN PAMs (FIG. 6f). Interestingly, xCas9 also exhibited reduced activity on NGG PAMs compared to WT SpCas9, SpCas9-NG, and SpG, despite the retention of both R1333 and R1335, the critical arginine residues for NGG PAM recognition (FIG. 1e, FIG. 6f). Of the substitutions in xCas9, only E1219V is in close proximity to the PAM; this substitution might disrupt the E1219-R1335-dG$_3$ hydrogen-bonding network that stabilizes NGG PAM recognition, consistent with prior structural analysis[41]. We characterized the PAM preference of the SpCas9 (E1219V) single mutant and found that the PAM preference of xCas9 was largely attributable to this single mutation (FIG. 6g). Analysis of our human cell data corroborated HT-PAMDA findings that xCas9 has a strong preference for cytosine in the 4$^{th}$ position of the PAM, both in the context of NGG and NGH PAMs that nearly completely explained non-canonical PAM targeting with xCas9 (FIGS. 9c and e). A preference for cytosine in the 4$^{th}$ position of the PAM is not observed with WT SpCas9, SpCas9-NG, and SpG (FIGS. 9c and e). Collectively, our human cell (FIGS. 9c and e), HT-PAMDA (FIGS. 6f and g), and CBE-HT-PAMDA (FIG. 10d; see below) characterizations of xCas9 are more consistent with a PAM preference of NGGN>NGDC.

Example 13. Optimization and Validation of CBE-HT-PAMDA

The PAM requirements of base editor protein fusions have generally been assumed to be consistent with the PAM requirements of CRISPR nucleases, yet it remains possible that they exhibit distinctive preferences. To determine whether or not SpCas9 nucleases and base editors (BEs) exhibit consistent PAM profiles, we adapted the HT-PAMDA assay to function in the absence of SpCas9-mediated DNA cleavage. The PAM profiles generated by HT-PAMDA are dependent on the depletion of library members over time due to plasmid cleavage, yet base editors do not intentionally cleave DNA (rather, DNA binding events are followed by nicking and deamination). To directly address this question, we adapted HT-PAMDA to develop a cytosine base editor high-throughput PAM determination assay (CBE-PAMDA-HT; FIG. 10c). CBE-HT-PAMDA is similar to HT-PAMDA, but instead of double-strand DNA cleavage relies on SpCas9-based nicking and deamination of a cytosine by the tethered rAPOBEC1 domain. The combination of a target strand nick and a non-target strand deamination event is later converted to a double strand break using USER enzyme to remove the uracil base and cleave the non-target strand backbone, depleting CBE-targetable PAM-containing substrates from the library (FIG. 10c). With CBE-PAMDA-HT, we observed comparable CBE-based PAM profiles for WT-SpCas9, xCas9, SpCas9-NG, and SpG (FIG. 10d) relative to the nuclease-based PAM profiles for the same proteins (FIGS. 6d and f). We also observed reasonable agreement the between HT-PAMDA and CBE-HT-PAMDA $\log_{10}$ rates for the PAMs of the same four variants (FIG. 10e). Thus, we conclude that nuclease and CBE versions of different SpCas9 variants exhibit comparable PAM profiles.

Example 14. Characterization of SpRY Sequence Preferences

We explored whether the range of activities displayed by SpRY across sites bearing NR and NY PAMs could be explained by aspects of PAM preference. Our HT-PAMDA characterization of SpRY revealed a strong NR>NY PAM preference, and suggested a number of preferences at other positions (FIG. 12d). When comparing HT-PAMDA $\log_{10}$ rate constants to the mean human cell editing efficiencies on NNN PAMs, we found that while HT-PAMDA accurately characterized the PAM preference of wild-type SpCas9 in human cells, the assay was less effective for SpRY (FIG. 13f). We expect that this discrepancy is due to the vastly different PAM compatibilities of WT SpCas9 and SpRY, leading to almost an order of magnitude difference in the number of targetable library members in the HT-PAMDA assay for each protein. Because HT-PAMDA infers PAM preference based on the rate of depletion of targetable PAMs by sequencing library members harboring non-compatible PAMs, there is a great stoichiometric between WT SpCas9 and SpRY when considering targetable and non-targetable library members.

We also analyzed our human cell modification data to determine whether SpRY displayed PAM or PAM-proximal sequence preferences. In addition to the NR>NY preference in the 2$^{nd}$ position of the PAM, we observed varying degrees of sequence tolerance in 1$^{st}$, 3$^{rd}$, and 4$^{th}$ positions of the PAM as well as the 1$^{st}$ position of the spacer (FIGS. 13g-j). Given the moderate number of sites that we examined (32 endogenous sites bearing NANN PAMs, 32 with NGNN PAMs, and 31 with NYNN PAMs; FIGS. 13a, b, and e, respectively) additional higher-throughput experiments may be required to more completely assess the in vivo PAM requirements of SpRY.

Example 15. Genome-Wide Specificity Analysis of SpG and SpRY

An important consideration for genome editing is the ability to mitigate potential off-target effects. To reduce off-target editing observed with WT SpCas9, we previously engineered a high-fidelity variant of SpCas9 (SpCas9-HF1) with improved genome-wide specificity (Kleinstiver et al., Nature 529, 490-495 (2016)). Since the relaxed PAM tolerances of SpG and SpRY can, in principle, lead to recognition of new off-target sites, we first tested whether our new variants were compatible with the fidelity-enhancing substitutions of SpCas9-HF1. Across several target sites bearing different PAMs, we observed that WT, SpCas9-NG, SpG, SpRY, and their HF1 derivatives exhibited comparable levels of on-target modification (FIGS. 16A and 17A).

We then utilized the GUIDE-seq method (Tsai et al., Nature Biotechnology 33, 187-189 (2015)) to analyze the genome-wide specificity profiles of these variants. In transfections containing the GUIDE-seq double-stranded oligodeoxynucleotide (dsODN) tag, we also observed similar levels of on-target editing between WT, SpG, SpRY, and their HF1 derivative variants (FIGS. 17B-F). Analysis of GUIDE-seq experiments revealed that SpG and SpRY exhibited a somewhat increased propensity for off-target editing compared to WT SpCas9, albeit at similar absolute levels previously reported for WT SpCas9 (Tsai et al., Nature Biotechnology 33, 187-189 (2015)) (FIG. 16B). Nearly all novel off-targets for SpG and SpRY were attributable to the expanded PAM recognition by these variants (FIGS. 18A-C). Importantly, the HF1 variants were able to eliminate nearly all off-target editing events (FIG. 16B) and substantially enrich the fraction of total editing events observed at the on-target sites (FIG. 16C). These results demonstrate that SpG- and SpRY-HF1 offer improved fidelity for applications that necessitate high specificity.

Example 16. Improved A-to-G Editing with ABE8.20 and ABE8e Versions of SpG and SpRY Two recent studies reported the development of improved adenine base editors (ABEs) with enhanced A-to-G editing efficiencies, including ABE (8.20 m) (Gaudelli et al., *Nature Biotechnology* 38, 892-900 (2020)) and ABE8e (Richter et al., *Nature Biotechnology* 38, 883-891 (2020)). To determine whether the enhanced ABE domains could further improve the base editing efficiencies of SpG and SpRY, we generated fusions of both SpCas9 PAM variants to the ABE (8.20 m) and ABE8e domains and investigated their on-target base editing efficiencies (FIGS. 19A and 19B). First, we compared the activities of wild-type (WT) SpCas9, SpG, and SpRY ABEs fused to the prototypical ABE (7.10) along with the improved ABE (8.20 m) and ABE8e on a single target site with an NGG PAM (FIG. 19A). For all 3 Cas9 variants, only low levels of A-to-G editing were detectable with the ABE (7.10) fusions. However, with ABE (8.20 m) and ABE8e fusions, we observed improved on-target editing efficiencies (ranking the on-target efficiencies of the ABE domains 8e>8.20 m>7.10). Next, we compared SpRY fusions to ABE (7.10), ABE (8.20 m), and ABE8e using two additional gRNAs targeted to sites bearing non-canonical and low activity NCT PAMs (FIG. 19B). Once again, we observed that the 7.10 domain produced the lowest levels of on-target A-to-G editing, and that the ABE (8.20 m) and ABE8e constructs could dramatically improve SpRY-ABE activity.

Taken together, our results demonstrate that SpG and SpRY function efficiently in the context of various base editor fusions, including ABE (8.20 m) and ABE8e.

Example 17. Use of SpRY as a Custom Site-Specific Endonuclease In Vitro

The discovery of restriction enzymes over 50 years ago transformed the field of molecular biology, enabling the site-specific cleavage and subsequent assembly of different DNA fragments to generate novel molecular constructs. However, the strict and non-comprehensive recognition motifs of restriction enzymes limits the ability to programmably and precisely cleave sequences in a DNA substrate, making certain in vitro applications time consuming, inefficient, or impossible. To overcome these limitations, we investigated whether SpRY could enable programmable endonuclease-mediated cleavage of DNA substrates in vitro. We hypothesized that the ability of SpRY to act in a near-PAMless manner could allow it to act as a guide RNA (gRNA) programmed endonuclease with unparalleled flexibility, which would enable various molecular cloning workflows and other in vitro applications.

To determine if SpRY could be utilized as a programmable site-specific endonuclease in vitro, we assembled separate ribonucleoprotein (RNPs) complexes of comprised wild-type SpCas9, SpG, and SpRY along with a series of guide RNAs (gRNAs) targeted to 18 different sites in a plasmid (Table 6). We performed in vitro cleavage reactions with each RNP on a linearized DNA substrate, taking aliquots at timepoints of 1, 6, 36 and 216 minutes for visualization and analysis of substrate cleavage (FIG. 20). First, with wild-type SpCas9, we observed complete cleavage of the substrate by the 6 minute timepoint when using either of two gRNAs targeted to sites with NGG PAMs (FIG. 20). We also observed near-complete cleavage by the final 216 minute timepoint of two additional target sites bearing NGAG and NTGG PAMs, consistent with the ability of SpCas9 to weakly recognize target sites with NGA PAMs or shifted NNGG PAMs. Next, with SpG RNPs we observed rapid and complete cleavage only when programmed with gRNAs targeted to sites with NGN PAMs (FIG. 20). Finally, with SpRY RNPs, by the final 216 minute timepoint, we observed essentially complete cleavage of the DNA substrate irrespective of the gRNA (or PAM of the target site) that was tested. Importantly, SpRY effectively targeted all sites that were previously uncleavable with wild-type SpCas9 or SpG.

Together these results indicate that SpRY can be harnessed as a programmable site-specific endonuclease. The application of SpRY as a customizable DNA targeting enzyme has the potential to revolutionize molecular cloning techniques and other in vitro applications.

TABLE 6

List of target sites and oligonucleotides for in vitro cleavage reactions.

| target site ID | target site spacer | # | 4 nt PAM | oligo ID | oligo sequence (to generate the sgRNA via in vitro transcription) | # |
|---|---|---|---|---|---|---|
| NGGC-1 | GCGGTATCAT TGCAGCACTG | 4. | GGGC | oKAC1289 | TTCTAATACGACTCACTATAGCGGTATCATTGC AGCACTGGTTTTAGAGCTAGA | 5. |
| NGGG-1 | GCTCTTGCCC GGCGTCAATA | 6. | CGGG | oKAC1290 | TTCTAATACGACTCACTATAGCTCTTGCCCGGC GTCAATAGTTTTAGAGCTAGA | 7. |
| NGTA-1 | GGCCACCACT TCAAGAACTC | 8. | TGTA | oKAC1291 | TTCTAATACGACTCACTATAGGCCACCACTTCA AGAACTCGTTTTAGAGCTAGA | 9. |
| NGAG-1 | GATACCTACA GCGTGAGCTA | 10. | TGAG | oKAC1284 | TTCTAATACGACTCACTATAGATACCTACAGCG TGAGCTAGTTTTAGAGCTAGA | 11. |
| NGCA-1 | GGTAACTGGC TTCAGCAGAG | 12. | CGCA | oKAC1285 | TTCTAATACGACTCACTATAGGTAACTGGCTTC AGCAGAGGTTTTAGAGCTAGA | 13. |
| NGTT-1 | GCTCACGCTG TAGGTATCTC | 14. | AGTT | oKAC1294 | TTCTAATACGACTCACTATAGCTCACGCTGTAG GTATCTCGTTTTAGAGCTAGA | 15. |
| NAAT-1 | GATCGTTGGG AACCGGAGCT | 16. | GAAT | oKAC1275 | TTCTAATACGACTCACTATAGATCGTTGGGAAC CGGAGCTGTTTTAGAGCTAGA | 17. |
| NACA-1 | GCGAGGTATG TAGGCGGTGC | 18. | TACA | oKAC1254 | TTCTAATACGACTCACTATAGCGAGGTATGTAG GCGGTGCGTTTTAGAGCTAGA | 19. |

TABLE 6-continued

List of target sites and oligonucleotides for in vitro cleavage reactions.

| target site ID | target site spacer | # | 4 nt PAM | oligo ID | oligo sequence (to generate the sgRNA via in vitro transcription) | # |
|---|---|---|---|---|---|---|
| NATC-1 | GGGATCATGTAACTCGCCTT | 20. | GATC | oKAC1282 | TTCTAATACGACTCACTATAGGGATCATGTAACTCGCCTTGTTTTAGAGCTAGA | 21. |
| NAGG-1 | GGTAACAGGATTAGCAGAGC | 22. | GAGG | oKAC1280 | TTCTAATACGACTCACTATAGGTAACAGGATTAGCAGAGCGTTTTAGAGCTAGA | 23. |
| NCAT-1 | GGAACCGGAGCTGAATGAAG | 24. | CCAT | oKAC1297 | TTCTAATACGACTCACTATAGGAACCGGAGCTGAATGAAGGTTTTAGAGCTAGA | 25. |
| NCCG-1 | GGCCCCAGTGCTGCAATGAT | 26. | ACCG | oKAC1264 | TTCTAATACGACTCACTATAGGCCCCAGTGCTGCAATGATGTTTTAGAGCTAGA | 27. |
| NCGC-1 | GCAATGATACCGCGAGACCC | 28. | ACGC | oKAC1266 | TTCTAATACGACTCACTATAGCAATGATACCGCGAGACCCGTTTTAGAGCTAGA | 29. |
| NCTT-1 | GATAACTACGATACGGGAGG | 30. | GCTT | oKAC1305 | TTCTAATACGACTCACTATAGATAACTACGATACGGGAGGGTTTTAGAGCTAGA | 31. |
| NTAC-1 | GCAAACTATTAACTGGCGAA | 32. | CTAC | oKAC1307 | TTCTAATACGACTCACTATAGCAAACTATTAACTGGCGAAGTTTTAGAGCTAGA | 33. |
| NTCC-1 | GGCGAACTACTTACTCTAGC | 34. | TTCC | oKAC1270 | TTCTAATACGACTCACTATAGGCGAACTACTTACTCTAGCGTTTTAGAGCTAGA | 35. |
| NTGG-1 | GGTGCCTCACTGATTAAGCA | 36. | TTGG | oKAC1271 | TTCTAATACGACTCACTATAGGTGCCTCACTGATTAAGCAGTTTTAGAGCTAGA | 37. |
| NTTA-1 | GATGGCATGACAGTAAGAGA | 38. | ATTA | oKAC1314 | TTCTAATACGACTCACTATAGATGGCATGACAGTAAGAGAGTTTTAGAGCTAGA | 39. |

, SEQ ID NO:

REFERENCES

1. Marraffini, L. A. & Sontheimer, E. J. Self versus non-self discrimination during CRISPR RNA-directed immunity. Nature 463, 568-71 (2010).
2. Heler, R. et al. Cas9 specifies functional viral targets during CRISPR-Cas adaptation. Nature 519, 199-202 (2015).
3. Mojica, F., Díez-Villaseñor, C., García-Martínez, J. & Almendros, C. Short motif sequences determine the targets of the prokaryotic CRISPR defence system. Microbiol Read Engl 155, 733-40 (2009).
4. Deveau, H. et al. Phage Response to CRISPR-Encoded Resistance in Streptococcus thermophilus. J Bacteriol 190, 1390-1400 (2007).
5. Jinek, M. et al. A Programmable Dual-RNA-Guided DNA Endonuclease in Adaptive Bacterial Immunity. Science 337, 816-821 (2012).
6. Sternberg, S. H., Redding, S., Jinek, M., Greene, E. C. & Doudna, J. A. DNA interrogation by the CRISPR RNA-guided endonuclease Cas9. Nature 507, 62-7 (2014).
7. Jiang, W., Bikard, D., Cox, D., Zhang, F. & Marraffini, L. A. RNA-guided editing of bacterial genomes using CRISPR-Cas systems. Nat Biotechnol 31, 233-9 (2013).
8. Kleinstiver, B. P. et al. Engineered CRISPR-Cas9 nucleases with altered PAM specificities. Nature 523, 481-5 (2015).
9. Esvelt, K. M. et al. Orthogonal Cas9 proteins for RNA-guided gene regulation and editing. Nat Methods 10, 1116-21 (2013).
10. Fonfara, I. et al. Phylogeny of Cas9 determines functional exchangeability of dual-RNA and Cas9 among orthologous type II CRISPR-Cas systems. Nucleic Acids Res 42, 2577-90 (2013).
11. Karvelis, T. et al. Rapid characterization of CRISPR-Cas9 protospacer adjacent motif sequence elements. Genome Biol 16, 253 (2015).
12. Zetsche, B. et al. Cpf1 is a single RNA-guided endonuclease of a class 2 CRISPR-Cas system. Cell 163, 759-71 (2015).
13. Elliott, B., Richardson, C., Winderbaum, J., Nickoloff, J. A. & Jasin, M. Gene Conversion Tracts from Double-Strand Break Repair in Mammalian Cells. Mol Cell Biol 18, 93-101 (1998).
14. Findlay, G. M., Boyle, E. A., Hause, R. J., Klein, J. C. & Shendure, J. Saturation editing of genomic regions by multiplex homology-directed repair. Nature 513, 120-3 (2014).
15. Canver, M. C. et al. BCL11A enhancer dissection by Cas9-mediated in situ saturating mutagenesis. Nature 527, 192-7 (2015).
16. Shi, J. et al. Discovery of cancer drug targets by CRISPR-Cas9 screening of protein domains. Nat Biotechnol 33, 661-7 (2015).
17. Komor, A. C., Kim, Y. B., Packer, M. S., Zuris, J. A. & Liu, D. R. Programmable editing of a target base in genomic DNA without double-stranded DNA cleavage. Nature 533, 420-4 (2016).
18. Gaudelli, N. M. et al. Programmable base editing of A•T to G•C in genomic DNA without DNA cleavage. Nature 551, 464-471 (2017).
19. Kan, Y., Ruis, B., Takasugi, T. & Hendrickson, E. Mechanisms of precise genome editing using oligonucleotide donors. Genome Res 27, 1099-1111 (2017).
20. Anders, C., Niewoehner, O., Duerst, A. & Jinek, M. Structural basis of PAM-dependent target DNA recognition by the Cas9 endonuclease. Nature 513, 569-73 (2014).

21. Kleinstiver, B. P. et al. High-fidelity CRISPR-Cas9 nucleases with no detectable genome-wide off-target effects. Nature 529, 490-5 (2016).
22. Nishimasu, H. et al. Engineered CRISPR-Cas9 nuclease with expanded targeting space. Science 361, 1259-1262 (2018).
23. Hu, J. H. et al. Evolved Cas9 variants with broad PAM compatibility and high DNA specificity. Nature 556, 57-63 (2018).
24. Anders, C., Bargsten, K. & Jinek, M. Structural Plasticity of PAM Recognition by Engineered Variants of the RNA-Guided Endonuclease Cas9. Mol Cell 61, 895-902 (2016).
25. Hirano, S., Nishimasu, H., Ishitani, R. & Nureki, O. Structural Basis for the Altered PAM Specificities of Engineered CRISPR-Cas9. Mol Cell 61, 886-94 (2016).
26. Suzuki, K. et al. In vivo genome editing via CRISPR/Cas9 mediated homology-independent targeted integration. Nature 540, 144-149 (2016).
27. Rees, H. A. & Liu, D. R. Base editing: precision chemistry on the genome and transcriptome of living cells. Nat Rev Genet 19, 770-788 (2018).
28. Koblan, L. W. et al. Improving cytidine and adenine base editors by expression optimization and ancestral reconstruction. Nat Biotechnol 36, 843-846 (2018).
29. Balemans, W. et al. Increased bone density in sclerosteosis is due to the deficiency of a novel secreted protein (SOST). Hum Mol Genet 10, 537-543 (2001).
30. Schuelke, M. et al. Myostatin Mutation Associated with Gross Muscle Hypertrophy in a Child. New Engl J Med 350, 2682-2688 (2004).
31. Cox, J. J. et al. Congenital insensitivity to pain: novel SCN9A missense and in-frame deletion mutations. Hum Mutat 31, E1670-86 (2010).
32. Flannick, J. et al. Loss-of-function mutations in SLC30A8 protect against type 2 diabetes. Nat Genet 46, 357-63 (2014).
33. and and of the Project, B. T. et al. Loss-of-function mutations in APOC3, triglycerides, and coronary disease. New Engl J Medicine 371, 22-31 (2014).
34. Harper, A. R., Nayee, S. & Topol, E. J. Protective alleles and modifier variants in human health and disease. Nat Rev Genetics 16, 689-701 (2015).
35. Investigators, M. et al. Inactivating mutations in NPCIL1 and protection from coronary heart disease. New Engl J Medicine 371, 2072-82 (2014).
36. Kleinstiver, B. P. et al. Engineered CRISPR-Cas12a variants with increased activities and improved targeting ranges for gene, epigenetic and base editing. Nat Biotechnol 37, 276-282 (2019).
37. Rohland, N. & Reich, D. Cost-effective, high-throughput DNA sequencing libraries for multiplexed target capture. Genome Res 22, 939-46 (2012).
38. Clement, K. et al. CRISPResso2 provides accurate and rapid genome editing sequence analysis. Nat Biotechnol 37, 224-226 (2019).
39. Gao, L. et al. Engineered Cpf1 variants with altered PAM specificities. Nat Biotechnol 35, 789-792 (2017).
40. Kleinstiver, B. P. et al. Broadening the targeting range of *Staphylococcus aureus* CRISPR-Cas9 by modifying PAM recognition. Nat Biotechnol 33, 1293-1298 (2015).
41. Guo, M. et al. Structural insights into a high fidelity variant of SpCas9. Cell Res 29, 183-192 (2019).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated *Streptococcus pyogenes* Cas9 (SpCas9) protein, comprising an amino acid sequence that has at least 95% sequence identity to the amino acid sequence of SEQ ID NO:1, wherein the amino acids at positions: 1135, 1136, 1218, 1219, 1335, and 1337 are: LWKQQR ("SpG"); LWRQQR; LWSQQR; LWKHQR; LWKSQR; LWRSQR; LWRSQK; LWSHQR; LWRHQR; LWRQQK; LWSQQK; LSKQQR; LWKQQK; LSKHQR; LWKSQK; LSRHQR; LWRVQK; LFRQQR; LSRQQR; LSRSQR; LARQQR; LSRVQR; ASREQR; WSREQR; LSREQR; FSREQR; LSKSQR; LWKVQK; LWKHQK; LWSSQK; LWSHQK; LWSSQR; LWRVQR; LSKVQR; LWRHQK; LSSQQR; LWKVQR; LWSVQR; LSSHQR; LWSVQR; LSSVQR; LSKQQK; LSRVQK; LSKVQK; LSSSQR; LSKSQK; LSSVQK; LSRQQK; LSSQQK; LSRSQK; or LSKHQK, respectively.

2. The isolated SpCas9 protein of claim 1, further comprising a mutation at R1333, wherein R is mutated to P, C, A, V, G, K, L, S, T, Y, Q, I, H, N, M, D, E, F, or W.

3. The isolated SpCas9 protein of claim 2, wherein the amino acids at positions: 1135, 1136, 1218, 1219, 1333, 1335, and 1337 are: LWKQPQR; LWKQCQR; LWKQAQR; LWKQVQR; LWKQGQR; LWKQSQR; LWKQTQR; LWKQKQR; LWKQLQR; LWKQYQR; LWKQQQR; LWKQIQR; LWKQHQR; LWKQNQR; LWKQMQR; LWKQDQR; LWKQEQR; LWKQFQR; or LWKQWQR, respectively, in SEQ ID NO:1.

4. The isolated SpCas9 protein of claim 1, further comprising a mutation at N1317, wherein N is mutated to R, K, or H; G1104, wherein G is mutated to K, H, or R; A61, wherein A is mutated to R, K, H; L1111, wherein L is mutated to R or K, and/or A1322, wherein A is mutated to R or K.

5. The isolated SpCas9 protein of claim 4, comprising amino acids LWKQPQR at positions 1135, 1136, 1218, 1219, 1333, 1335, and 1337, respectively, in SEQ ID NO:1, and further comprising one of the following sets of mutations:
   A61R+N1317R+L1111R+A1322R ("SpRY");
   G1104K+N1317R+L1111R+A1322R;
   A61R+G1104K+N1317R+L1111R+A1322R;
   A61R+G1104K+L1111R+A1322R;
   A61R+N1317R+L1111R+A1322R;
   G1104K+L1111R+A1322R;
   N1317R+L1111R+A1322R; or
   A61R+L1111R+A1322R.

6. The isolated SpCas9 protein of claim 1, further comprising: (i) a mutation at a position selected from the group consisting of D10, E762, D839, H983, or D986; and/or
   (ii) a mutation at position H840 or N863.

7. The isolated SpCas9 protein of claim 6, wherein the mutations are:
   (i) D10A or D10N, and/or
   (ii) H840A, H840N, or H840Y.

8. The isolated SpCas9 protein of claim 1, further comprising one or more mutations that increase specificity selected from the group consisting of mutations at N497, R661, N692, M694, Q695, H698, K810, K848, Q926, K1003, R0160, R691, M495, Y515, K526, R661, and combinations thereof.

9. The isolated SpCas9 protein of claim 8, further comprising mutations at R691A, M495V, Y515N, K526E, R661Q, R661L, R661S, Y450A/Q695A, L169A/Q695A, Q695A/Q926A, Q695A/D1135E, Q926A/D1135E, Y450A/D1135E, L169A/Y450A/Q695A, L169A/Q695A/Q926A, Y450A/Q695A/Q926A, R661A/Q695A/Q926A, N497A/Q695A/Q926A, Y450A/Q695A/D1135E, Y450A/Q926A/D1135E, Q695A/Q926A/D1135E, L169A/Y450A/Q695A/Q926A, L169A/R661A/Q695A/Q926A, Y450A/R661A/Q695A/Q926A, N497A/Q695A/Q926A/D1135E, R661A/Q695A/Q926A/D1135E, and Y450A/Q695A/Q926A/D1135E; N692A/M694A/Q695A/H698A, N692A/M694A/Q695A/H698A/Q926A; N692A/M694A/Q695A/Q926A; N692A/M694A/H698A/Q926A; N692A/Q695A/H698A/Q926A; M694A/Q695A/H698A/Q926A; N692A/Q695A/H698A; N692A/M694A/Q695A; N692A/H698A/Q926A; N692A/M694A/Q926A; N692A/M694A/H698A; M694A/Q695A/H698A; M694A/Q695A/Q926A; Q695A/H698A/Q926A; G582A/V583A/E584A/D585A/N588A/Q926A; G582A/V583A/E584A/D585A/N588A; T657A/G658A/W659A/R661A/Q926A; T657A/G658A/W659A/R661A; F491A/M495A/T496A/N497A/Q926A; F491A/M495A/T496A/N497A; K918A/V922A/R925A/Q926A; or 918A/V922A/R925A; K855A; K810A/K1003A/R1060A; K848A/K1003A/R1060A; M495V/Y515N/K526E/R661Q; M495V/Y515N/K526E/R661L; or M495V/Y515N/K526E/R661S.

10. A fusion protein comprising the isolated SpCas9 protein of claim 1, fused to a heterologous functional domain.

11. The fusion protein of claim 10, wherein the heterologous functional domain is a transcriptional activation domain.

12. The fusion protein of claim 11, wherein the transcriptional activation domain is from VP16, VP64, rTA, NF-κB p65, or the composite VPR (VP64-p65-rTA).

13. The fusion protein of claim 10, wherein the heterologous functional domain is a transcriptional silencer or transcriptional repression domain.

14. The fusion protein of claim 13, wherein the transcriptional repression domain is a Krueppel-associated box (KRAB) domain, ERF repressor domain (ERD), or mSin3A interaction domain (SID).

15. The fusion protein of claim 13, wherein the transcriptional silencer is Heterochromatin Protein 1 (HP1).

16. The fusion protein of claim 10, wherein the heterologous functional domain is an enzyme that modifies the methylation state of DNA.

17. The fusion protein of claim 16, wherein the enzyme that modifies the methylation state of DNA is a DNA methyltransferase (DNMT) or a TET protein.

18. The fusion protein of claim 17, wherein the TET protein is TET1.

19. The fusion protein of claim 10, wherein the heterologous functional domain is an enzyme that modifies a histone subunit.

20. The fusion protein of claim 19, wherein the enzyme that modifies a histone subunit is a histone acetyltransferase (HAT), histone deacetylase (HDAC), histone methyltransferase (HMT), or histone demethylase.

21. The fusion protein of claim 10, wherein the heterologous functional domain is a base editor or a prime editor.

22. The fusion protein of claim 21, wherein the base editor is a DNA or RNA deaminase; or wherein the prime editor comprises a reverse transcriptase (RT) domain.

23. The fusion protein of claim 22, wherein the base editor is a cytosine or adenine deaminase domain, or activation-induced cytidine deaminase.

24. The fusion protein of claim 10, wherein the heterologous functional domain is a biological tether.

25. The fusion protein of claim 24, wherein the biological tether is MS2, Csy4 or lambda N protein.

26. The fusion protein of claim 10, wherein the heterologous functional domain is FokI.

27. An isolated nucleic acid encoding the isolated SpCas9 protein of claim 1.

28. A vector comprising the isolated nucleic acid of claim 27.

29. The vector of claim 28, wherein the isolated nucleic acid of claim 27 is operably linked to one or more regulatory domains for expressing the isolated *Streptococcus pyogenes* Cas9 (SpCas9) protein.

30. An isolated host cell, comprising the nucleic acid of claim 27.

31. The host cell of claim 30, wherein the host cell is a mammalian host cell.

32. A method of altering the genome of a cell, the method comprising expressing in the cell, or contacting the cell with, the isolated protein of claim 1, and a guide RNA having a region complementary to a selected portion of the genome of the cell.

33. The method of claim 32, wherein the isolated protein comprises one or more of a nuclear localization sequence, cell penetrating peptide sequence, and/or affinity tag.

34. The method of claim 33, wherein the cell is a stem cell.

35. The method of claim 34, wherein the cell is an embryonic stem cell, mesenchymal stem cell, or induced pluripotent stem cell; is in a living non-human animal; or is in a non-human embryo.

36. A method of altering a double stranded DNA (dsDNA) molecule, the method comprising contacting the dsDNA molecule with the isolated protein of claim 1, and a guide RNA having a region complementary to a selected portion of the dsDNA molecule.

37. The method of claim 36, wherein the dsDNA molecule is in vitro.

38. The method of claim 36, wherein the isolated SpCas9 protein and RNA are in a ribonucleoprotein complex.

* * * * *